United States Patent
Petersson

(10) Patent No.: US 9,376,700 B2
(45) Date of Patent: Jun. 28, 2016

(54) METHODS OF MODIFYING N-TERMINI OF A PEPTIDE OR PROTEIN USING TRANSFERASES

(71) Applicant: The Trustees of the University of Pennsylvania, Philadelphia, PA (US)

(72) Inventor: E. James Petersson, Wynnewood, PA (US)

(73) Assignee: The Trustees of the University of Pennsylvania, Philadelphia, OR (US)

( * ) Notice: Subject to any disclaimer, the term of this patent is extended or adjusted under 35 U.S.C. 154(b) by 0 days.

(21) Appl. No.: 14/406,864

(22) PCT Filed: Jun. 13, 2013

(86) PCT No.: PCT/US2013/045542
§ 371 (c)(1),
(2) Date: Dec. 10, 2014

(87) PCT Pub. No.: WO2013/188607
PCT Pub. Date: Dec. 19, 2013

(65) Prior Publication Data
US 2015/0140605 A1    May 21, 2015

Related U.S. Application Data

(60) Provisional application No. 61/659,559, filed on Jun. 14, 2012.

(51) Int. Cl.
| | | |
|---|---|---|
| *C07K 1/113* | (2006.01) | |
| *C12P 21/00* | (2006.01) | |
| *A61K 38/00* | (2006.01) | |
| *C07K 1/02* | (2006.01) | |
| *C07K 1/13* | (2006.01) | |
| *C07C 247/16* | (2006.01) | |
| *C07C 255/03* | (2006.01) | |
| *C07D 311/08* | (2006.01) | |
| *C07D 473/34* | (2006.01) | |

(52) U.S. Cl.
CPC ............... *C12P 21/00* (2013.01); *A61K 38/00* (2013.01); *C07C 247/16* (2013.01); *C07C 255/03* (2013.01); *C07D 311/08* (2013.01); *C07D 473/34* (2013.01); *C07K 1/026* (2013.01); *C07K 1/113* (2013.01); *C07K 1/13* (2013.01)

(58) Field of Classification Search
None
See application file for complete search history.

(56) References Cited

PUBLICATIONS

PCT International Search Report and Written Opinion for PCT/US2013/045542 issued Nov. 1, 2013.
Hondal, et al., "Selenocysteine in native chemical ligation and expressed protein ligation", J Am Chem Soc. 123(21), May 30, 2001, 5140-1.
Wagner, et al., "N-terminal protein modification using simple aminoacyl transferase substrates", J Am Chem Soc. 133(38), Sep. 28, 2011, 15139-47.
Wan, et al., "Free-radical-based, specific desulfurization of cysteine: a powerful advance in the synthesis of polypeptides and glycopolypeptides", Angew Chem Int Ed Engl. 46(48), 2007, 9248-52.

*Primary Examiner* — Ralph Gitomer
(74) *Attorney, Agent, or Firm* — Saul Ewing LLP; Kathryn Doyle; Domingos J. Silva

(57) ABSTRACT

The invention includes a selective method of modifying the N-terminus of a protein using an aminoacyl tRNA transferase. In certain embodiments, the method comprises contacting a solution of the protein or peptide with a transferase and a derivative of a molecule, whereby the N-terminus of the protein or peptide is derivatized with the molecule.

9 Claims, 32 Drawing Sheets

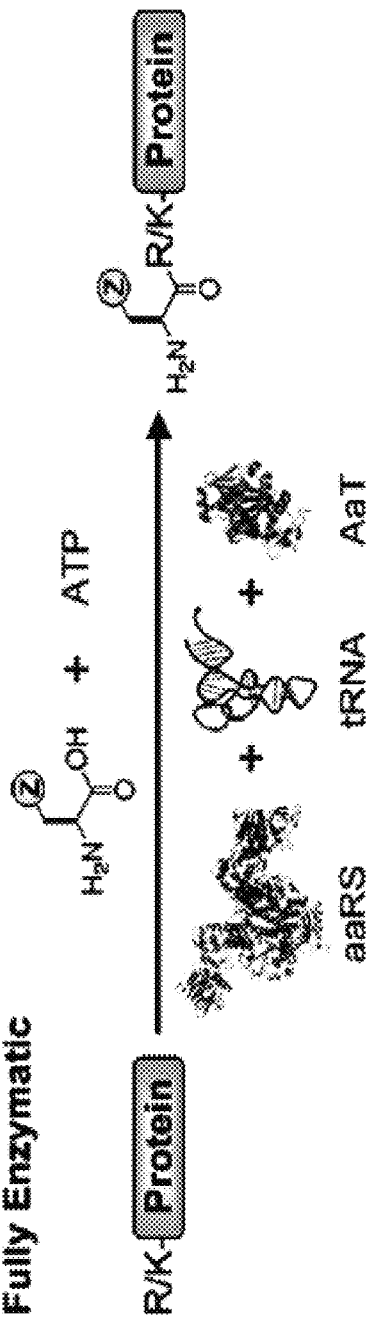
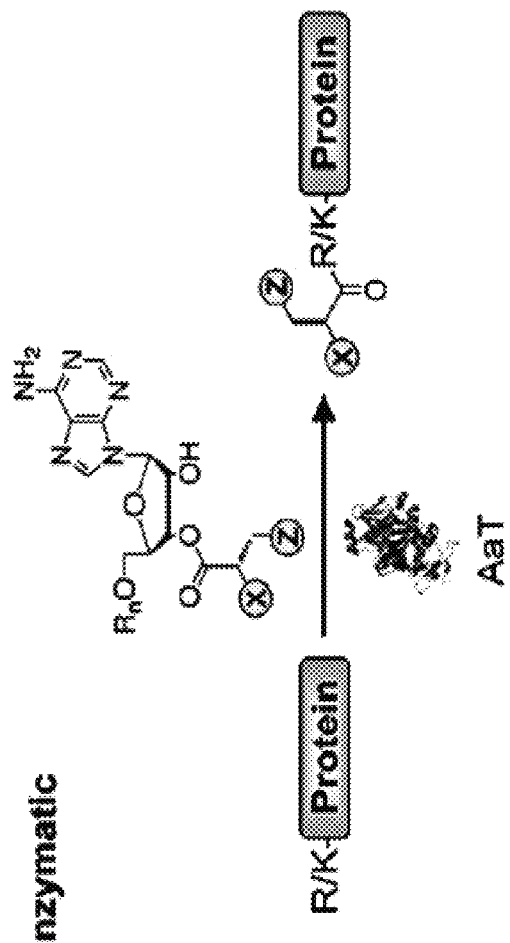
Fig. 1A Fully Enzymatic
Fig. 1B Chemoenzymatic

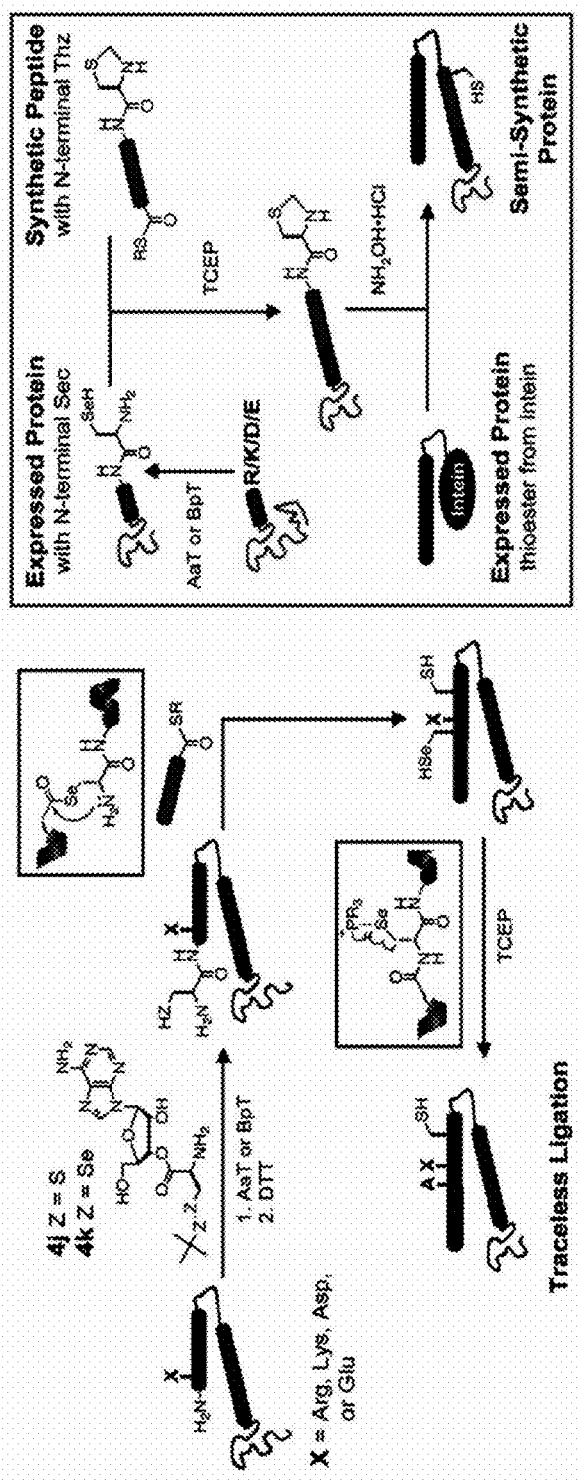
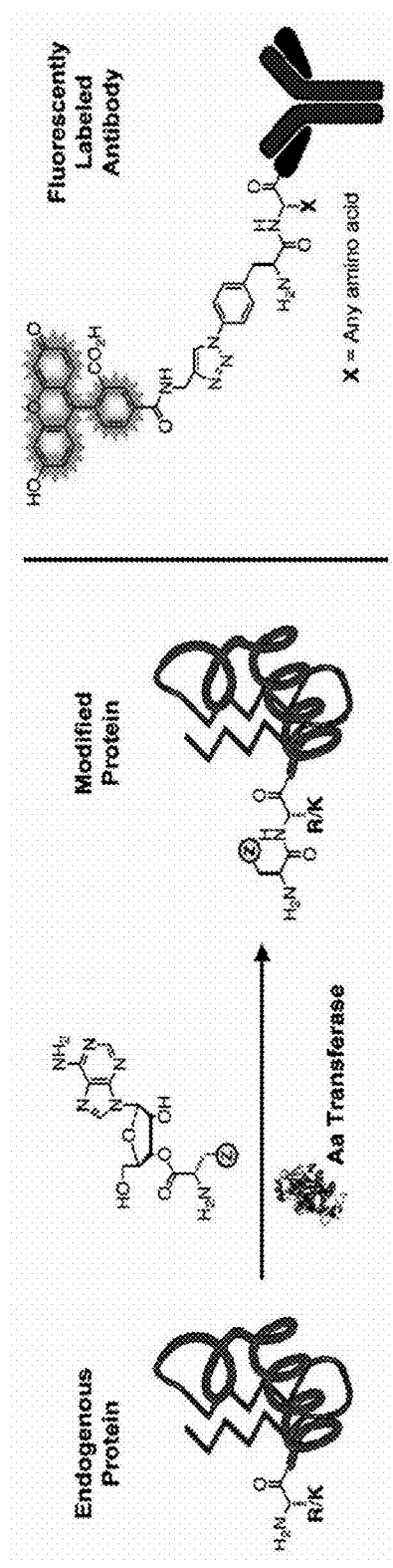
Fig. 2B

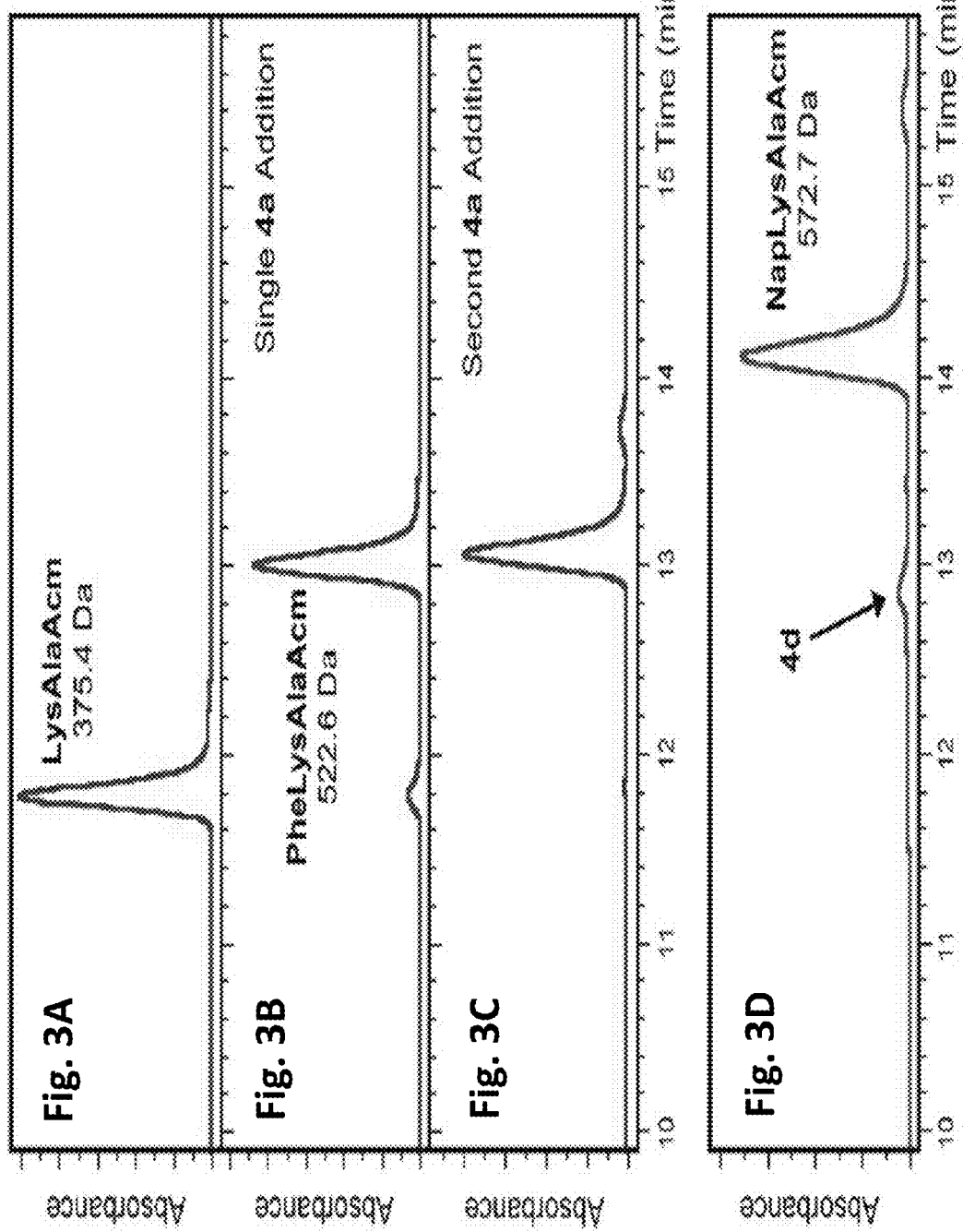

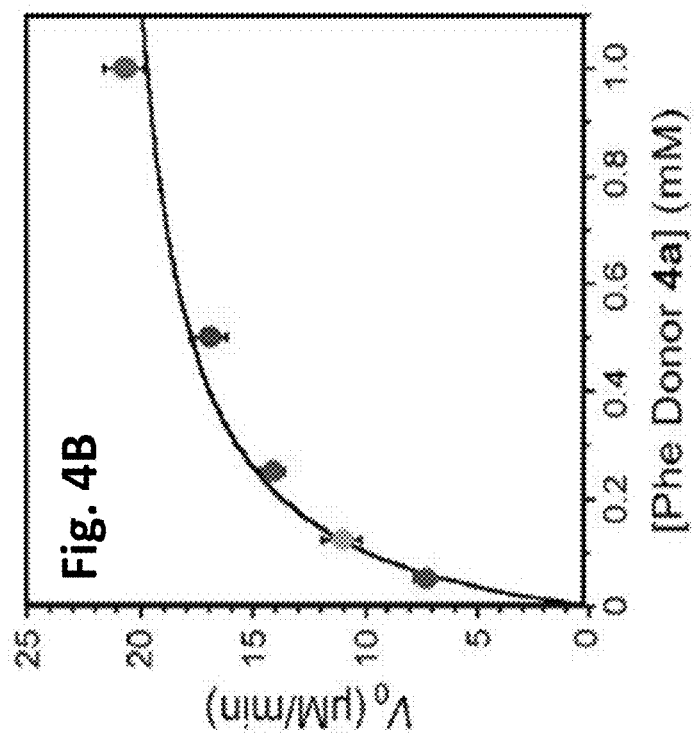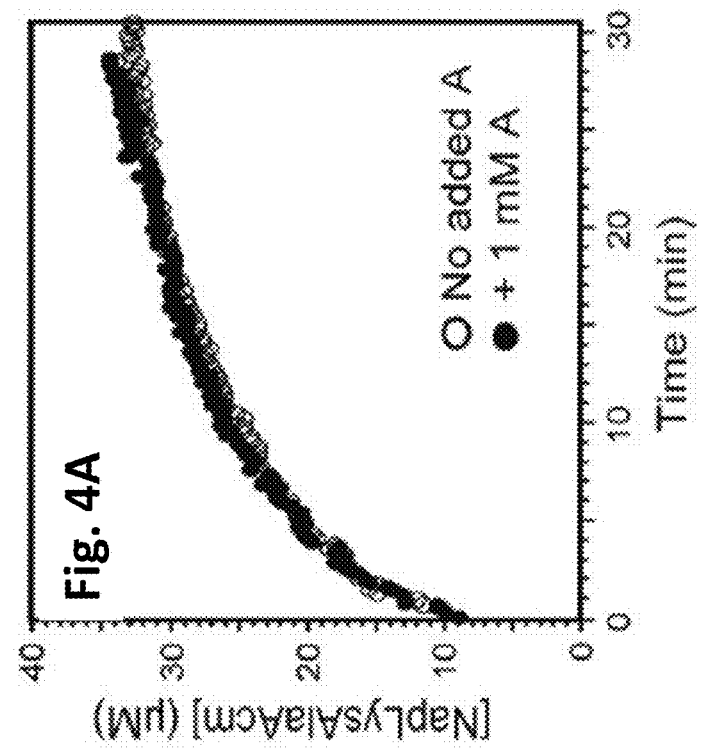
Fig. 4A
Fig. 4B

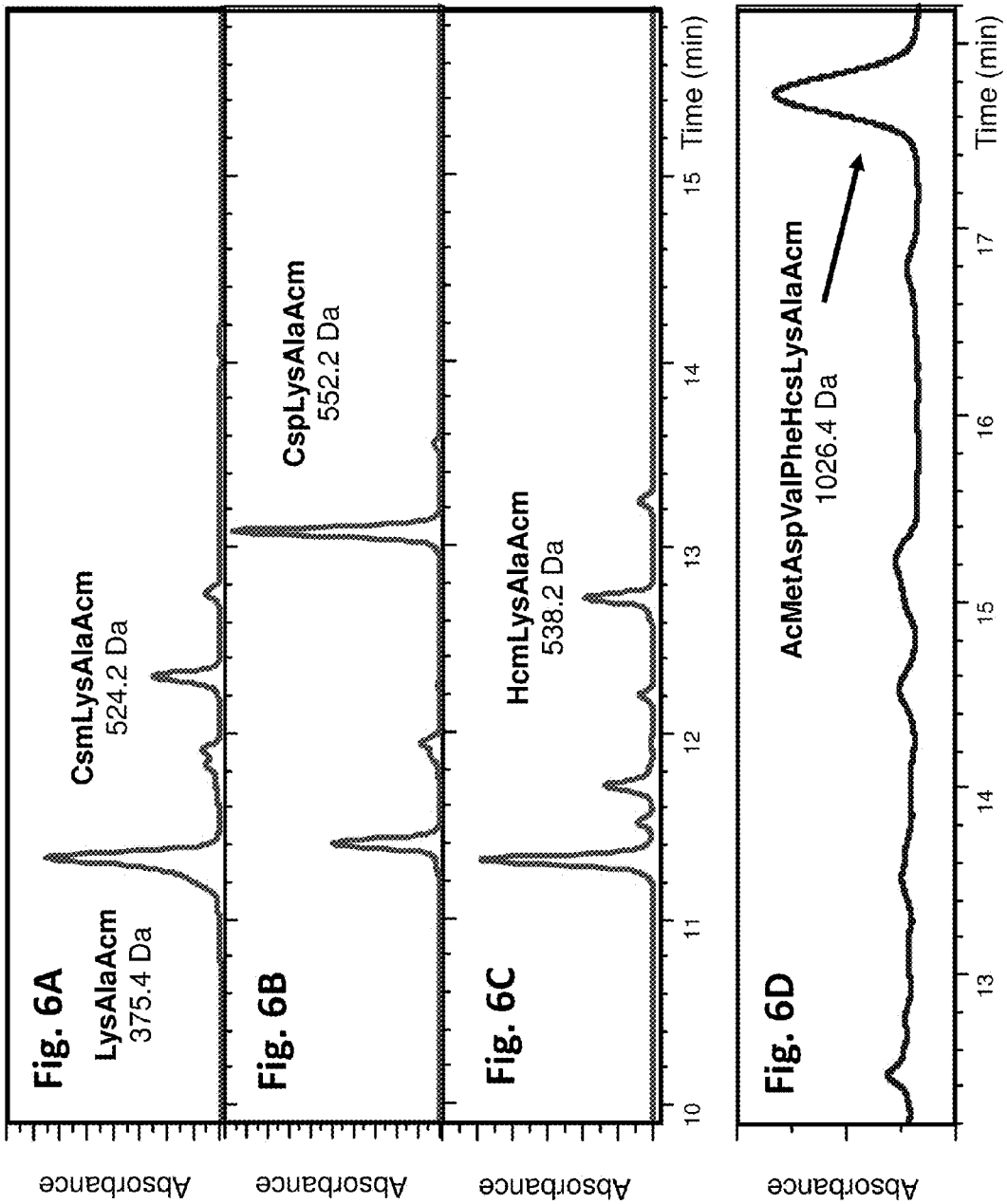

Boc-Leu-(DMT)-A (3b)
¹H NMR

Boc-Leu-(DMT)-A (3b)
$^{13}$C NMR

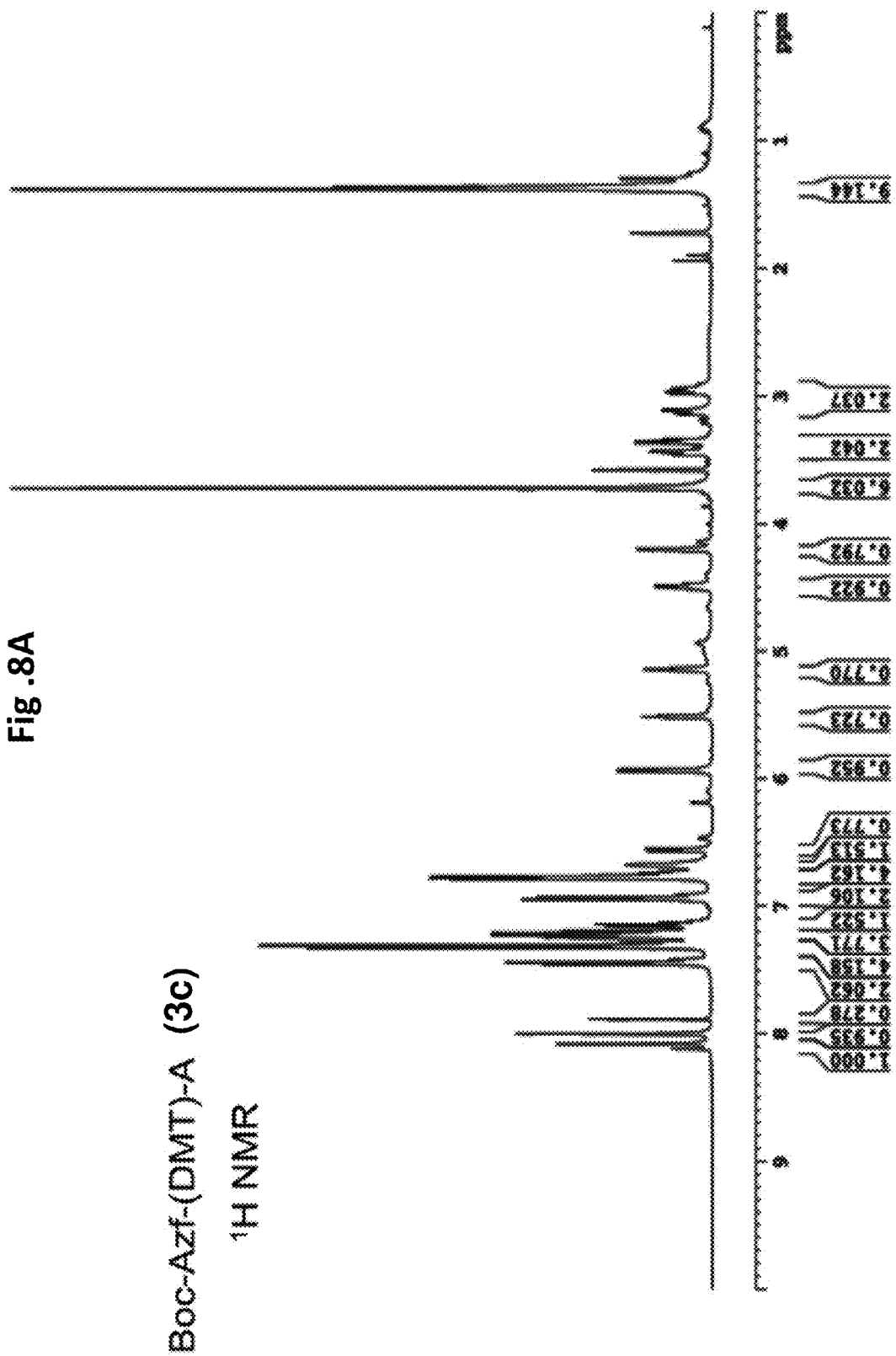

Boc-Azf-(DMT)-A (3c)
$^{13}$C NMR

Boc-Nap-(DMT)-A (3d)
¹H NMR

Boc-Nap-(DMT)-A (3d)
$^{13}$C NMR

Boc-Mef-(DMT)-A (3e)
¹H NMR

Boc-Mef-(DMT)-A (3e)
$^{13}$C NMR

Boc-Acf-(DMT)-A (3f)
¹H NMR

Boc-Acf-(DMT)-A (3f)
$^{13}$C NMR

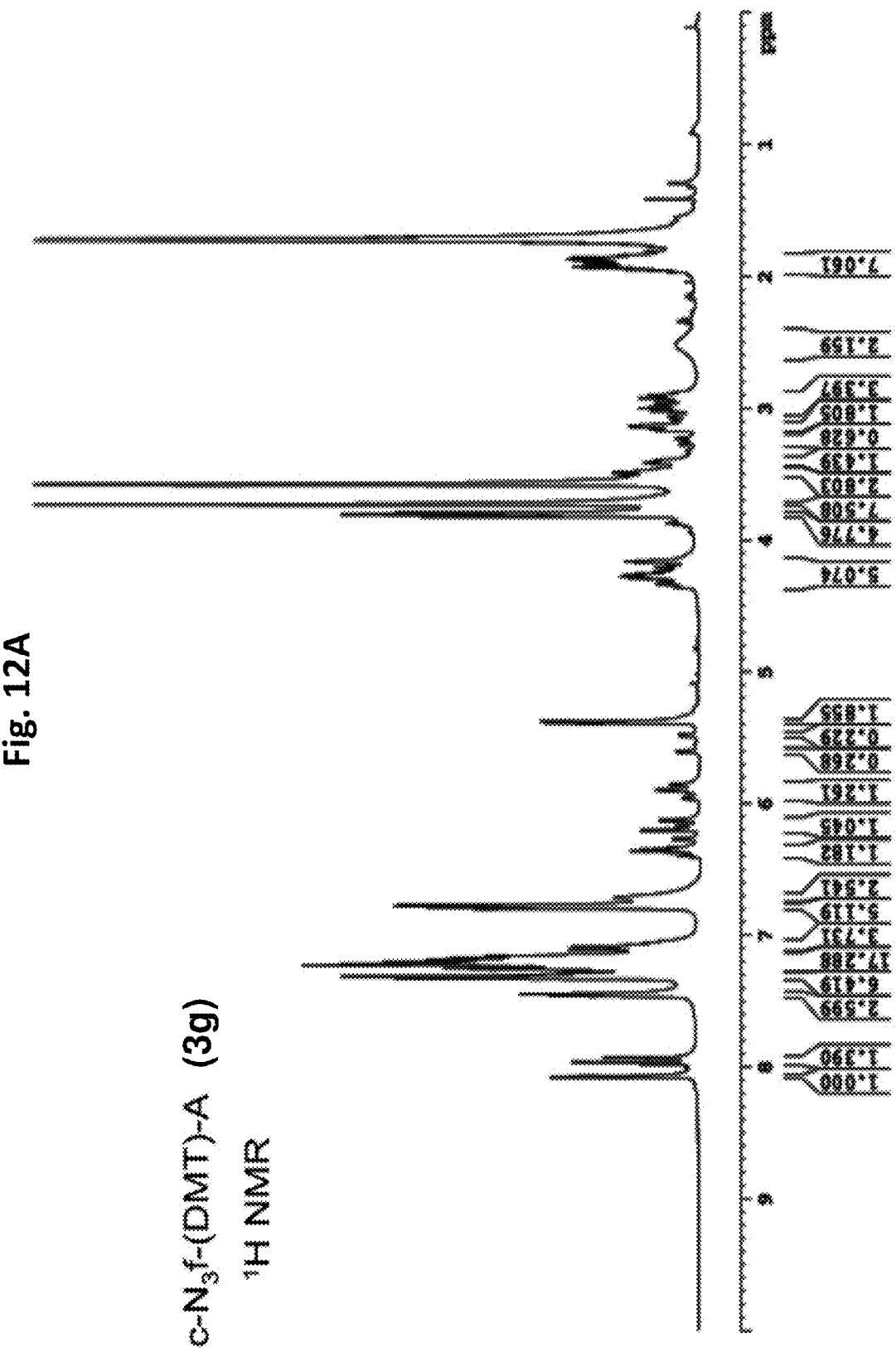

Boc-N₃f-(DMT)-A (3g)
$^{13}$C NMR

Boc-Mcm-(DMT)-A (3h)
1H NMR

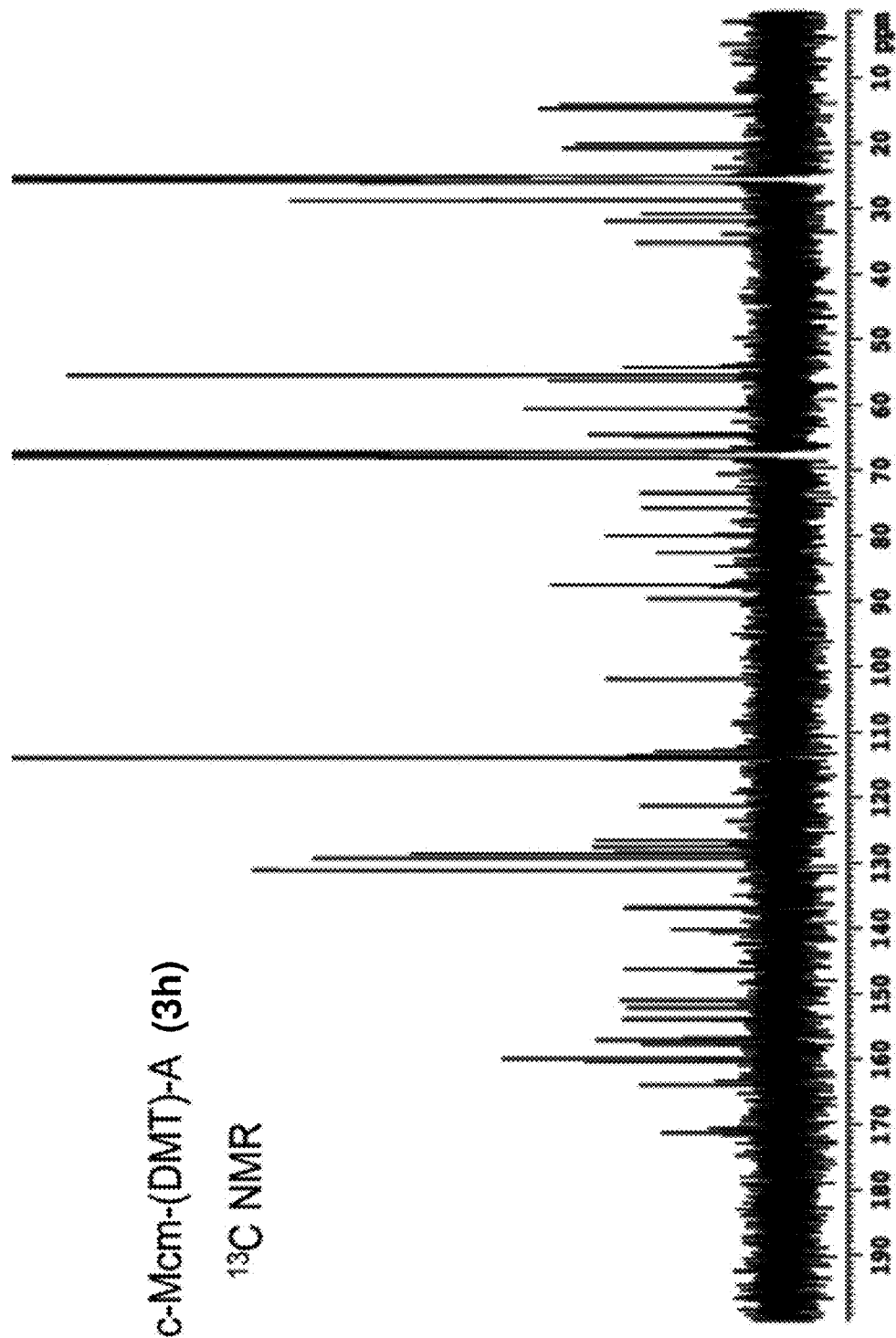

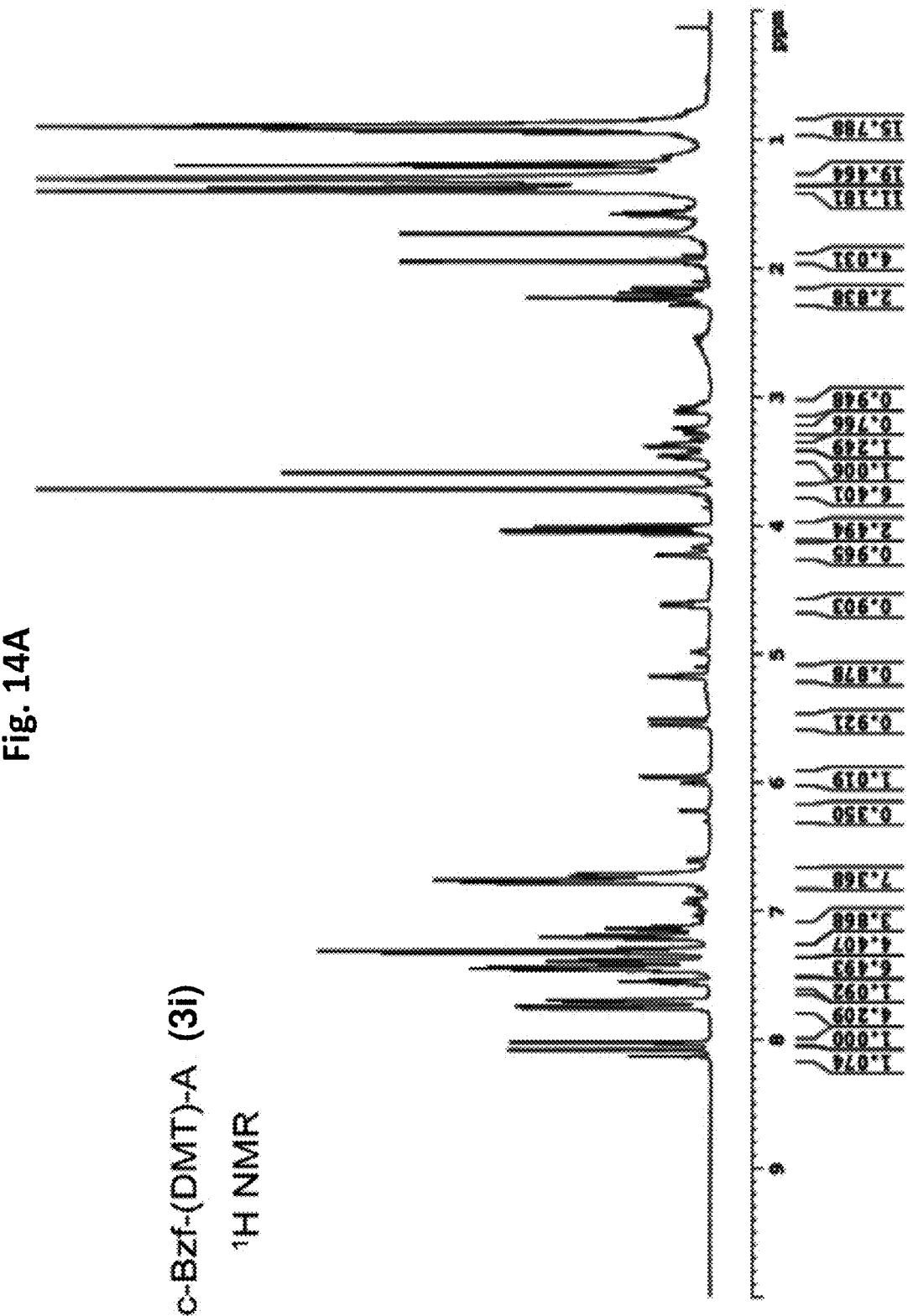

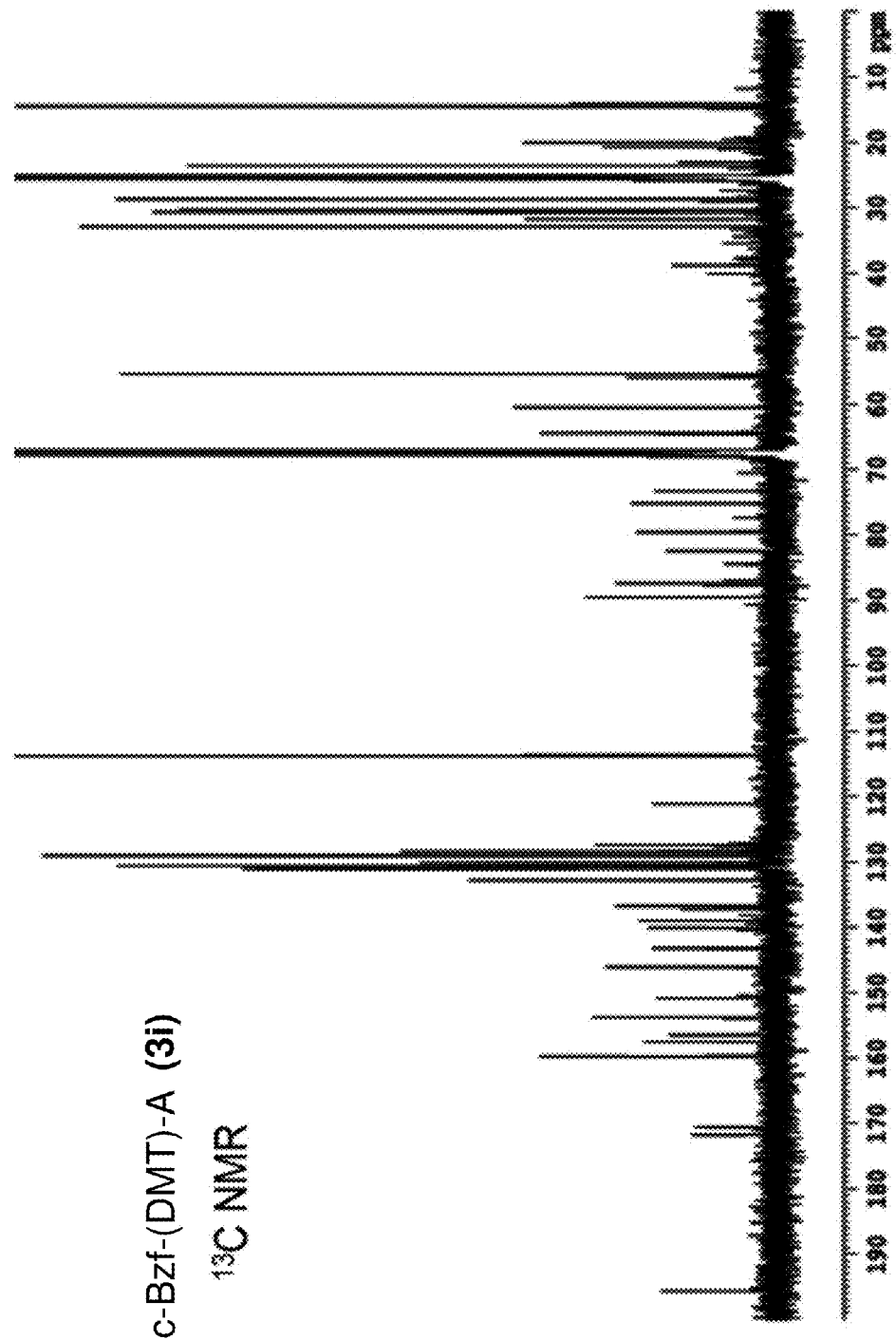

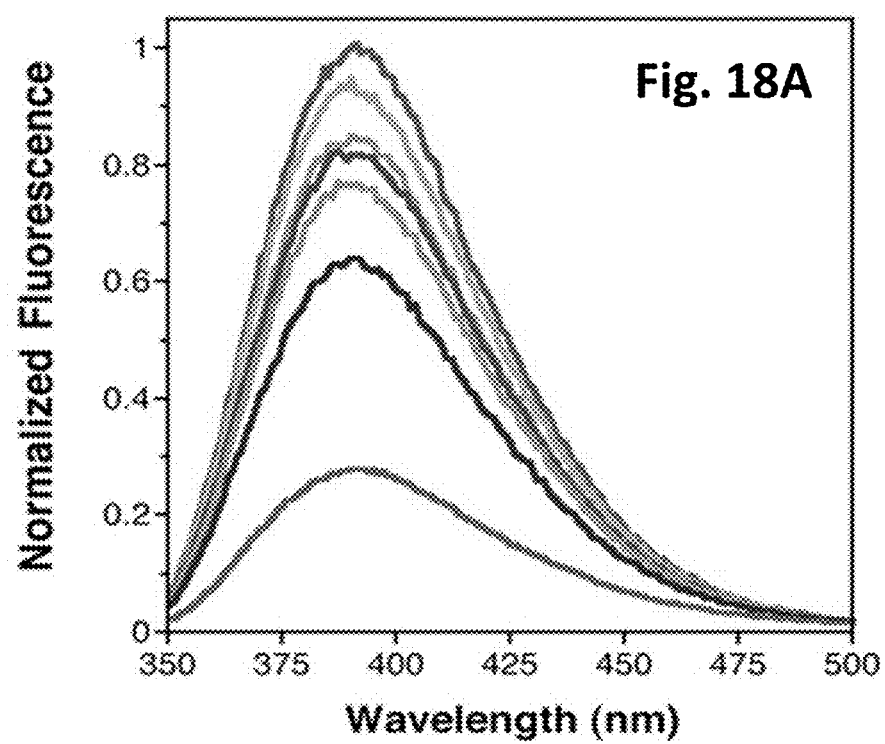
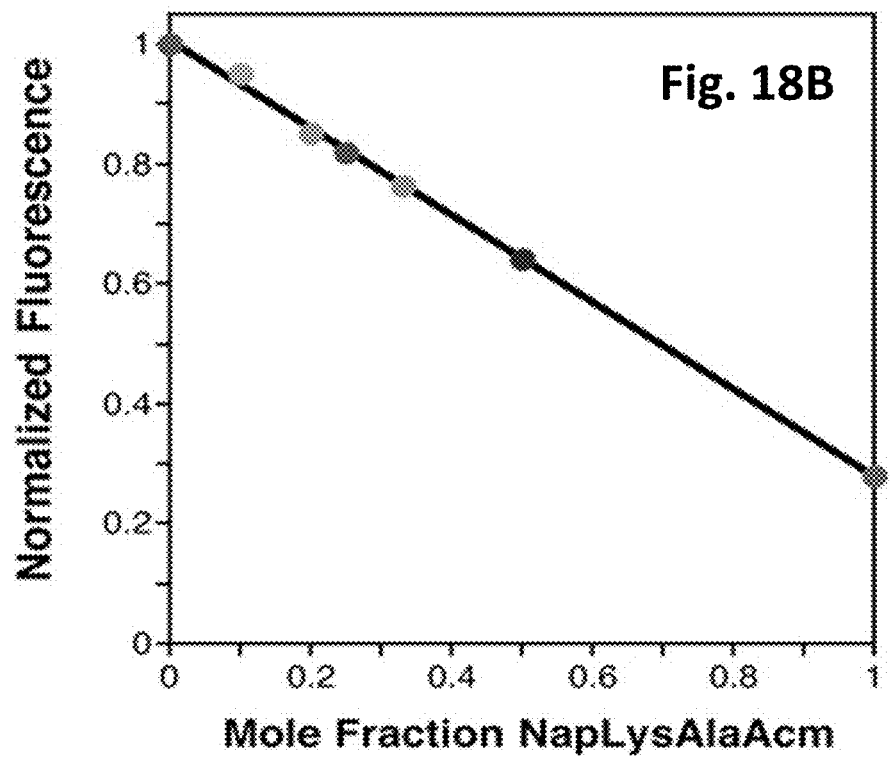

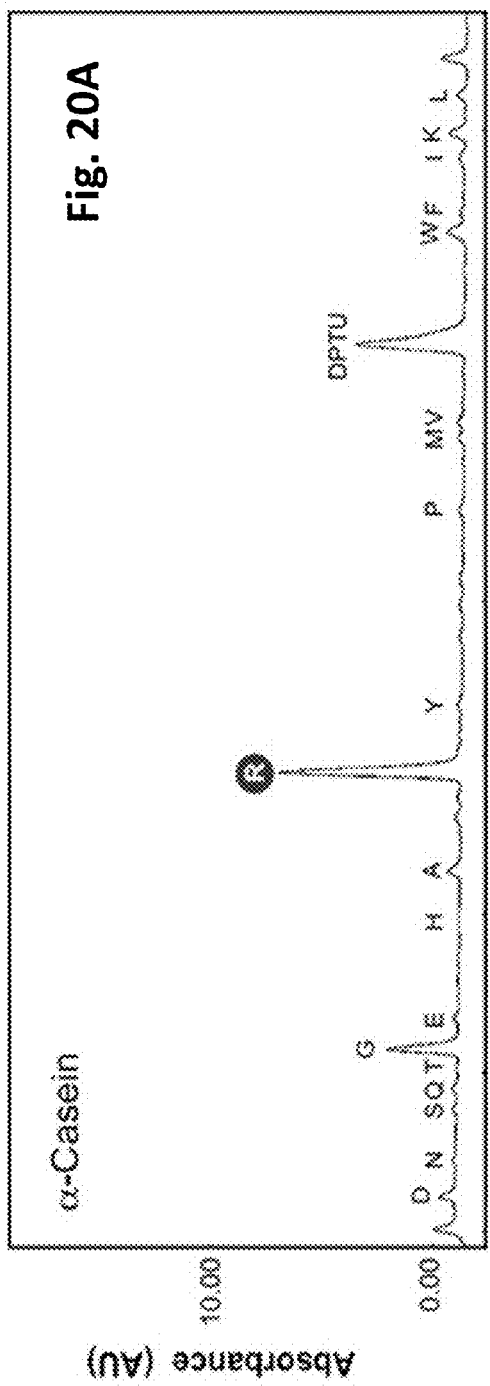
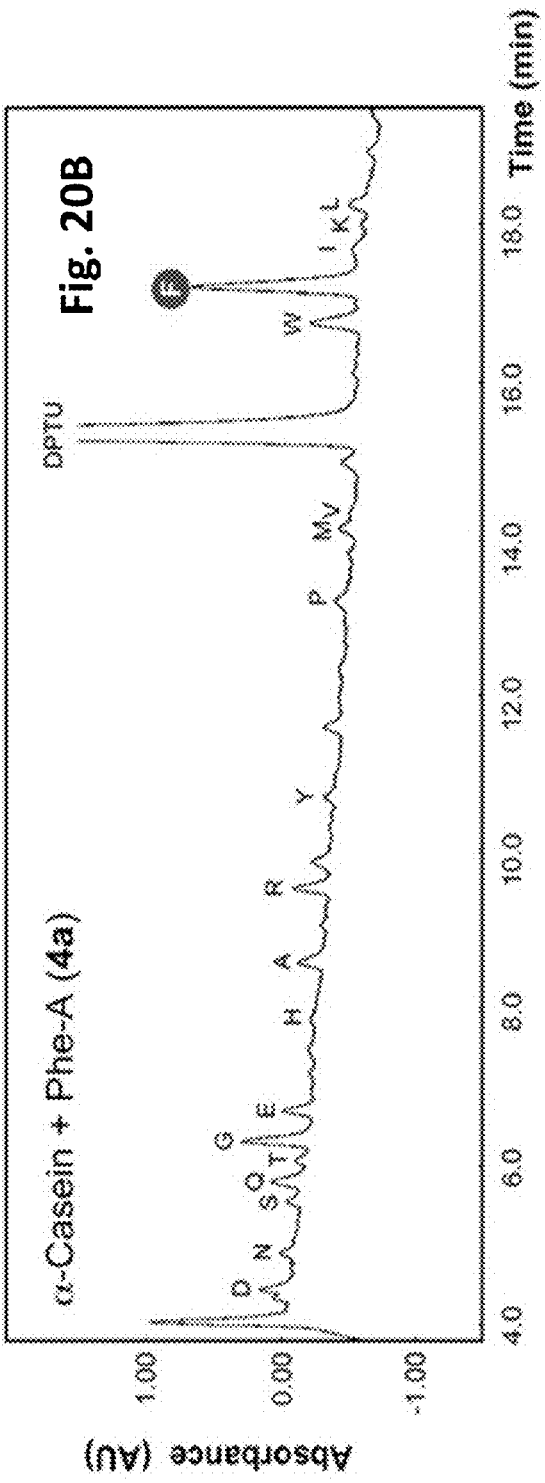

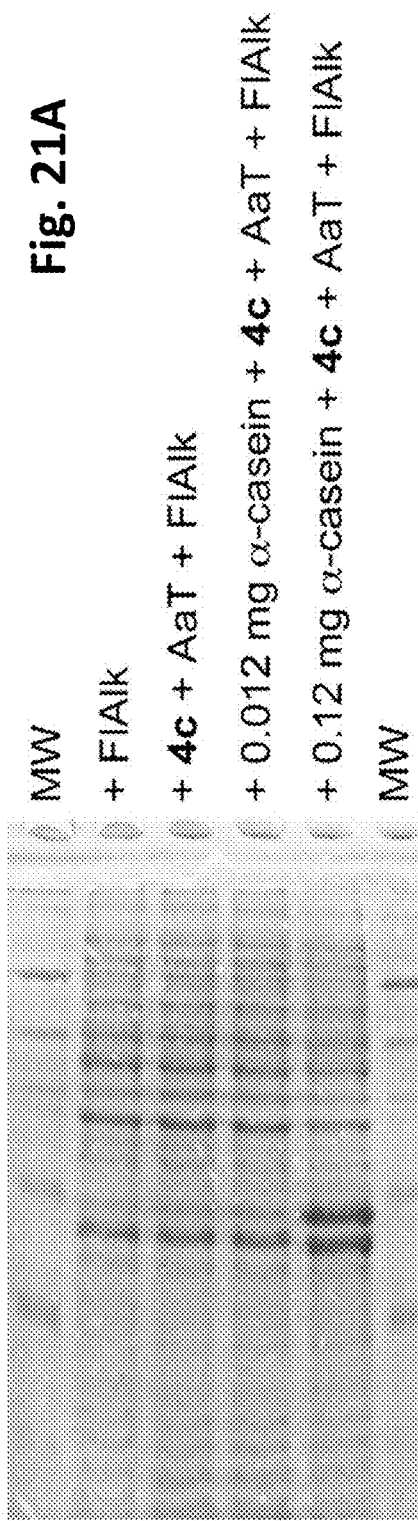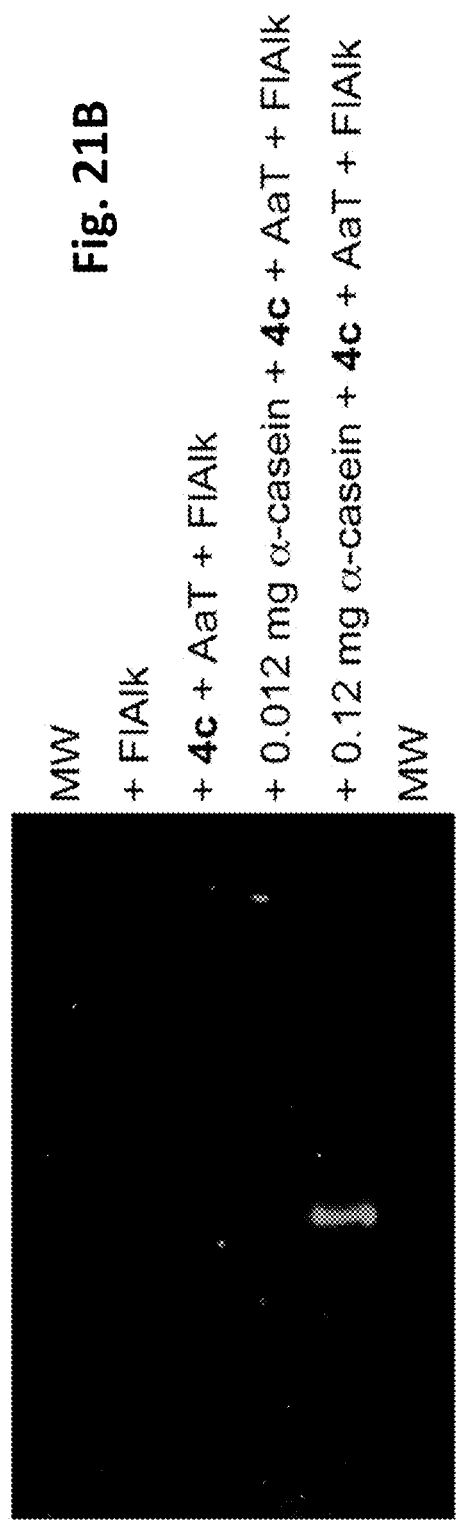

Fig. 22
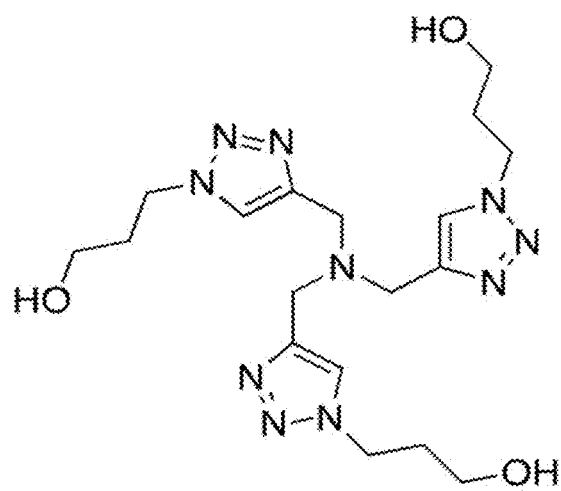
Tris(hydroxypropyltriazoylmethyl)amine
THPTA
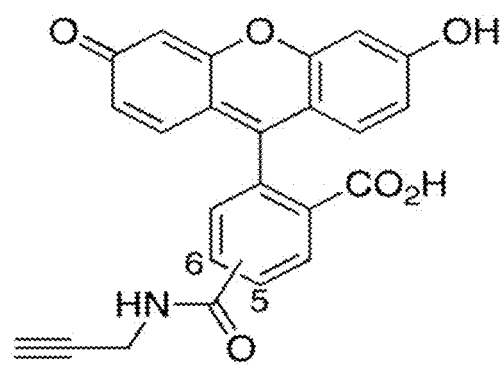
Fluorescein 5- and 6-Propargylamide
FlAlk

METHODS OF MODIFYING N-TERMINI OF A PEPTIDE OR PROTEIN USING TRANSFERASES

CROSS-REFERENCE TO RELATED APPLICATIONS

This application is a 35 U.S.C. §371 national phase application of, and claims priority to, PCT Application No. PCT/US13/45542, filed Jun. 13, 2013, which claims priority to U.S. Provisional Application No. 61/659,559, filed Jun. 14, 2012, all of which are incorporated by reference herein as set forth herein in their entireties.

STATEMENT REGARDING FEDERALLY SPONSORED RESEARCH OR DEVELOPMENT

This invention was made with government support under grant number RR-023444 awarded by the National Institutes of Health (NIH) and grant number MRI-0820996 awarded by the National Science Foundation (NSF). The government has certain rights in the invention.

BACKGROUND OF THE INVENTION

The conjugation of synthetic molecules to proteins is a key strategy in biomedical research, allowing for proteins to be immobilized onto surfaces, modified with chromophores to prepare in vitro sensors, or tagged with in vivo imaging agents (Wu et al., 1997. Fluorescence Spectroscopy 278:321-330; Harris et al, 2003, Nat. Rev. Drug Disc. 2:214-221; Wang et al 2005, Angew. Chem. Int. Ed. 44:34-66; Basle et al., 2010, Chem. Biol. 17:213-227; Canalle et al., 2010, Chem. Soc. Rev, 39:329-353). Examples of such conjugation include protein microarrays to investigate protein-protein interactions, and proteins labeled with near-IR quantum dots for imaging in deep tissue. Protein modification can also significantly improve protein properties so that they may be used as therapeutic and diagnostic agents: thermostability, resistance to degradation (both enzymatic and non-enzymatic in nature), increase in solubility, and improved formulation characteristics. Degradation-resistant modifications have been achieved by PEG modification of proteins and diagnostic antibodies. In most cases, the formation of well-defined conjugates is valuable, if not essential, for product development.

The protein termini are attractive targets for conjugation, because in many cases appending synthetic molecules at the termini will have minimal undesired effects on protein folding and function, especially when the terminus is relatively unstructured. (Alouani et al., 1995, Eur. J. Biochem. 227:328-334; Kinstler et al., 1996, J. Pharm. Res. 13; 996-1002; Gale et al., 1999, J. Chem. Soc. Perkin 1:2267-2270; Ramachandiran et al., 2000, J. Biol. Chem. 275:1781-1786; Jones et al., 2001, J. Bioconj. Chem. 12:1012-1020; Kinstler et al., 2002, Adv. Drug Deliv. Rev. 54:477-485; Chelius et al., 2003, Bioconj. Chem. 14:205-211; Arduini et al., 2004, Protein Exp. Purif. 34; 229-242; Mamaev et al., 2004, J. Anal. Biochem. 326:25-32; Baker et al., 2006, Bioconj. Chem. 17:179-188; Scheck et al., 2007, ACS Chem. Biol. 2:247-251; Merkel et al., 2008, ChemBioChem 9:1220-1224; Sharon et al., 2008, Biomaterials 29:3137-3142; Ebhardt et al., 2009, Anal. Chem. 81:1937-1943; Gao et al., 2009, Proc. Natl. Acad. Sci. USA 106:15231-15236; Sayers et al., 2009, Soft Matter 5; 3038-3046; Xiao et al., 2009, Org. Lett. 11:4144-4147; Jia et al., 2010, Mol. Biosyst. 6:1829-1833; Wang, et al., 2010, Anal. Biochem. 412:114-11.6; Wildes, et al., 2010, Proc. Natl. Acad. Sci. USA 107:4561-4566; Wu et al., 2010, J. App. Poly. Sci. 118:3269-3273). In addition, functionalized N-termini can be ligated to synthetic peptides to produce semi-synthetic proteins (Hackenberger et al., 2008, Angew. Chem. Int. Ed. 47:10030-10074).

Selective N-terminal modification has been achieved by various chemical and enzymatic methods, each with benefits and drawbacks. Small-molecule strategies permit the attachment of molecules to the protein N-terminus, but are subject to side reactions, incomplete specificity for the N-terminus and may need to be carried out in organic solvent mixtures (Scheck et al., 2007, ACS Chem. Biol. 2:247-251; Dixon et al., 1962, Biochem. J. 84:462-468; Dixon et al., 1964, Biochem. J. 92; 661-666; Geoghegan et al., 1979, Biochemistry 18; 5392-5399; Dixon, 1984, J. Protein Chem. 3:99-108; Acharya et al., 1987, Biochemistry 26:3524-3530; Qasmi et al., 1994, Tet. Lett. 35:4343-4344; Li et al., 2000, Tet. Lett. 41:4069-4073; Gilmore et al., 2006, Angew. Chem. Int. Ed, 45:5307-5311; Scheck et al., 2008, J. Am. Chem. Soc. 130: 11762-11770; Witus et al., 2010, J. Am. Chem. Soc. 132; 16812-16817). Reverse proteolysis methods can be used to modify the N-terminus under conditions that do not require protein unfolding, but the reaction can be difficult to drive to completion in the absence of high protein concentrations (Kuhl et al., 1980, Tet. Lett. 21:893-896; Jakubke et al., 1985, Angew. Chem. Int. Ed. 24:85-93; Schellenberger et 1991, Angew. Chem. Int. Ed. 301437-1449; Chang et al., 1994, Proc. Natl. Acad. Sci. USA 91:12544-12548; Jackson et al., 1994, Science 266:243-247; Bordusa et 1997, Angew. Chem. Int. Ed. 36:2473-2475; Braisted et 1997, Solid-Phase Peptide Synthesis 289:298-313; Atwell et al., 1999, Proc. Natl. Acad. Sci. USA 96:9497-9502; Bordusa, 2002, Chem. Rev. 102: 4817-4867; Tolbert et al., 2002, Angew. Chem. Int. Ed. 41:2171-2174; Muir, 2003, Annu. Rev. Biochem. 72:249-289; Wehofsky et al., 2003, J. Am. Chem. Soc. 125:6126-6133; Gentle et al., 2004, Bioconj. Chem. 15:658-663; Yoshihara et al., 2008, Bioorg. Med. Chem. Lett. 18; 6000-6003), Chemoenzymatic methods have been shown to function under mild conditions but require that moderate-sized target sequences be appended to the protein (Mazmanian et al., 1999, Science 285; 760-763; Mao et al., 2004, J. Am. Chem. Soc. 126:2670-2671; Tanaka et al., 2005, FEBS Lett. 579: 2092-2096; Popp et al., 2007, Nat. Chem. Biol. 3; 707-708; Fontana et al., 2008, Adv. Drug Deliv. Rev. 60:13-28; Heal et al., 2008, Org. Biomol. Chem. 6:2308-2315; Tsukiji et al., 2009, ChemBioChem 10:787-798; Nelson et al., 2010, ACS Chem. Biol. 5:1147-1155; Heal et al, 2012, Nat. Methods 7:105-117).

Aminoacyl tRNA transferases (such as *E. coli* AaT and *V. vulnificus* BpT) are members of a growing class of enzymes that use aminoacyl tRNAs in secondary metabolism (Lahoud et al., 2010, Nat. Chem. Biol. 6:795-796). AaT catalyzes the transfer of Leu, Phe, or Met from an aminoacyl tRNA to a protein bearing an N-terminal Arg or Lys (Kaji et al., 1963, Biochem. Biophys. Res. Comm. 10; 406-409; Suto et al., 2006, EMBO J. 25; 5942-5950; Watanabe et al., 2007, Nature 449:867-871). BpT catalyzes the transfer of Leu from an aminoacyl tRNA to a protein bearing an N-terminal Asp or Glu (Graciet et al., 2006, Proc. Natl. Acad. Sci. USA 103: 3078-3083). The addition of Leu or Phe targets that protein for degradation by ClpA as part of the N-end rule pathway (Mogk et al., 2007, Trends Cell Biol. 17; 165-172; Tobias et al., 1991, Science 254; 1374-1377; Varshaysky, 2008, Nat. Struct. Mol. 15:1238-1240; Schuenemann et al., 2009, EMBO Rep. 10:508-514). Kaji and co-workers observed AaT aminoacylation activity in crude *E. coli* preparations (Kaji et al., 1963, Biochem. Res. Commun. 10:406-409; Kaji et al., 1965, J. Biol. Chem. 240:1185-1191; Kaji et al., 1965, J. Biol.

Chem. 240:1192-1197). Soffer and Leibowitz subsequently reconstituted the purified AaT enzyme and characterized its specificity for both the RNA and amino acid components of the donor molecule, demonstrating its use in transferring a non-natural amino acid, p-fluorophenylalanine (Leibowitz et al., 1969, Biochem. Biophys. Res. Commun. 36:47-53; Leibowitz, et al, 1971, J. Biol. Chem. 246; 5207-5212; FIG. 1A). Graciet and co-workers showed that BpT activity could also be functionally reconstituted in vitro (Graciet et al., 2006, Proc. Natl. Acad. Sci. USA 103:3078-3083).

Recently, purified AaT has been used to modify proteins in vitro with a variety of non-natural amino acids charged onto tRNAs, either by chemical semisynthesis or the use of a mutant aminoacyl tRNA synthetase (aaRS) (Ebhardt et al., 2009, Anal. Chem. 81:1937-1943; Taki et al., 2006, ChemBioChem 7:1676-1679; Taki et al., 2007, Biopolymers 88:263-271; Taki et al., 2008, ChemBioChem 9:719-722; Ebisu et al., 2009, ChemBioChem 10:2460-2464). Abramochkin and Shrader discovered that AaT was tolerant of variation in the acceptor stem (aminoacylation site) of the tRNA, and Sisido and co-workers showed that much shorter oligonucleotides can act as donors (Taki et 2008, ChemBioChem 9:719-722; Abramochkin et al., 1995, J. Biol. Chem. 270: 20621-20628; Abramochkin et al., 1996, J. Biol. Chem. 271: 22901-22907; for example in FIG. 1B, $R_n$=2-22 nucleotides). As part of their structural characterization of AaT, Tomita and co-workers found that AaT could bind phenylalanyl adenosine and transfer Phe to peptides in trace amounts (Watanabe et al, 2007, Nature 449:867-871). However, the use of adenosine mononucleoside as a donor substrate for AaT has not been further explored. No such exploration of donor scope has occurred for BpT.

There is thus a need in the art for methods of N-terminal modification that can be carried out easily under conditions that maintain protein folding without substantial prior protein manipulation. There is a further need in the art for methods of performing protein ligation, including ligation methods that are traceless in nature. The present invention addresses this unmet need in the art.

BRIEF SUMMARY OF THE INVENTION

The present invention provides a composition comprising at least one compound selected from the group consisting of 1a-1z, 2a, 3a-3z, 4a-4z, a salt thereof, and any combinations thereof.

The present invention also provides a method of derivatizing the N-terminus of a protein or peptide, the method comprising contacting a solution of the protein or peptide with a transferase and a derivative of a molecule, whereby the N-terminus of the protein or peptide is derivatized with the molecule.

In one embodiment, the method is carried out under conditions that do not significantly denature the protein or peptide.

In one embodiment, the solution is substantially free of a synthetase.

In one embodiment, the synthetase comprises aminoacyl tRNA synthetase.

In one embodiment, the derivative of the molecule is the adenosine ester of the molecule.

In one embodiment, the molecule comprises an amino acid.

In one embodiment, the amino acid comprises a compound selected from the group consisting of 4a-4z, a salt thereof and any combinations thereof.

In one embodiment, the amino acid is selected from the group consisting of cysteine, homocysteine, selenocysteine, selenohomocystein, a derivative thereof and any combinations thereof.

In one embodiment, the transferase is an aminoacyl tRNA transferase (AaT) or mutants thereof.

In one embodiment, the transferase comprises *E. coli* AaT, *V. vulnificus* BpT, a mutant thereof and any combinations thereof.

In one embodiment, the molecule comprises a detectable label.

In one embodiment, the detectable label is selected from the group consisting of a radioisotope, stable isotope, fluorophore, electron dense metals, biotin, DNA, RNA, antibody epitope, and any combinations thereof.

The present invention also provides a method of ligating a first protein and a second protein, comprising contacting a solution of the first protein with a transferase and a derivative of a protected amino acid, whereby the N-terminus of the protein is derivatized with the protected amino acid, yielding a derivatized first protein, wherein the amino acid is selected from the group consisting of cysteine, homocysteine, selenocysteine, selenohomocystein, a derivative thereof and any combinations thereof, further wherein the solution is substantially free of a synthetase, deprotecting the amino acid, whereby the N-terminus of the deprotected derivatized first protein comprises cysteine, homocysteine, selenocysteine, selenohomocystein, a derivatives thereof and any combinations thereof, and contacting the deprotected derivatized first protein with the second protein, wherein the C-terminus of the second protein comprises a thioester, whereby the deprotected derivatized first protein and the second protein undergo ligation to form a third protein.

In one embodiment, the amino acid is selected from the group consisting of selenocysteine, selenohomocystein, a derivative thereof and any combinations thereof.

In one embodiment, the third protein is further contacted with TCEP, whereby at least a portion of the seleno-containing amino acid residue is converted to alanine or homoalanine amino acid residue.

The present invention also provides a kit comprising a transferase, a derivative of a molecule or a salt thereof, and an instructional material for use thereof, wherein the instructional material comprises instructions for derivatizing the N-terminus of a protein or peptide, the method comprising contacting a solution of the protein or peptide with the transferase and the derivative of the molecule, whereby the N-terminus of the protein or peptide is derivatized with the molecule.

In one embodiment, the method is carried out under conditions that do not significantly denature the protein or peptide.

In one embodiment, the solution is substantially free of a synthetase.

In one embodiment, the synthetase comprises aminoacyl tRNA synthetase.

In one embodiment, the derivative of the molecule comprises the adenosine ester of the molecule.

In one embodiment, the molecule comprises an amino acid.

In one embodiment, the amino acid comprises a compound selected from the group consisting of 4a-4z, a salt thereof and any combinations thereof.

In one embodiment, the amino acid is selected from the group consisting of cysteine, homocysteine, selenocysteine, selenohomocystein, a derivative thereof and any combinations thereof.

In one embodiment, the transferase is an aminoacyl tRNA transferase (AaT) or mutants thereof.

In one embodiment, the transferase comprises *E. coli* AaT, *V. vulnificus* BpT, a mutant thereof and any combinations thereof.

In one embodiment, the molecule comprises a detectable label.

In one embodiment, the detectable label is selected from the group consisting of a radioisotope, stable isotope, fluorophore, electron dense metals, biotin, DNA, RNA, antibody epitope, and any combinations thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIGS. 1A-1B are a series of schemes depicting transferase-mediated N-terminal protein modification. FIG. 1A illustrates that fully enzymatic methods use aminoacyl tRNA synthetase (aaRS), tRNA, aminoacyltransferase (AaT), aminoacid, and ATP. FIG. 1B illustrates that chemoenzymatic methods use only a synthetic nucleic acid donor and AaT. As a non-limiting example, an aminoacyl mononucleoside ($R_n$=H) was used.

FIGS. 2A-2B are a series of schemes illustrating expressed protein ligation strategies.

FIG. 2A: Strategy 1—A protein fragment is expressed as a fusion to a "stalled" intein, and thioester exchange produces the protein as a thioester capable of undergoing ligation to a synthetic peptide with an N-terminal Cys, selenocysteine (Sec) or equivalent. The ligated product places the synthetic peptide at the C-terminus. Sec can be converted to Ala by treatment with TCEP (tris(carboxyethyl)phosphine) under mild conditions. Strategy 2—A protein fragment is expressed with a tag that can be proteolyzed to reveal an N-terminal Cys, which is then ligated to a synthetic peptide thioester. "Traceless" Ligation—A protein fragment is expressed with an N-terminal Lys, Arg, Asp, or Glu (generated by proteolysis, action of methionine aminopeptidase, or any other means known to those skilled in the art). A transferase (AaT recognizes Lys or Arg, BpT recognizes Asp or Glu) attaches a hemiselenide-protected amino acid such as C*sp (a protected Sec derivative). After ligation to a synthetic peptide, the protein is deselenized by treatment with TCEP, thus converting the ligation site to Ala.

FIG. 2B: Top—Protein Modification for Traceless Protein Ligation Reactions. Compounds 4j and 4k can be synthesized from Boc-protected amino acids as described herein, and then used to transfer a masked Cys or Sec to the protein N-terminus using Arg or Lys as the recognition element for AaT and Asp or Glu as the recognition element for BpT. Sec can then be used in a ligation with a thioester and then deselenized using tris(carboxyethyl)phosphine (TCEP) to form Ala, leaving any Cys in the protein intact. The right portion of the panel illustrates Sec transfer to N-terminus as part of a strategy to synthesize large semi-synthetic proteins. Bottom—Protein modification with AaT. The left portion of the panel illustrates modification of proteins with N-terminal Arg or Lys by aminoacyl adenosine donors. The right portion of the panel illustrates labeling of antibodies with arbitrary N-terminal sequences using mutant AaTs with alternate recognition sequences.

FIGS. 3A-3D are a series of reversed-phase HPLC traces for the analysis of AaT transferase reactions. FIGS. 3A-3C depict AaT-mediated transfer of Phe from adenosyl donor 4a to LysAlaAcm reporter peptide. HPLC chromatograms obtained after 0 h (FIG. 3A) or after 4 h (FIG. 3B) show conversion of LysAlaAcm (11.8 min retention time) to PheLysAlaAcm (13.0 min retention time). Conversion after one addition of donor 4a was 92% (FIG. 3B). A second addition of 1 mM 4a drives the reaction to completion with a small amount of double Phe addition as depicted in FIG. 3C. FIG. 3D depicts the results of HPLC analysis of transfer of Nap from adenosyl donor 4d to LysAlaAcm after 4 h shows conversion to NapLysAlaAcm (14.1 min retention time). Product identities were confirmed by observation of indicated masses by MALDI MS.

FIGS. 4A-4B are a series of images illustrating the results of kinetic analysis of AaT reactions. FIG. 4A depicts real time monitoring of Nap transfer to LysAlaAcm from 4d by quenching of Acm fluorescence. No significant inhibition was observed in the presence of 1 mM adenosine. FIG. 4B depicts saturation curve used to determine Michaelis-Menten kinetic parameters for LysAlaAcm modification by Phe donor 4a.

FIG. 5A shows an α-casein modification scheme. FIG. 5B is an image depicting PAGE gel analysis of α-casein modification. Lanes (left to right): (1) molecular weight (MW) markers (Masses in kDa: 17, 25, 30, 46, 58, 80, 175); (2) α-casein; (3) α-casein mixed with fluorescein alkyne (FlAlk); (4) α-casein mixed with FlAlk, $CuSO_4$, THPTA, and sodium ascorbate; (5) α-casein mixed with Azf-A (4c) and AaT; (6) α-casein mixed with 4c and AaT, then FlAlk; (7) α-casein mixed with 4c and AaT, then propargylamine (Alk), $CuSO_4$, tris-(3-hydroxypropyltriazolylmethyl)amine (THPTA), and sodium ascorbate; (8) α-casein mixed with 4c and AaT, then FlAlk, $CuSO_4$, THPTA, and sodium ascorbate; (9) MW markers; and (10) cell lysate labeling, α-casein reaction carried out using conditions of lane 8 with unpurified AaT in cleared *E. coli* lysate. FIG. 5C depicts the results of MALDI MS analysis of trypsinized N-terminal fragment of α-casein with or without modification by Azf using AaT and 4c (double addition).

FIGS. 6A-6D are a series of images depicting the results of reversed-phase HPLC analysis of AaT transferase reactions. FIGS. 6A-6C depict AaT-mediated transfer of Cys and Hcs from adenosyl donor 4k, 4l, or 4n to the LysAlaAcm reporter peptide. HPLC chromatograms obtained after 4 h show conversion of LysAlaAcm (11.3 min retention time) to CsmLysAlaAcm (FIG. 6A, 12.3 min retention time), CspLysAlaAcm (FIG. 6B, 13.0 min retention time), or HcmLysAlaAcm (FIG. 6C, 12.7 min retention time). FIG. 6D depicts the results of HPLC analysis of transfer of Hcm from adenosyl donor 4n to LysAlaAcm, deprotection, and ligation to the Ac-MetAspValPhe thioester peptide to form Ac-MetAspValPheHcsLysAlaAcm (17.7 min retention time). Product identities were confirmed by observation of indicated masses by MALDI MS.

FIGS. 8A-8B are a set of images depicting $^1H$ and $^{13}C$ NMR characterization of Boc-Azf-(DMT)-A 3c.

FIGS. 12A-12B are a set of images depicting $^1$H and $^{13}$C NMR characterization of Boc-N$_3$f-(DMT)-A 3g.

FIGS. 13A-13B are a set of images depicting $^1$H and $^{13}$C NMR characterization of Boc-Mcm-(DMT)-A 3h.

FIGS. 14A-14B are a set of images depicting $^1$H and $^{13}$C NMR characterization of Boc-Bzf-(DMT)-A 3i.

FIGS. 18A-18B are a series of images demonstrating fluorescence emission of NapLysAlaAcm solutions. FIG. 18A depicts fluorescence emission of mixtures of LysAlaAcm and NapLysAlaAcm (5d); $\chi_{5d}$=0.00, 0.10, 0.20, 0.25, 0.33, 0.50, 1.00. FIG. 18B depicts linear fit of normalized fluorescence vs. mole fraction NapLysAlaAcm (y=1−0.72x, R=0.999).

FIGS. 20A-20B are a series of images depicting the results of Edman degradation analysis of α-casein modification. FIG. 20A depicts the results of unmodified α-casein. R peak area was 196 counts total, F peak area was 44 counts. FIG. 20B depicts the results of Phe-modified α-casein. F peak area was 97 counts, R peak area was 53 counts.

FIGS. 21A-21B are a series of images demonstrating the results of PAGE gel analysis of α-casein modification in cleared E. coli lysate. FIG. 21A depicts the results of Coomassie-stained gel. FIG. 21B is a fluorescence image from 302 nm excitation. Lanes (left to right): 1) Molecular weight markers (Masses in kDa: 17, 25, 30, 46, 58, 80, 175); 2) Cleared lysate reacted with FlAlk; 3) Cleared lysate modified with 4c then reacted with FlAlk; 4) Cleared lysate with α-casein (0.012 mg) modified with 4c then reacted with FlAlk; 5) Cleared lysate with α-casein (0.12 mg) modified with 4c then reacted with FlAlk; 6) Molecular weight markers.

FIG. 22 is an image illustrating click chemistry reagents.

DETAILED DESCRIPTION OF THE INVENTION

Figure 2A:
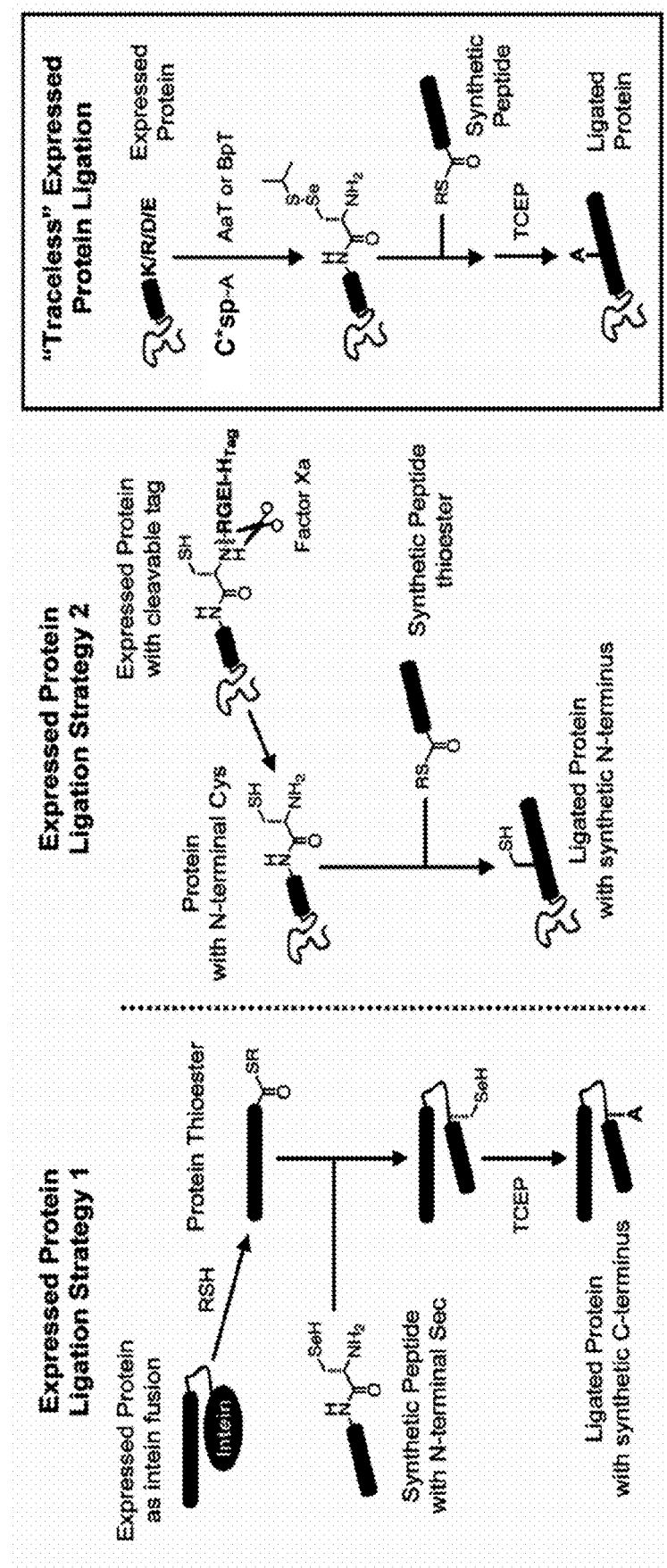
Figure 5A:
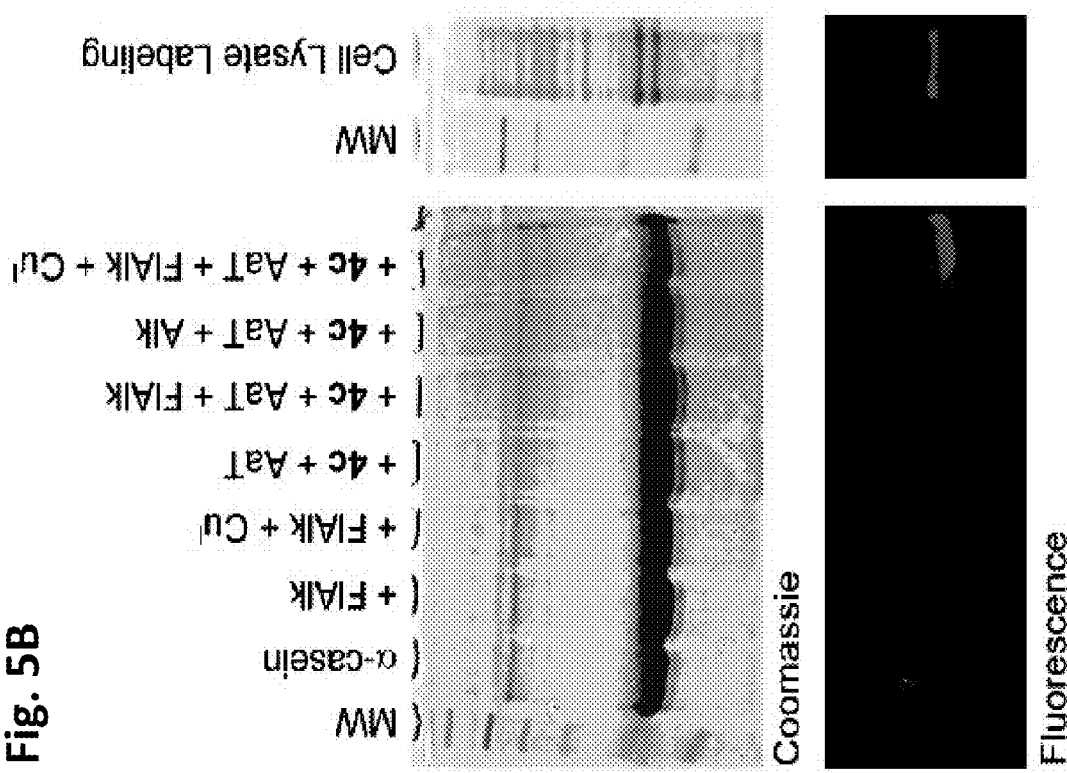
FIGS. 5A-5C are a series of images illustrating AaT-catalyzed modification and "Click" reaction of α-casein N-terminus.
Figure 5B:
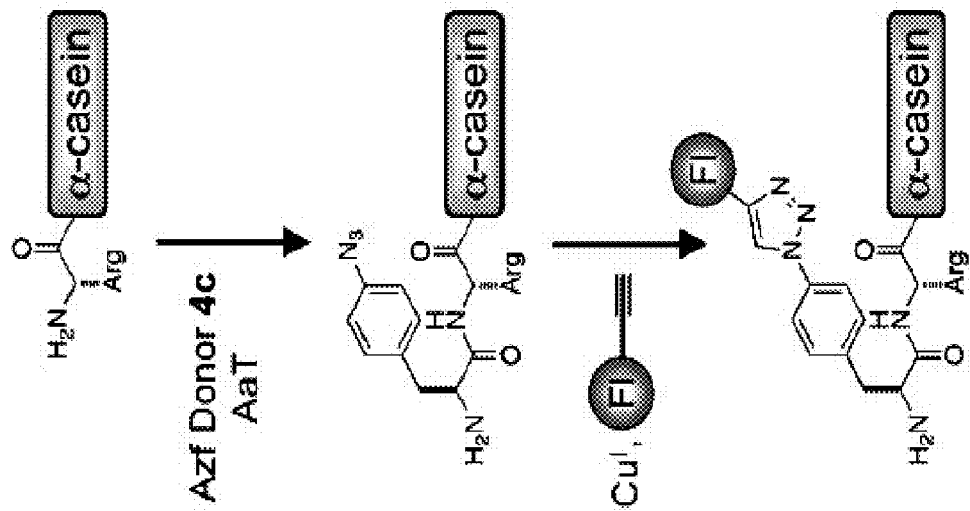
Figure 5C:
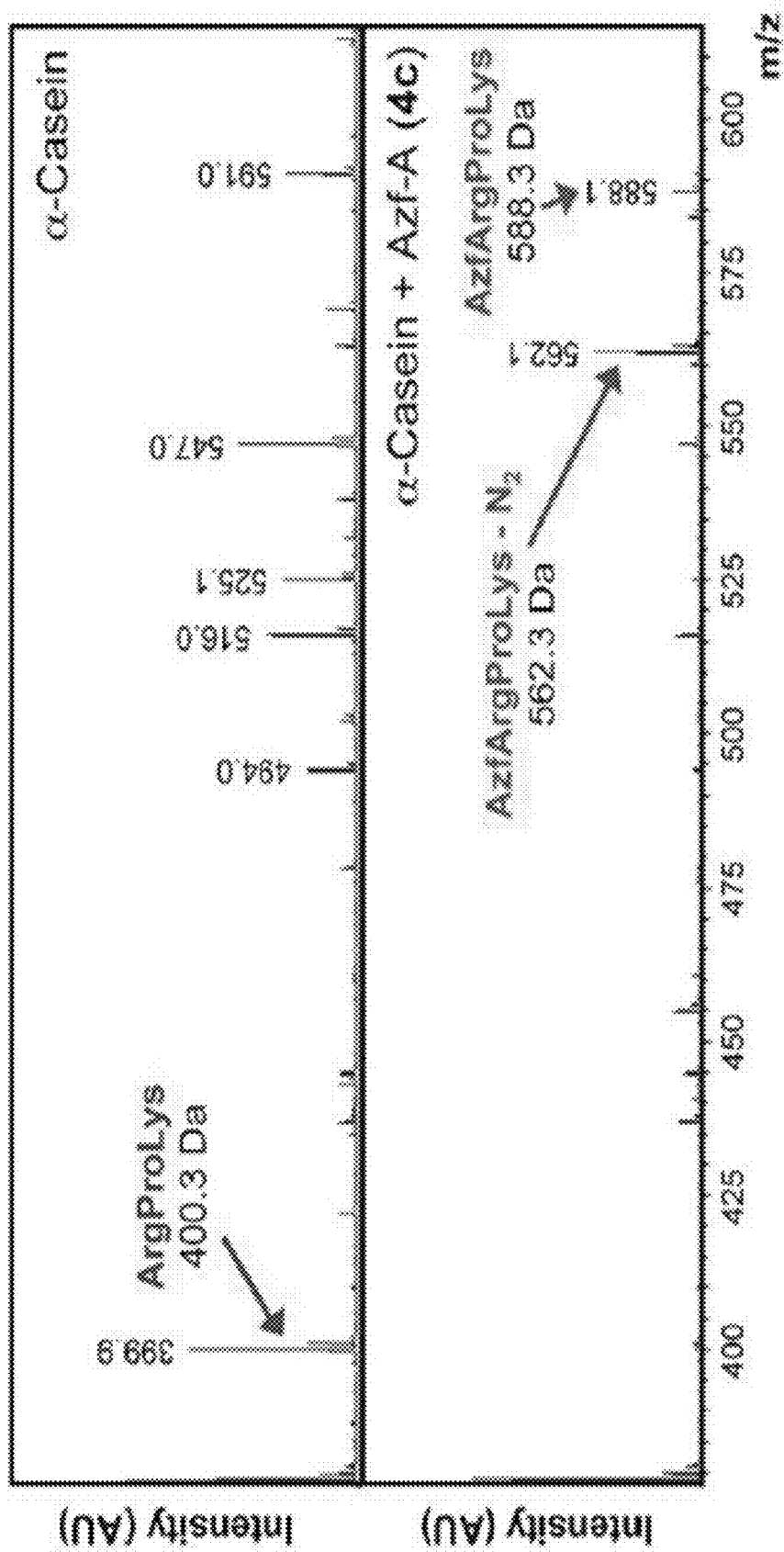

The present invention includes a chemoenzymatic method that allows for the modification of the N-terminus of a protein or peptide. The present invention also includes a chemoenzymatic method of conjugating a synthetic molecule to a protein or peptide via an N-terminal modification of the protein or peptide.

The method allows for N-terminus modification without requiring prior protein manipulation, under conditions that maintain the protein's natural fold and activity. Various non-natural amino acids may be transferred to the N-terminus of a protein with high efficiency at relatively low protein concentrations using the methods of the invention. In one embodiment, the amino acids are provided within the methods of the invention as easily synthesized adenosine esters thereof. In another embodiment, the synthetic molecule is a detectable label that allows for the identification and quantification of the protein.

In one embodiment, the N-terminal protein modification utilizes an enzyme and a derivative of the natural or non-natural amino acid. Preferably, the enzyme is a transferase. The transferase contemplated within the invention includes, but is not limited to, aminoacyl tRNA transferase from E. coli (AaT), V. vulnificus (BpT), mutants thereof, and any combination thereof. Preferably, the derivative is the adenosine ester of the natural or non-natural amino.

The present invention also includes a method of performing protein ligation of two or more proteins or peptides, wherein the N-terminus residue comprising a cysteine or selenocysteine residue is introduced in at least one protein or peptide using the chemoenzymatic method described herein. In one embodiment, the protein ligation is traceless, wherein the N-terminus residue incorporated in the ligated protein is chemically modified into a natural amino acid.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "MALDI MS" refers to matrix-assisted laser desorption/ionization mass spectrometry.

As used herein, the term "thioester" refers to the group C(=O)—S—.

As used herein, the term "ligation" as applied to two or more molecules refers to the process to creating covalent chemical bonds among the two or more molecules, as to form at least one molecule that incorporates at least a portion of each of the two or more molecules.

The term "abnormal" when used in the context of organisms, tissues, cells or components thereof refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

As used herein, the term "amino acid" refers to any natural or non-natural compound having a carboxyl group and an amino group in a molecule.

An "amino acid" as used herein is meant to include both natural and synthetic amino acids, and both D and L amino acids. "Natural amino acid" means any of the twenty L-amino acids commonly found in naturally occurring peptides. "Non-natural amino acid residues" means any amino acid, other than the standard amino acids, regardless of whether it is prepared synthetically or derived from a natural source. As used herein, "synthetic amino acid" encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

As used herein, natural amino acids are represented by the full name thereof, by the three letter code corresponding thereto, or by the one-letter code corresponding thereto, as indicated below:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "labeled amino acid" refers to an amino acid that is bound to a label compound.

The "amino acid skeleton" used herein includes a carboxyl group, an amino group, and a portion connecting them in an amino acid.

The term "aromatic ring" used herein generally refers to every type of unsaturated cyclic compound. Accordingly, it includes a 5- or 6-membered heteroaromatic ring and a polycyclic compound comprising 2 or more, preferably 2 to 5, and more preferably 2 or 3 cyclic structures. A particularly preferable aromatic ring is a benzene ring. Among naturally-occurring amino acids, phenylalanine, tryptophan, and tyrosine are naturally-occurring aromatic amino acids comprising aromatic rings on their side chains. A preferable example of the labeled amino acid of the present invention is a labeled compound in which a label compound is bound to the aromatic ring.

As used herein, an "instructional material" includes a publication, a recording, a diagram, or any other medium of expression that can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container that contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

A "label" or "detectable label" or "tag" is a composition detectable by mass spectrometric, spectroscopic, photochemical, biochemical, immunochemical, or chemical means. For example, useful labels include radioactive isotopes (e.g., $^3$H, $^{35}$S, $^{32}$P, $^{51}$Cr, or $^{125}$I), stable isotopes (e.g., $^{13}$C, $^{15}$N, or $^{18}$O), fluorescent dyes, electron-dense reagents, enzymes (e.g., alkaline phosphatase, horseradish peroxidase, or others commonly used in an ELISA), biotin, digoxigenin, or haptens or epitopes and proteins for which antisera or monoclonal antibodies are available. In general, a label as used in the context of the present invention is any entity that may be used to detect or isolate the product of interest. Thus, any entity that is capable of binding to another entity may be used in the practice of this invention, including without limitation, epitopes for antibodies, ligands for receptors, and nucleic acids, which may interact with a second entity through means such as complementary base pair hybridization.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups).

The term "polypeptide" as used herein is defined as a chain of amino acid residues, usually having a defined sequence. As used herein the term polypeptide is mutually inclusive of the terms "peptide" and "protein". "Polypeptide" also refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

A "peptide ester" refers generally to any peptide in which one carboxyl group of the peptide is esterified, i.e., is of the structure C(=O)—O—R. In embodiments of this invention, a peptide ester can serve as a substrate such that the peptide is added to the alpha-amino group of polypeptides to form the structure C(=O)—NH—R, thus labeling the polypeptide. In one embodiment, a peptide ester can carry a detectable label and a site for proteolysis or another form of chemical cleavage (e.g., through introduction of photolabile, acid-labile, or base-labile functional groups).

Conventional notation is used herein to portray polypeptide sequences: the left-hand end of a polypeptide sequence is the amino-terminus; the right-hand end of a polypeptide sequence is the carboxyl-terminus.

"Proteases" (or "proteinases", "peptidases", or "proteolytic" enzymes) generally refer to a class of enzymes that cleave peptide bonds between amino acids of proteins. Because proteases use a molecule of water to effect hydrolysis of peptide bonds, these enzymes can also be classified as hydrolases. Six classes of proteases are presently known: serine proteases, threonine proteases, cysteine proteases, aspartic acid proteases, metalloproteases, and glutamic acid proteases (see, e.g., Barrett A. J. et al., The Handbook of Proteolytic Enzymes, $2^{nd}$ ed. Academic Press, 2003). Proteases are involved in a multitude of physiological reactions from simple digestion of food proteins to highly regulated cascades (e.g., the cell cycle, the blood clotting cascade, the complement system, and apoptosis pathways). It is well known to the skilled artisan that proteases can break either specific peptide bonds, depending on the amino acid sequence of a protein, or break down a polypeptide to constituent amino acids.

The terms "patient," "subject," "individual," and the like are used interchangeably herein, and refer to any animal, or cells thereof whether in vitro or in situ, amenable to the methods described herein. In a non-limiting embodiment, the patient, subject or individual is a human.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition described herein, including alleviating symptoms of such diseases.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention includes a chemoenzymatic method of modifying a protein or peptide at the N-terminus, thus allowing for the labeling and/or introduction of at least one additional amino acid residue at the N-terminus of the protein or peptide. In one embodiment, the method utilizes a nucleoside-based amino acid donor in combination with a transferase, whereby the transferase transfers the non-natural or natural amino acid from the donor to the N-terminus of the protein to yield a N-terminus modified protein. In another embodiment, the N-terminus modification of the protein may be further manipulated to further comprise a detectable label.

In one aspect, the present invention relates to the discovery that natural or non-natural amino acids may be transferred from adenosine donors to the N-terminus of proteins (or peptides) with high yields at relatively low protein concentrations. The methods of the invention afford high yields under non-denaturing conditions. The transferase useful within the method requires only a single amino acid on the protein for specific recognition. In one embodiment, the single amino acid recognized by the transferase is charged.

The methods of the invention are also useful in the context of protein ligation. For example, the chemoenzymatic method of the invention may be used to introduce a specific residue (such as cysteine, homocysteine, selenocysteine, or a derivative thereof) on the N-terminus of a protein. This specific residue may then be used in a protein ligation reaction, thus resulting in a larger product protein. In one embodiment, the homocysteine residue incorporated in the product protein is methylated to yield a methionine residue. In another embodiment, the selenocysteine residue incorporated in the product protein is converted to alanine.

This invention includes methods for synthetically manipulating protein structures. For example, AaT can efficiently use a minimal adenosine substrate, which can be synthesized in one to two steps, as the source of the natural or non-natural aminoacid. Accordingly, the invention includes adenosyl donors and the use of these donors in AaT-catalyzed protein modifications.

In a non-limiting embodiment, the use of adenosyl amino acid donors offers an advantage over the prior art by removing the substrate limitations associated with synthetases, and avoiding the complex synthesis of an oligonucleotide donor. Thus, the use of AaT donors within the invention increases the potential substrate scope and reaction scale for N-terminus protein modification, without resorting to conditions that promote protein unfolding.

As demonstrated herein, the aminoacyl tRNA transferases from Escherichia coli (AaT) and V. vulnificus (BpT) can modify the N-terminus of a protein with an amino acid from a tRNA or a synthetic oligonucleotide donor. The results presented herein demonstrate that AaT can efficiently use a minimal adenosine substrate, which can be synthesized in one to two steps from readily available starting materials. The enzymatic activity of AaT with aminoacyl adenosyl donors has been characterized and it has been found that the reaction products do not inhibit AaT. The use of adenosyl donors removes the substrate limitations imposed by the use of synthetases for tRNA charging and avoids the complex synthesis of an oligonucleotide donor. Thus, the present AaT donors increase the potential substrate scope and reaction scale for N-terminal protein modification under conditions that maintain folding.

In another aspect, the results presented herein demonstrate that AaT can efficiently use an aminoacyl adenosine substrate to transfer disulfide-protected Cys analogs, which can be used in subsequent peptide ligation reactions. These Cys analogs can then be converted to other amino acids, making the ligation "traceless." For example, Hcs-based analogs can be converted to Met by alkylation. The scope of molecules transferred thus far indicates that a variety of analogs including Sec derivatives should be transferable, allowing the ligation site to be masked as other amino acids, including Ala, Leu, Phe, and Ile. This effectively removes the requirement of Cys at the peptide ligation site of an expressed protein fragment.

Compositions

The invention includes a composition comprising at least one compound selected from the group consisting of 1a-1z, 2a, 3a-3z, 4a-4z, a salt thereof, and any combinations thereof. The structures of compounds 1a-1z, 2a, 3a-3z, and 4a-4z are depicted in Scheme 1 disclosed elsewhere herein.

Methods

The invention includes a method of derivatizing the N-terminus of a protein or peptide. The method comprises contacting a solution of the protein or peptide with a transferase and a derivative of a molecule, whereby the N-terminus of the protein or peptide is derivatized with the molecule.

In one embodiment, the method is carried out under conditions that do not significantly denature the protein or peptide. In another embodiment, the solution is substantially free of a synthetase. In yet another embodiment, the synthetase comprises aminoacyl tRNA synthetase. In yet another embodiment, the derivative of the molecule is the adenosine ester of the molecule. In yet another embodiment, the molecule comprises an amino acid. In yet another embodiment, the amino acid comprises a compound selected from the group consisting of 4a-4z, a salt thereof and any combinations thereof. In yet another embodiment, the amino acid is selected from the group consisting of cysteine, homocysteine, selenocysteine, selenohomocystein, a derivative thereof and any combinations thereof. In yet another embodiment, the transferase is an aminoacyl tRNA transferase (AaT) or mutants thereof. In yet another embodiment, the transferase comprises *E. coli* AaT, *V. vulnificus* BpT, a mutant thereof and any combinations thereof. In yet another embodiment, the molecule comprises a detectable label. In yet another embodiment, the detectable label is selected from the group consisting of a radioisotope, stable isotope, fluorophore, electron dense metals, biotin, DNA, RNA, antibody epitope, and any combinations thereof. In one embodiment, the molecule comprises a photoinducible cross linker.

The invention further includes a method of ligating a first protein and a second protein. The method comprises contacting a solution of the first protein with a transferase and a derivative of a protected amino acid, whereby the N-terminus of the protein is derivatized with the protected amino acid, yielding a derivatized first protein; wherein the amino acid is selected from the group consisting of cysteine, homocysteine, selenocysteine, selenohomocystein, a derivative thereof and any combinations thereof; further wherein the solution is substantially free of a synthetase. The invention further comprises deprotecting the amino acid, whereby the N-terminus of the deprotected derivatized first protein comprises cysteine, homocysteine, selenocysteine, selenohomocystein, a derivatives thereof and any combinations thereof. The invention further comprises contacting the deprotected derivatized first protein with the second protein, wherein the C-terminus of the second protein comprises a thioester; whereby the deprotected derivatized first protein and the second protein undergo ligation to form a third protein.

In one embodiment, the amino acid is selected from the group consisting of selenocysteine, selenohomocystein, a derivative thereof and any combinations thereof. In another embodiment, the third protein is further contacted with TCEP, whereby at least a portion of the seleno-containing amino acid residue is converted to alanine or homoalanine amino acid residue.

Kits

The invention includes a kit comprising a transferase, a derivative of a molecule or a salt thereof, and an instructional material for use thereof. The instructional material comprises instructions for derivatizing the N-terminus of a protein or peptide, the method comprising contacting a solution of the protein or peptide with the transferase and the derivative of the molecule, whereby the N-terminus of the protein or peptide is derivatized with the molecule.

In one embodiment, the method is carried out under conditions that do not significantly denature the protein or peptide. In another embodiment, the solution is substantially free of a synthetase. In yet another embodiment, the synthetase comprises aminoacyl tRNA synthetase. In yet another embodiment, the derivative of the molecule comprises the adenosine ester of the molecule. In yet another embodiment, the molecule comprises an amino acid. In yet another embodiment, the amino acid comprises a compound selected from the group consisting of 4a-4z, a salt thereof and any combinations thereof. In yet another embodiment, the amino acid is selected from the group consisting of cysteine, homocysteine, selenocysteine, selenohomocystein, a derivative thereof and any combinations thereof. In yet another embodiment, the transferase is an aminoacyl tRNA transferase (AaT) or mutants thereof. In yet another embodiment, the transferase comprises *E. coli* AaT, *V. vulnificus* BpT, a mutant thereof and any combinations thereof. In yet another embodiment, the molecule comprises a detectable label. In yet another embodiment, the detectable label is selected from the group consisting of a radioisotope, stable isotope, fluorophore, electron dense metals, biotin, DNA, RNA, antibody epitope, and any combinations thereof.

Synthesis of Adenosyl Amino Acid Donor

The synthesis of adenosyl amino acid donor compounds may be carried out on any natural or non-natural amino acid with appropriate acid-labile protecting groups (e.g., N-Boc). Acid-labile protecting groups include, but are not limited to, tert-butyloxycarbonyl, tert-butyl ester and 2-phenylisopropyl ester.

Scheme 1 exemplifies a non-limiting method of preparing adenosyl donors useful within the invention. 5'-DMT-protected adenosine may be reacted with a cyanomethyl ester (1a-1z) or a succinate ester (2a) to yield acylated adenosine derivative (3a-3z). Deprotection of (3a-3z) with TFA yields adduct (4a-4z). This adduct, which acts as the reaction donor in the N-terminal modification reaction, may be reacted with a peptide substrate (containing a N-terminus free amino group) in the presence of the aminoacyl transferase to yield the product (5a-5z).

Labeling of N-Termini of Polypeptides

A label compound may be bound directly or via a spacer to any functional group, such as an amino, thiol, carboxyl, hydroxyl, aldehyde, allyl, or halogenated alkyl group of a natural or non-natural amino acid. Examples of substances that may be used as reagents for labeling amino groups include a succinimide ester, isothiocyanate, sulfonyl chloride, NBD-halide, and dichlorotriazine. Examples of substances that may be used as reagents for labeling thiol groups include an alkyl halide, maleimide, and aziridine. Examples of substances that may be used as reagents for labeling carboxyl groups include a diazomethane compound, aliphatic bromides, and carbodiimide. For example, succinimide ester is introduced to a label compound directly or via a spacer; on the other hand, an amino group is introduced to an aromatic ring of an amino acid, and then the amino acid and the label compound can be bound to each other by means of amide bonds. An example of an amino acid comprising an aromatic ring to which an amino group has been introduced is aminophenylalanine. A functional group used in such a case may be suitably selected and introduced, and a binding method can also be suitably selected. In this case, forming the amide bond at about pH 5 enables selective reaction with an amino group on the side chain of aminophenylalanine, even if another amino group is present in the amino acid molecule. Alternatively, another amino group may be protected with Boc or the like, and the protecting group can be removed after the reaction of amino group on the side chain.

The labeled amino acid of the present invention has properties of its label substance. Accordingly, desired functions can be imparted to the labeled amino acid through the selection of a label compound having desired functions. A variety of label moieties can be used to incorporate into proteins and polypeptides, including affinity handles (e.g., biotin), immunoprobes, isotopic labels, heavy-atom derivatives, PEG moieties, fluorescein derivatives, and other non-natural constituents. The skilled artisan will recognize that this is not an exhaustive list, as for instance, any detectable label that can be incorporated into a substrate (e.g., biotin labeled peptide esters) to be used to label a free N-terminus (e.g., alpha-amino group of a polypeptide generated through proteolysis) may be used.

Among label compounds, fluorescent substances have particularly high usefulness as labels for a protein. Further, a luminescent substance in the visible light range can be detected by a detector extensively and commonly used. Furthermore, a variety of highly sensitive detectors have already been developed and extensively used. These fluorescent substances are very useful as label compounds for labeling cells or the like since they are not affected by interferential actions caused by fluorescence emission in cells.

Additional examples of the label compound that is used in the present invention include a dye compound, a fluorescent substance, a chemi- or bioluminescent substance, an enzyme substrate, a coenzyme, an antigenic substance, and a protein-binding substance that are known to persons skilled in the art. Examples of fluorescent substances that can be used in the present invention include all known fluorescent substances including rhodamine, fluorescein (FITC), Texas Red, acridine orange, SYBR Green, Cy3, Cy5, a BODIPY compound, and a derivative thereof.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, gamma-phthalaldehyde, fluorescamine and the like are all exemplary fluorescent labels. Chemiluminescent labels, i.e., labels that are capable of converting a secondary substrate to a chromogenic product, are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, alpha-glycerophosphate dehydrogenase, triose phosphate isomerase, asparaginase, glucose oxidase, beta-galactosidase, ribonuclease, urease, catalase, glucoamylase, acetylcholinesterase, luciferin, luciferase, aequorin and the like are all exemplary protein-based chemiluminescent labels. Luminol, isoluminol, theromatic acridinium ester, imidazole, acridinium salt, oxalate ester and the like are exemplary non-protein-based chemiluminescent labels. Another non-limiting and commonly used example of an indirectly detectable label is an affinity ligand, i.e., a label with strong affinity for a secondary binding partner (e.g., an antibody or aptamer), which may itself be directly or indirectly detectable.

In general, a detectable label may be visualized or detected in a variety of ways, with the particular manner of detection being selected based on the particular detectable label, where representative detection means include, e.g., scintillation counting, autoradiography, measurement of paramagnetism, fluorescence measurement, light absorption measurement, measurement of light scattering and the like.

In one embodiment, a pre-conjugated label may contain one or more reactive moieties (e.g., carboxyl or reactive ester, amine, hydroxyl, aldehyde, sulfhydryl, maleimidyl, alkynyl, azido, etc. moieties). As discussed elsewhere herein, these reactive moieties may, in certain embodiments, facilitate the conjugation process. Specific examples include peptidic labels bearing alpha-terminal amine and/or epsilon-amine lysine groups. It will be appreciated that any of these reactive moieties may be artificially added to a known label if not already present. For example, in the case of peptidic labels, a suitable amino acid (e.g., a lysine) may be added or substituted into the amino acid sequence. In addition, it will be appreciated that the conjugation process may be controlled by selectively blocking certain reactive moieties prior to conjugation.

Detection of Labeled Polypeptides

After the labeling reaction, any method that allows the detection of labeled polypeptides may be used to identify, isolate, or analyze the labeled polypeptides. For example, the skilled artisan will recognize that alpha-amino groups of polypeptides labeled with a peptide ester containing a biotin label can be isolated or detected using avidin-related proteins such as avidin itself, streptavidin, and neutravidin. Thus, neutravidin beads may be used to isolate biotin labeled polypeptides from complex mixtures or streptavidin linked to horseradish peroxidase may be used to identify biotin labeled polypeptides after protein separation by a procedure such as electrophoresis and avidin blotting.

Alternatively, methods such as mass spectrometry may be used to identify peptides that are labeled following proteolysis. As understood generally by those skilled in the art, mass spectrometry is an analytical technique used to measure the mass-to-charge ratio of gaseous ions. It can be used to determine the composition of a biological sample by generating a mass spectrum representing the masses of sample components such as peptides and proteins. It can additionally be used to determine the structure of components in mixtures by observing the fragmentation of each peptide or protein present in the sample.

For the analysis of proteins and peptides, the two primary methods for ionization of samples are used: electrospray ionization (ESI) and matrix-assisted laser desorption/ionization (MALDI). In one method of analysis, intact proteins are ionized by either of the two techniques described elsewhere herein, and then introduced directly to a mass analyzer. In a second method, proteins are enzymatically digested into smaller peptides using an agent such as trypsin or pepsin. The collection of peptide products is then introduced to the mass analyzer.

The labeled proteins and polypeptides of the present invention can be part of a very complex mixture of other proteins, polypeptides, and molecules that coexist in a biological medium such as a cell extract. Accordingly, it may be desirable f to further purify the labeled proteins or polypeptides of the invention prior to analysis by mass spectrometry. Any method known in the art for the separation of proteins and polypeptides may be used to accomplish this goal. Among these methods are one- and two-dimensional gel electrophoresis of proteins, varying dimensions of liquid chromatography of proteins or polypeptides and HPLC. If the label used is an affinity label, a resin comprising a moiety that binds to the affinity label may be used to isolate labeled proteins and polypeptides. For example, if biotin is used as a label, neutravidin beads may be used to isolate proteins and polypeptides resulting from proteolysis that have been labeled with peptide esters containing a biotin moiety.

In general, the data generated from mass spectrometry analyses (e.g., MS/MS peak lists) can be compared to sequence databases using computer programs available to the skilled artisan to determine the identity of labeled proteins. In some cases, labeled or modified peptides can be readily identified in MS/MS data by the presence of characteristic N-terminal modifications, such as characteristic di-peptide modifications.

"Traceless" Expressed Protein Ligation

The synthesis of chemically-modified proteins is a valuable tool for the study of their function. One of the most enabling technologies in this area is native chemical ligation, in which a peptide (or protein) thioester is reacted with a peptide (or protein) bearing an N-terminal Cys to form a native amide bond. This is a powerful approach, and as shown in FIG. 2A, Strategy 1, the use of intein constructs has allowed one to generate the thioester fragment from proteins expressed in *E. coli* so that a relatively small synthetic peptide with N-terminal Cys can be used to prepare a large semi-synthetic protein with a C-terminal chemical modification. Likewise as shown in FIG. 2A, Strategy 2, a protein can be expressed with an N-terminal Cys and reacted with a synthetic thioester, yielding a semi-synthetic protein with an N-terminal chemical modification. These modifications may include non-natural amino acids with useful fluorescent or chemical properties and segmental isotopic labeling for infrared (IR), nuclear magnetic resonance (NMR or MRI), and positron emission tomography (PET) imaging. This approach may also be used to semi-synthesize proteins with homogeneous post-translational modifications such as glycosylation.

The major limitation of existing semi-synthesis strategies is that Strategy 2 requires an N-terminal Cys from the expressed protein portion. This can be avoided in Strategy 1 by using non-natural amino acids such as selenocysteine (Sec), which can be converted to Ala by treatment with TCEP, making the ligation "traceless."

According to the methods described herein, the transferase enzymes AaT and BpT may deliver an amino acid like C*sp (a protected Sec derivative) to the protein N-terminus, whereby it can be used in ligation and then deselenized using TCEP (FIG. 2A). This approach allows the implementation of traceless ligation on expressed proteins. In one embodiment, analogs of Sec which are deselenized to generate other natural amino acids at the ligation site may be developed. Additionally, homocysteine (Hcs) can be added to the N-terminus, used as a ligation handle, and then converted to Met by alkylation. Use of Sec and Hcs removes a major remaining barrier to the widespread adoption of this technique in biochemical research, giving the researcher complete freedom in their choice of ligation site for their synthetic fragment. Ideally, this approach could be combined with intein usage to generate internally labeled proteins with a minimum of peptide synthesis. For example, as indicated in the FIG. 2A, "Traceless" Ligation, only synthesis of the adenosyl donor is required, wherein the C-terminal and N-terminal fragments could be expressed in cells.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods

Chloroacetonitrile, N,N-diisopropylethylamine (DIPEA), 5'-O-(4,4'-Dimethoxytrityl) adenosine ((DMT)-A), tetrabutylammonium acetate (TBAAc), trifluoroacetic acid (TFA), and triisopropyl silane (TIPSH) were purchased from Sigma-Aldrich (St. Louis, Mo.).

DMT-A, previously available from Sigma-Aldrich, may be obtained from ChemGenes Corporation (Wilmington, Mass.). It was additionally synthesized following the protocol outlined by Ogilvie et al (Ogilvie et al., 1967, J Org Chem 32:2365-2366).

N-Boc-L-phenylalanine-O-succinimide (Boc-Phe-OSu) and Lysylalanylaminomethylcoumarin (LysAlaAcm) were purchased from Bachem (Torrence, Calif.). N-Boc-L-phenylalanine (Boc-Phe-OH) and all solvents were purchased from Fisher Scientific (Pittsburgh, Pa.). All deuterated solvents were purchased from Cambridge Isotopes Laboratories, Inc. (Andover, Mass.).

*E. coli* BL21(DE3) cells were purchased from Strata-gene (La Jolla, Calif.). The pEG6 plasmid, containing His10-tagged *E. coli* AaT was obtained, Sequencing-grade trypsin was purchased from Promega (Madison, Wis.). All other reagents were purchased from Fisher Scientific (Pittsburgh, Pa.).

Milli-Q filtered (18 MΩ) water was used for all aqueous solutions (Millipore; Billerica, Mass.). Matrix-assisted laser desorption ionization (MALDI) mass spectra were collected using a Bruker Ultraflex III MALDI-TOF-TOF mass spectrometer (Billerica, Mass.), UV absorbance spectra were obtained with a Hewlett-Packard 8452A diode array spectrophotometer (currently Agilent Technologies; Santa Clara, Calif.). Donor molecule purification was conducted on a Bio- Cad Sprint FPLC, (GMI Inc.; Ramsey, Minn.; originally from Perseptive Biosystems) with a Waters Sunfire Prep C18-prep OBD column, 5 µm, 117×150 mm (Milford, Mass.).

Analytical HPLC assays were performed on an Agilent 1100 HPLC using a Waters Symmetry Shield C18 column, NMR spectra, $^1$H and $^{13}$C, were collected with a Bruker DRX 500 MHz instrument. "Low resolution" electrospray ionization (ESI) mass spectra (LRMS) were obtained on a Waters Acquity Ultra Performance LC connected to a single quadrupole detector (SQD) mass spectrometer, "High resolution" ESI mass spectra (HRMS) were obtained on a Waters LCT Premier XE LC/MS. DNA sequencing was performed at the University of Pennsylvania DNA sequencing facility. Fluorescence spectra were collected with a Varian Cary Eclipse fluorescence spectrophotometer fitted with a Peltier multicell holder (currently Agilent Technologies).

N-Boc-L-leucine (Boc-Leu-OH), N-Boc-L-p-azidophenylalanine (Boc-Azf-OH), N-Boc-L-naphthylalanine (Boc-Nap-OH), N-Boc-, N-Me-L-phenylalanine (Boc-Mef-OH), N-Acetyl-L-phenylalanine (Acf-OH), and N-Fmoc-methoxycoumarinylalanine (Fmoc-Mcm-OH) were purchased from Bachem (Torrence, Calif.).

All solvents were purchased from Fisher Scientific (Pittsburgh, Pa.). QuikChange® site-directed mutagenesis kits were purchased from Stratagene (La Jolla, Calif.). DNA oligomers were purchased from Integrated DNA Technologies, Inc. (Coralville, Iowa). Bradford reagent assay kits were purchased from BioRAD (Hercules, Calif.). Protease inhibitor cocktail was purchased from Sigma-Aldrich (St. Louis, Mo.). All other reagents were purchased from Fisher Scientific (Pittsburgh, Pa.). Infrared spectra were recorded on a Nicolet 6700 FT-IR instrument.

Donor (4a-4z) Synthesis

As described elsewhere herein, the carboxy-terminus of the amino acid (or analog) was activated as a cyanomethyl ester using chloroacetonitrile to yield 1b-1z. Next, the protected amino acid was attached to one of the available hydroxyls (2'-OH or 3'-OH) of DMT-A. The resulting protected adenylate (3b-3z) was deprotected using a 50/50 solvent mixture of trifluoroacetic acid and THF (1 mL) or neat TFA (1 mL) with TIPSH present as a scavenger, stirred for 24 h, concentrated under reduced pressure, extracted using DCM and water as mentioned elsewhere herein, and HPLC purified. The final product, deprotected adenylate (4b-4z), was purified via C18 column purification using an HPLC.

(S)-Cyanomethyl 2-((tert-butoxycarbonynamino)-3-phenylpropanoate (Boc-Phe-OCH$_2$CN, 1a)

Boc-Phe-OH (2.01 g, 7.57 mmol) was dissolved in 10 mL tetrahydrofuran under ambient conditions, Ten equivalents of chloroacetonitrile (4.78 mL, 75.4 mmol) and 1.1 equiv of DIPEA (8.30 mmol, 1.45 mL) were added to the reaction mixture and allowed to stir overnight. 1a was purified on silica gel (20% EtOAc in hexanes) to yield 2.474 g (100%) of a pale-yellow oil after evaporation. R$_f$ 0.4 in 20% EtOAc in hexanes; $^1$H NMR (500 MHz, CDCl$_3$): δ 7.26 (t, J=7.0 Hz, 2H), 7.20 (t, J=7.1 Hz, 1H), 7.11 (d, J=7.3 Hz, 2H), 5.11 (d, J=7.8 Hz, 1H), 4.69-4.57 (m, 311), 3.09-2.98 (m, 211), 1.36 (s, 911); $^{13}$C NMR (125 MHz, CDCl$_3$) δ 170.8, 155.1, 135.4, 129.2, 128.7, 127.3, 114.0, 80.9, 80.2, 54.4, 48.8, 37.8, 28.2; HRMS (ESI) calcd m/z for C$_{16}$H$_{20}$N$_2$O$_4$Na [M+Na]$^+$ 327.132. found 327.133.

(S)-cyanomethyl 2-((tert-butoxycarbonyl)amino)-4-methylpentanoate (Boc-Leu-OCH$_2$CN, 1b)

Chloroacetonitrile (5 mL) and DIPEA (160 mg, 0.21 mL, 1.2 mmol) were added to Boc-Leu-OH (252 mg, 1.09 mmol) and stirred for 12 h. The solvent was removed under reduced pressure and SiO$_2$ flash chromatography (20% ethyl acetate in hexanes) afforded 284 mg of a pale yellow oil in 96% yield. R$_f$ 0.5 in 20% ethyl acetate in hexanes. $^1$H NMR (500 MHz, CDCl$_3$): δ 5.00 (d, J=7.7 Hz, 1H), 4.80-4.65 (m, 2H), 4.30-4.29 (m, 1H), 1.70-1.65 (m, 1H), 1.60-1.47 (m, 2H), 1.39 (s, 9H), 0.91-0.89 (m, 6H); $^{13}$C NMR (125 MHz, CDCl$_3$): δ 172.2, 155.5, 114.21, 80.3, 53.2, 52.0, 41.0, 28.3, 24.8, 22.8, 21.7; HRMS (ESI) m/z calcd for C$_{13}$H$_{22}$N$_2$O$_4$Na [M+Na]$^+$ 293.147. found 293.151.

(S)-cyanomethyl 3-(4-azidophenyl)-2-((tert-butoxycarbonyl)amino)propanoate (Boc-Azf-OCH$_2$CN, 1c)

Chloroacetonitrile (5 mL) and DIPEA (99 mg, 0.13 mL, 0.76 mmol) were added to Boc-Azf-OH (212 mg, 0.691 mmol) and stirred for 12 h. The solvent was removed under reduced pressure and SiO$_2$ flash chromatography (30% ethyl acetate in hexanes) afforded 230 mg of a pale yellow oil in 96% yield. R$_f$ 0.5 in 30% ethyl acetate in hexanes; $^1$H NMR (500 MHz, CDCl$_3$): δ 7.13 (d, J=8.3 Hz, 2H), 6.97 (d, J=8.4 Hz, 2H), 5.00 (d, J=7.7 Hz, 1H), 4.80-4.65 (m, 2H), 4.62-4.58 (m, 1H), 3.12-3.01 (m, 2H), 1.40 (s, 9H); $^{13}$C NMR (125 MHz, CDCl$_3$): δ 170.7, 155.1, 139.4, 132.0, 130.7, 119.5, 114.0, 80.7, 54.4, 49.0, 37.5, 28.3; HRMS (ESI) m/z calcd for C$_{16}$H$_{19}$N$_5$O$_4$Na [M+Na]$^+$ 368.133. found 368.135.

(S)-cyanomethyl 2-((tert-butoxycarbonyl)amino)-3-(naphthalen-2-yl)propanoate (Boc-Nap-OCH$_2$CN, 1d)

Chloroacetonitrile (2.5 mL) and DIPEA (25 mg, 33 µL, 0.19 mmol) were added to Boc-NapAla-OH (54.8 mg, 0.174 mmol) and stirred for 12 h. The solvent was removed under reduced pressure and SiO$_2$ flash chromatography (30% ethyl acetate in hexanes) afforded 61 mg of a pale yellow solid in 99% yield. R$_f$ 0.5 in 30% ethyl acetate in hexanes; $^1$H NMR (500 MHz, CDCl$_3$): δ 7.83-7.81 (m, 3H), 7.62 (s, 1H), 7.51-7.46 (m, 2H), 7.29 (dd, J=8.4, 1.5 Hz, 1H), 5.00 (d, J=7.4 Hz, 1H), 4.79-4.64 (m, 3H), 3.31 (dd, J=14.1, 5.9 Hz), 3.25 (dd, J=14.0, 6.5 Hz, 1H), 1.41 (s, 9H); $^{13}$C NMR (125 MHz, CDCl$_3$): δ 170.9, 155.2, 133.6, 132.8, 132.8, 128.8, 128.3, 127.8, 127.2, 126.5, 126.2, 114.0, 80.7, 54.5, 49.0, 38.2, 28.4; HRMS (ESI) m/z calcd for C$_{20}$H$_{22}$N$_2$O$_4$Na [M+Na]$^+$ 377.147. found 377.149.

(S)-cyanomethyl 2-((tert-butoxycarbonyl)(methyl)amino)-3-phenylpropanoate (Boc-Mef-OCH$_2$CN, 1e)

Chloroacetonitrile (1.1 mL) and DIPEA (258 mg, 0.341 mL, 1.99 mmol) were added to Boc-MePhe-OH (497 mg, 1.78 mmol) in tetrahydrofuran (5 mL) and stirred for 12 h. The solvent was removed under reduced pressure and SiO$_2$ flash chromatography (20-35% ethyl acetate in hexanes) afforded 505 mg of a pale yellow oil in 89% yield. R$_f$ 0.3 in 20% ethyl acetate in hexanes; $^1$H NMR (500 MHz, CDCl$_3$): δ 7.28-7.25 (m, 2H), 7.20-7.16 (m, 3H), 4.72-4.68 (m, 2H), 4.53-4.52 (m, 1H), 3.27 (m, 1H), 3.11-3.02 (m, 1H), 2.67 (d, J=17 Hz, 3H), 1.36 (d, J=12 Hz, 9H); $^{13}$C NMR (125 MHz, CDCl$_3$): δ 169.9, 155.5, 136.8, 128.9, 128.6, 128.4, 126.8, 126.7, 114.2, 80.8, 61.5, 48.7, 35.4, 33.0, 28.1; HRMS (ESI) m/z calcd for C$_{17}$H$_{22}$N$_2$O$_4$Na [M+Na]$^+$ 341.147. found 341.149.

(S)-cyanomethyl 2-acetamido-3-phenylpropanoate (Acf-OCH$_2$CN, 1f)

Chloroacetonitrile (2 mL) and DIPEA (630 mg, 0.841 mL, 4.87 mmol) were added to N—Ac-Phe-OH (501 mg, 2.42 mmol) and stirred for 12 h. The solvent was removed under reduced pressure and SiO₂ flash chromatography (50% ethyl acetate in hexanes) afforded (535 mg) of a pale yellow oil in 90% yield. $R_f$ 0.2 in 50% ethyl acetate in hexanes; ¹H NMR (500 MHz, CDCl₃): δ 7.26 (t, J=7 Hz, 2H), 7.22 (t, J=2.3 Hz, 1H), 7.07 (d, J=7.1 Hz, 2H), 6.02 (d, J=7.4 Hz, 1H), 4.83 (dd, J=14.0, 6.5 Hz, 1H), 4.66 (dd, J=15.7, 4.7 Hz, 2H), 3.10-3.01 (m, 2H), 1.91 (s, 3H); ¹³C NMR (125 MHz, CDCl₃): δ 170.6, 170.1, 135.2, 129.3, 139.0, 127.7, 114.0, 53.6, 53.2, 49.0, 37.7, 23.0; HRMS (ESI) m/z calcd for $C_{13}H_{14}N_2O_3Na$ [M+Na]⁺ 269.090. found 269.091.

(S)-cyanomethyl 2-azido-3-phenylpropanoate (Boc-N₃f-OCH₂CN, 1g)

Chloroacetonitrile (1 mL) and DIPEA (310 mg, 0.411 mL, 2.41 mmol) were added to 2-azido-3-phenylpropanoate and stirred for 12 h. The solvent was removed under reduced pressure and SiO₂ flash chromatography (40-50% ethyl acetate in hexanes) afforded (250 mg) of a white solid in 50% yield. $R_f$ 0.5 in 50% ethyl acetate in hexanes; ¹H NMR (500 MHz, CDCl₃) δ 7.37 (t, J=7.6 Hz, 2H), 7.32-7.29 (m, 1H), 7.25 (t, J=7.6 Hz, 2H), 4.77 (t, J=1.0 Hz, 1H), 4.18 (dd, J=6.2, 1.8 Hz, 1H), 3.21 (dd, J=14.0, 5.8 Hz, 1H), 3.08 (dd, J=13.9, 8.4 Hz, 1H); ¹³C NMR (125 MHz, CDCl₃) δ 168.8, 135.1, 129.3, 129.1, 127.8, 113.7, 62.9, 49.3, 37.7; HRMS (ESI) m/z calcd for $C_{11}H_{10}N_4O_2Na$ [M+Na]⁺ 253.070. found 253.071.

(S)-cyanomethyl 2-((tert-butoxycarbonyl)amino)-3-(7-methoxy-2-oxo-2H-chromen-4-yl)propanoate (Boc-Mcm-OCH₂CN, 1h)

A solution of 20% piperidine in tetrahydrofuran (4 mL) was added to Fmoc-Mcm-OH (200 mg, 0.439 mmol) and was stirred for 15 minutes. The solvent was removed under reduced pressure and ethyl acetate (10 mL) and 2M sodium hydroxide was added until pH>8 followed by addition of Boc anhydride (110 mg, 0.526 mmol) to the white residue and stirred overnight. The organic layer was extracted and washed with saturated sodium bicarbonate (2×10 mL) and all aqueous fractions were combined and acidified with 1 M sodium bisulfate until pH<2. The aqueous layer was then extracted with ethyl acetate (3×10 mL), dried with magnesium sulfate, and concentrated under reduced pressure. Chloroacetonitrile (1 mL) and DIPEA (62 mg, 82 µL, 0.48 mmol) were added to the white residue and stirred for 12 h. The solvent was removed under reduced pressure and SiO₂ flash chromatography (50%-65% ethyl acetate in hexanes) afforded 56 mg of a pale yellow oil in 35% yield. $R_f$ 0.4 in 50% ethyl acetate in hexanes; ¹H NMR (500 MHz, CDCl₃) δ 7.37 (d, J=8.7 Hz, 1H), 6.90 (dd, J=8.9, 2.4 Hz, 1H), 6.85 (d, J=2.1 Hz, 1H), 6.12 (s, 1H), 5.16 (d, J=7.7 Hz, 1H), 4.79 (d, J=4.2 Hz, 2H), 4.69-4.68 (m, 1H), 3.88 (s, 3H), 3.32 (dd, J=14.1, 5.2 Hz, 1H), 3.12 (dd, J=13.9, 8.4 Hz, 1H), 1.41 (s, 9H); ¹³C NMR (125 MHz, CDCl₃) δ 170.0, 163.2, 160.8, 155.9, 155.1, 150.5, 125.3, 113.7, 113.3, 113.0, 112.3, 101.6, 81.3, 56.0, 52.8, 49.5, 34.6, 28.4; HRMS (ESI) m/z calcd for $C_{20}H_{22}N_2O_7Na$ [M+Na]⁺ 425.133. found 425.133.

(S)-cyanomethyl 3-(4-benzoylphenyl)-2-((tert-butoxycarbonyl)amino)propanoate (Boc-Bzf-OCH₂CN, 1i)

Chloroacetonitrile (1 mL) and DIPEA (20 mg, 34 µL, 0.21 mmol) were added to Boc-p-benzoylphenylalanine (61 mg, 0.19 mmol). The reaction was stirred for 18 h, then concentrated under reduced pressure. SiO₂ flash chromatography (40% ethyl acetate in hexanes) afforded 70 mg of a pale yellow oil in 93% yield. $R_f$ 0.5 in 50% ethyl acetate in hexanes. ¹H NMR (500 MHz, CDCl₃) δ 7.79 (dd, J=7.1, 4.9 Hz, 4H), 7.59 (t, J=7.6 Hz, 1H), 7.48 (t, J=7.6 Hz, 2H), 7.29 (d, J=8.0 Hz, 2H), 5.00 (d, J=7.4 Hz, 1H), 4.83 (d, J=15.7 Hz, 1H), 4.72-4.69 (m, 2H), 3.25 (dd, J=13.7, 5.8 Hz, 1H), 3.16 (dd, J=13.1, 6.5 Hz, 1H), 1.43 (s, 9H); ¹³C NMR (125 MHz, CDCl₃) δ 196.4, 170.6, 155.1, 140.3, 137.6, 136.9, 132.7, 130.8, 130.2, 129.4, 128.5, 113.9; HRMS (ESI) m/z calcd for $C_{23}H_{24}N_2NaO_5$ [M+Na]⁺ 431.158. found 431.158.

(R)-2-((tert-butoxycarbonyl)amino)-3-(methyldisulfanyl)propanoic acid (Boc-L-Csm-OH)

(R)-2-((tert-butoxycarbonyl)amino)-3-mercaptopropanoic acid (Boc-L-Cys-OH) (110 mg, 0.5 mmol) was dissolved in H₂O/THF (50% v/v, 20 mL). To the solution was added sodium thiomethoxide (350 mg, 5.0 mmol) at 0° C. Then, a solution of iodine in 95% EtOH was added dropwise until the color of the reaction system changed from colorless to brown. The mixture was stirred for 5.5 h with warming to room temperature. After removing THF under reduced pressure, reaction mixture was neutralized by 1 N HCl aq. until pH 2-3. The solution was extracted with EtOAc. The extract was washed with saturated NaS₂O₄ aq. and brine, and dried over MgSO₄. Concentration under reduced pressure followed by flash chromatography over silica gel in EtOAc/Hexanes/AcOH (75:25:1) gave Boc-L-Csm-OH (90.8 mg, 68% yield). ¹H NMR (360 MHz, CDCl₃) δ 5.34 (s, 1H), 4.63 (br, s, 1H), 3.26-3.16 (m, 2H), 2.43 (m, 3H), 1.47 (s, 9H); LRMS (ESI) m/z calcd for $C_9H_{18}NO_4S_2$ (M+H)⁺ 268.1. found 268.2.

(R)-2-((tert-butoxycarbonyl)amino)-3-(isopropyldisulfanyl)propanoic acid (Boc-L-Csp-OH)

Boc-L-Cys-OH (221 mg, 1.0 mmol) was dissolved in H₂O/THF (50% v/v, 20 mL). To the solution was added 10 N sodium hydroxide aq. (1.2 mL, 12 mmol) and 2-propane thiol (929 uL, 10 mmol) at 0° C. Then, a solution of iodine in 95% EtOH was added dropwise until the color of the reaction system changed from colorless to brown. The mixture was stirred for 1 d with warming to room temperature. After removing THF under reduced pressure, reaction mixture was neutralized by 1 N HCl aq. until pH 2-3. The solution was extracted with EtOAc. The extract was washed with saturated aq. NaS₂O₄ and brine, and dried over MgSO₄. Concentration under reduced pressure followed by flash chromatography over silica gel in EtOAc/Hexanes/AcOH (75:25:1) gave Boc-L-Csp-OH (145.7 mg, 49% yield): ¹H NMR (360 MHz, CDCl₃) δ 5.34 (s, 1H), 4.59 (br, s, 1H), 3.24-3.14 (m, 2H), 3.09-3.00 (m, 1H), 1.47 (s, 9H), 1.32-1.30 (dd, 6H); LRMS (ESI) m/z calcd for $C_{11}H_{22}NO_4S_2$ (M+H)⁺ 296.1. found 296.1.

(R)-cyanomethyl 2-((tert-butoxycarbonyl)amino)-3-(methyldisulfanyl)propanoate (Boc-L-Csm-OCH₂CN, 1k)

Boc-L-Csm-OH (100 mg, 0.5 mmol) was dissolved in THF (1 mL). To the solution were added chloroacetonitrile and diisopropylamine (350 mg, 5.0 mmol). The mixture was stirred for over-night under N₂ atmosphere. Concentration under reduced pressure followed by flash chromatography over silica gel with EtOAc/Hexanes (3:1) gave 1k (104.3 mg, 67% yield) as a white powder: ¹H NMR (360 MHz, CDCl₃) δ 5.34 (s, 1H), 4.86-4.74 (m, 2H), 4.63 (s, 1H), 3.26-3.16 (m, 2H), 2.43 (m, 3H), 1.47 (s, 9H); LRMS (ESI) m/z calcd for $C_{11}H_{19}N_2O_4S_2$ (M+H)$^+$ 307.1. found 307.1.

(R)-cyanomethyl 2-((tert-butoxycarbonyl)amino)-3-(isopropyldisulfanyl)propanoate (Boc-L-Csp-OCH$_2$CN, 1l)

Boc-L-Csp-OH (100 mg, 339 μmol) was dissolved in THF (1 mL). To the solution were added chloroacetonitrile (1.08 mL, 16.2 mmol) and diisopropylamine (118 uL, 647 μmol). The mixture was stirred for over-night under N$_2$ atmosphere. Concentration under reduced pressure followed by flash chromatography over silica gel with EtOAc/Hexanes (3:1) gave 1l (86.3 mg, 74% yield): $^1$H NMR (360 MHz, CDCl$_3$) δ 5.34 (m, 1H), 4.86-4.74 (m, 2H), 4.67 (br, s, 1H), 3.13 (d, J=5.2 Hz, 2H), 3.08-3.00 (m, 1H), 1.46 (s, 9H), 1.33-1.31 (m, 6H); LRMS (ESI) m/z calcd for $C_{11}H_{22}NO_4S_2$ (M+H)$^+$ 296.1. found 296.3.

(S)-2-((tert-butoxycarbonyl)amino)-4-(methyldisulfanyl)butanoic acid (Boc-L-Hcm-OH)

(S)-2-((tert-butoxycarbonyl)amino)-4-mercaptobutanoic acid (Boc-L-Hcs-OH) (188 mg, 0.4 mmol) was dissolved in H$_2$O/THF (50% v/v, 16 mL). To the solution was added sodium thiomethoxide (560 mg, 8.0 mmol) at 0° C. Then, a solution of iodine in 95% EtOH was added dropwise until the color of the reaction system changed from colorless to brown. The mixture was stirred for 1.5 h with warming to room temperature. After removing THF under reduced pressure, reaction mixture was neutralized by 1 N HCl aq. until pH 2-3. The solution was extracted with EtOAc. The extract was washed with saturated NaS$_2$O$_4$ aq. and brine, and dried over MgSO$_4$. Concentration under reduced pressure followed by flash chromatography over silica gel with EtOAc/Hexanes/AcOH (75:25:1) gave Boc-L-Hcm-OH (179.3 mg, 80% yield): $^1$H NMR (360 MHz, CDCl$_3$) δ 5.06 (s, 1H), 4.44 (s, 1H), 2.78 (t, J=7.7 Hz, 2H), 2.42 (s, 3H), 2.35 (m, 1H), 2.09 (m, 1H), 1.45 (s, 9H); LRMS (ESI) m/z calcd for $C_{10}H_{20}NO_4S_2$ (M+H)$^+$ 282.1. found 282.1.

(S)-cyanomethyl 2-((tert-butoxycarbonyl)amino)-4-(methyldisulfanyl)butanoate (Boc-L-Hcm-OCH$_2$CN, 1n)

Boc-L-Hcm-OH (43 mg, 153 μmol) was dissolved in THF (1 mL). To the solution were added chloroacetonitrile (484 μL, 7.65 mmol) and diisopropylamine (53 μL, 306 μmol). The mixture was stirred overnight under N$_2$ atmosphere. After 18 h, additional chloroacetonitrile (484 L, 7.65 mmol) was added. Concentration under reduced pressure followed by flash chromatography over silica gel with AcOEt-Hexane (3:1) gave the titled compound in (31.3 mg, 63% yield): $^1$H NMR (360 MHz, CDCl$_3$) δ 5.02 (s, 1H), 4.73 (dd, J=31.3 Hz, 2H) 4.49 (s, 1H), 2.77-2.73 (m, 2H), 2.37 (m, 3H), 2.37-2.27 (m, 1H), 2.13-2.02 (m, 1H), 1.46 (s, 9H); LRMS (ESI) m/z calcd for $C_{12}H_{21}N_2O_4S_2$ (M+H)$^+$ 321.1. found 321.0.

(S)-(2R,3R,4R,5R)-2-(6-Amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-phenylproparioate (Boc-Phe-(DMT)-A, 3a)

(DMT)-A (25 mg, 44 μmol) was dissolved in 5 mL of tetrahydrofuran (dried with 4 Å molecular sieves) in an oven-dried 4 dram reaction vessel. Twenty equivalents of 1a (272 mg, 0.895 mmol) were added to the reaction mixture. TBAAc (4.9 mg, 16 μmol, reaction catalyst) was added last to the reaction mixture. In reproductions of this reaction, TBAAc additions varied according to reaction progress. The reaction stirred under argon overnight at room temperature for 1-4 days. After evaporation of solvent, the product was purified on silica gel (gradient solvent system; 20-0% petroleum ether in EtOAc, 5% methanol in EtOAc) to give 27 mg (75%) of a pale-yellow foam after evaporation. R$_f$ 0.5 in 5% methanol in EtOAc. $^1$H NMR (500 MHz, THF-d$_8$) δ 8.08 (s, 1H), 8.00 (s, 1H), 7.44 (d, J=3.68 Hz, 2H), 7.32 (d, J=8.85 Hz, 4H), 7.20 (dd, J=6.66, 2H), 7.13 (t, J=7.25 Hz, 1H), 7.21-7.10 (m, 4H), 6.77 (d, J=4.30 Hz, 2H), 6.75 (d, J=4.29 Hz, 2H), 5.92 (d, J=4.87 Hz, 1H), 5.49 (t, 4.34 Hz, 1H), 5.13 (t, J=5.54 Hz, 1H), 4.51-4.47 (m, 1H), 4.14 (t, J=4.07 Hz, 1H), 3.71 (s, 6H) (S), 3.42-3.32 (m, 2H), 3.12-2.96 (m, 3H), 1.37 (s, 9H); $^{13}$C NMR (125 MHz, THF-d$_8$) δ 172.2, 159.9, 157.6, 156.7, 153.8, 146.3, 138.3, 146.3, 138.3, 1367.0, 136.9, 131.2, 131.1, 130.3, 129.3, 129.2, 129.1, 128.6, 128.5, 127.5, 114.0, 113.9, 89.7, 87.5, 82.5, 79.7, 75.1, 73.5, 64.7, 56.4, 55.5, 38.9, 30.6, 28.8; LRMS (ESI) calcd m/z for $C_{45}H_{48}N_6O_9H$ (M±H)$^+$ 816.9, $C_{45}H_{48}N_6O_9Na$ (M+Na)$^+$ 839.3. found 817.3, 839.3.)

(S)-(2R,3R,4R,5R)-2-(6-Amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-phenylpropanoate (3a) from 2a (DMT)-A (26 mg, 45 μmol) was dissolved in 5 mL of tetrahydrofuran (dried with 4 Å molecular sieves) in an oven-dried 4-dram reaction vessel. Twenty equivalents of 2a (321 mg, 0.885 mmol) were added to the reaction mixture. TBAAc (19 mg, 64 μmol, the reaction catalyst) was added last to the reaction mixture in two separate additions, 6 mg, at the beginning of the reaction, and 1.3 mg after the first 24 h of reaction. The reaction stirred under argon overnight at room temperature for 2 days, After evaporation of solvent, the product was purified on silica gel (gradient solvent system; 20-0% petroleum ether in EtOAc, 5% methanol in EtOAc) to give 19.1 mg (52.1%) of a pale-yellow foam after evaporation. LRMS (ESI) calcd m/z for $C_{45}H_{48}N_6O_9H$ (MAW 816.9, $C_{45}H_{48}N_6O_9Na$ (M+Na)$^+$ 839.3. found 817.4, 839.4.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-4-methylpentanoate (Boc-Leu-(DMT)-A, 3b)

Figure 7A:
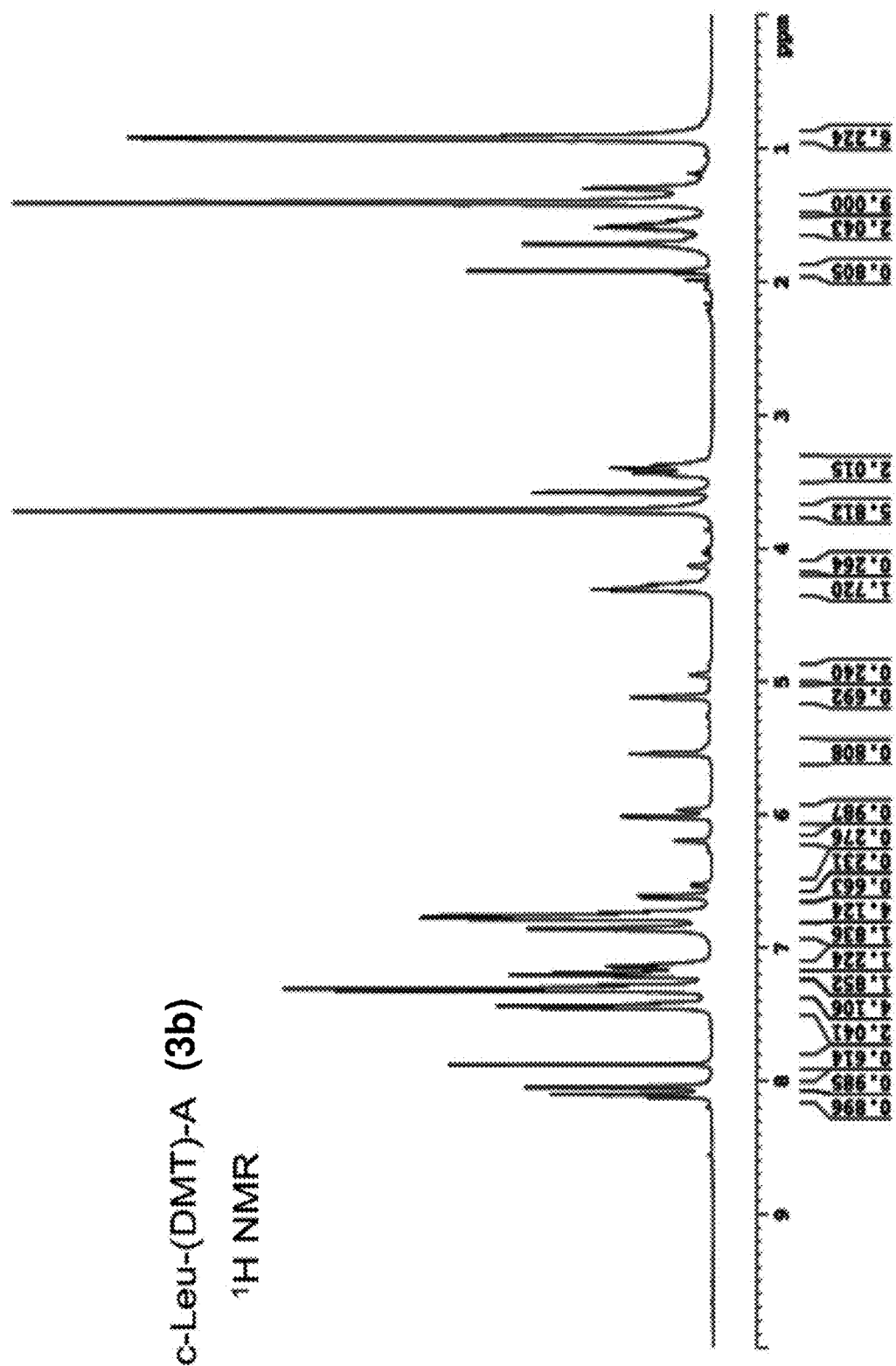
FIGS. 7A-7B are a set of images depicting $^1H$ and $^{13}C$ NMR characterization of Boc-Leu-(DMT)-A 3b.
Figure 7B:
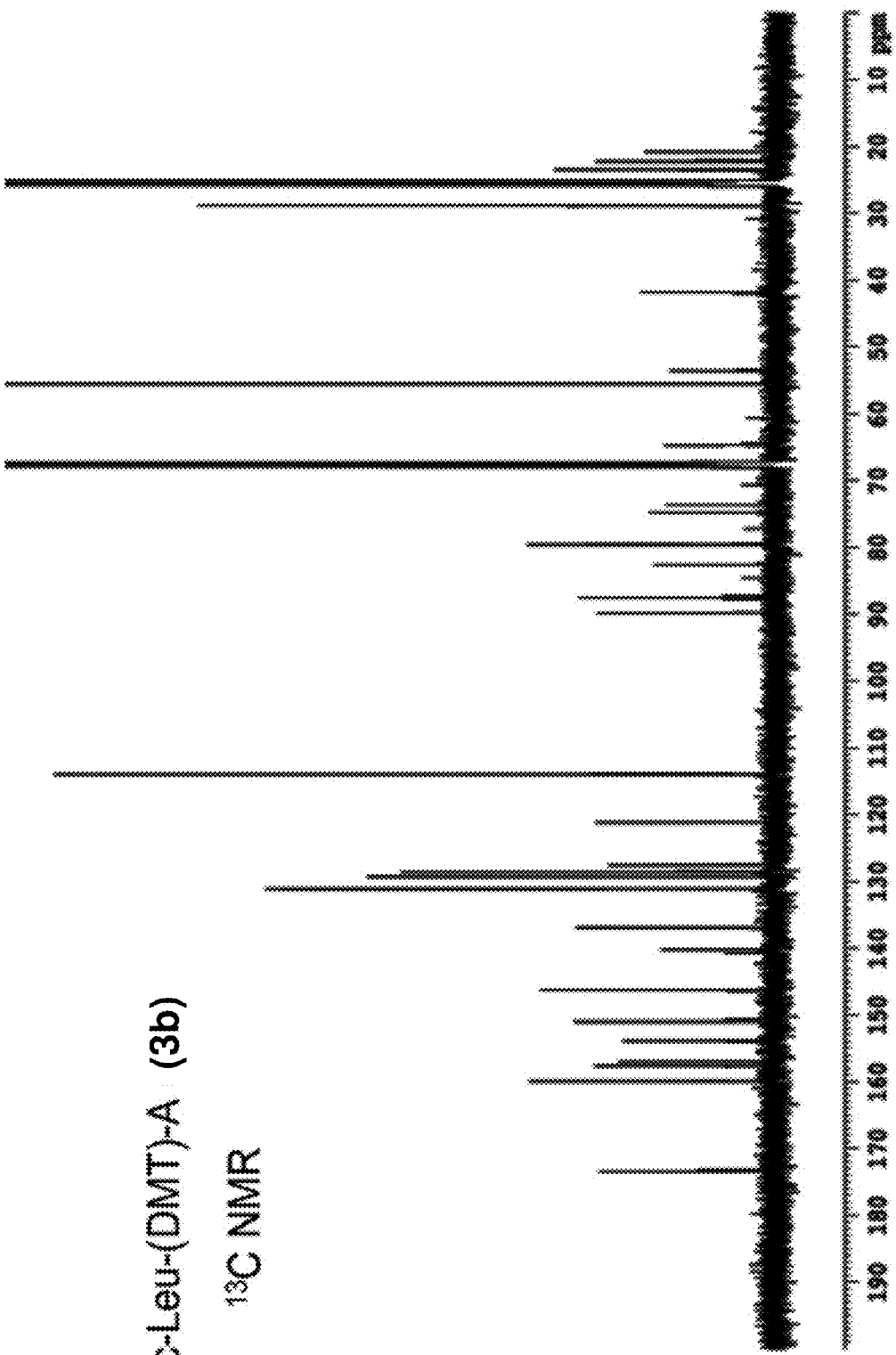

Tetrahydrofuran (5 mL) was added to Boc-Leu-OCH$_2$CN 1b (226 mg, 0.837 mmol), (DMT)-A (120 mg, 0.211 mmol), and TBAAc (15 mg, catalyst) and stirred for 24 h. The solvent was removed under reduced pressure and chromatography (80-100% ethyl acetate in petroleum ether, 5% methanol in ethyl acetate), afforded 122 mg of a white solid in 74% yield. $R_f$ 0.5 in 5% methanol in ethyl acetate; $^1$H and $^{13}$C NMR for 3b shown in FIGS. 7A-7B; LRMS (ESI) m/z calcd for $C_{42}H_{50}N_6O_9Na$ (M+Na)$^+$ 805.4. found 805.3.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 3-(4-azidophenyl)-2-((tert-butoxycarbonyl)amino)propanoate (Boc-Azf-(DMT)-A, 3c)

Figure 8B:
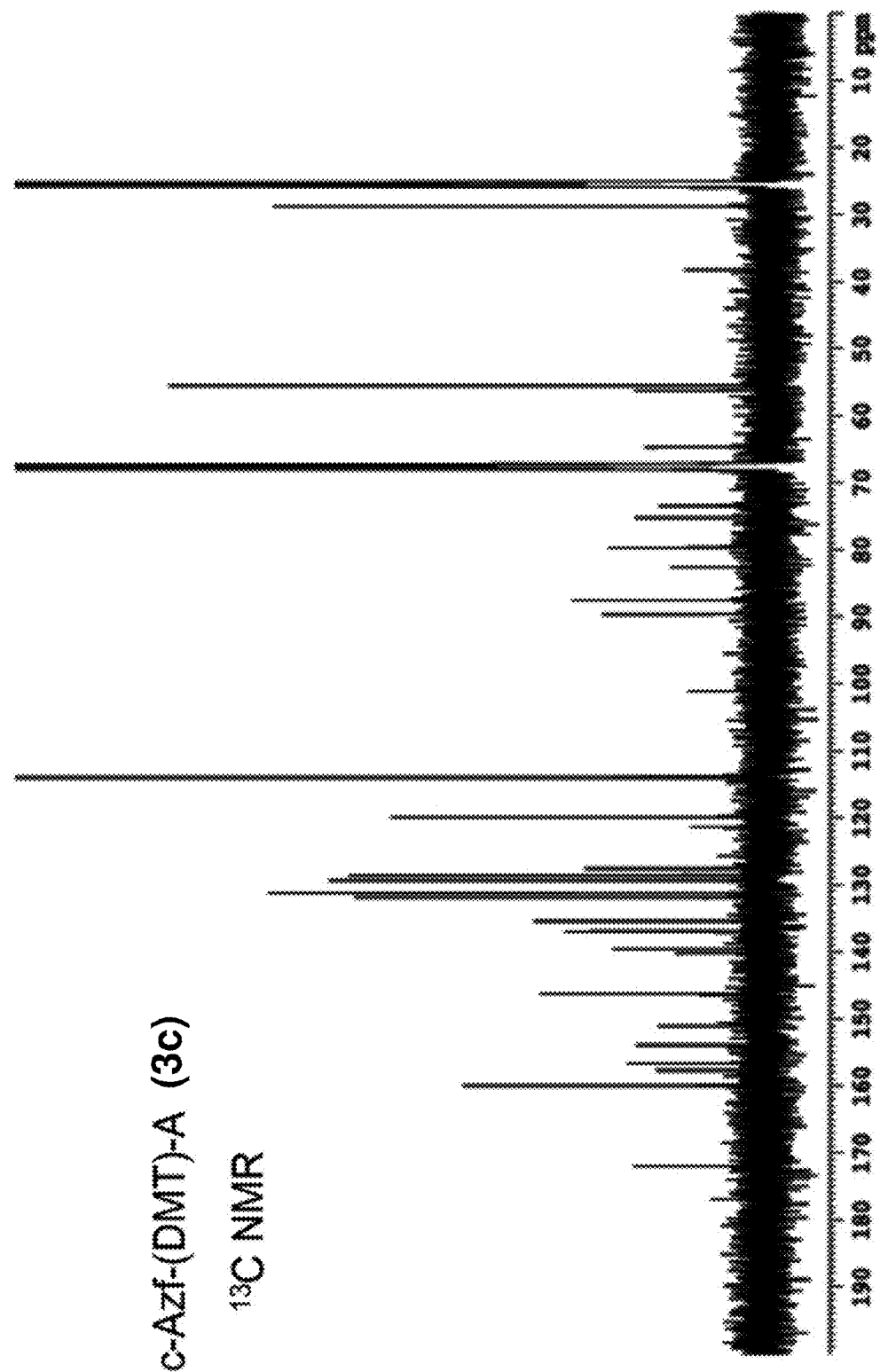

Tetrahydrofuran (5 mL) was added to Boc-Azf-OCH$_2$CN 1c (101 mg, 0.290 mmol), (DMT)-A (43 mg, 75 μmol), and TBAAc (2 mg, catalyst) and stirred for 24 h. Solvent was removed under vacuum and preparative TLC (100% ethyl acetate), afforded 44 mg of white solid in 69% yield. $R_f$ 0.3-0.5 in ethyl acetate; $^1$H and $^{13}$C NMR for 3c shown in FIGS. 8A-8B; LRMS (ESI) m/z calcd for $C_{42}H_{47}N_9O_9Na$ (M+Na)$^+$ 880.3. found 880.4.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-(naphthalen-2-yl)propanoate (Boc-Nap-(DMT)-A, 3d)

Figure 9A:
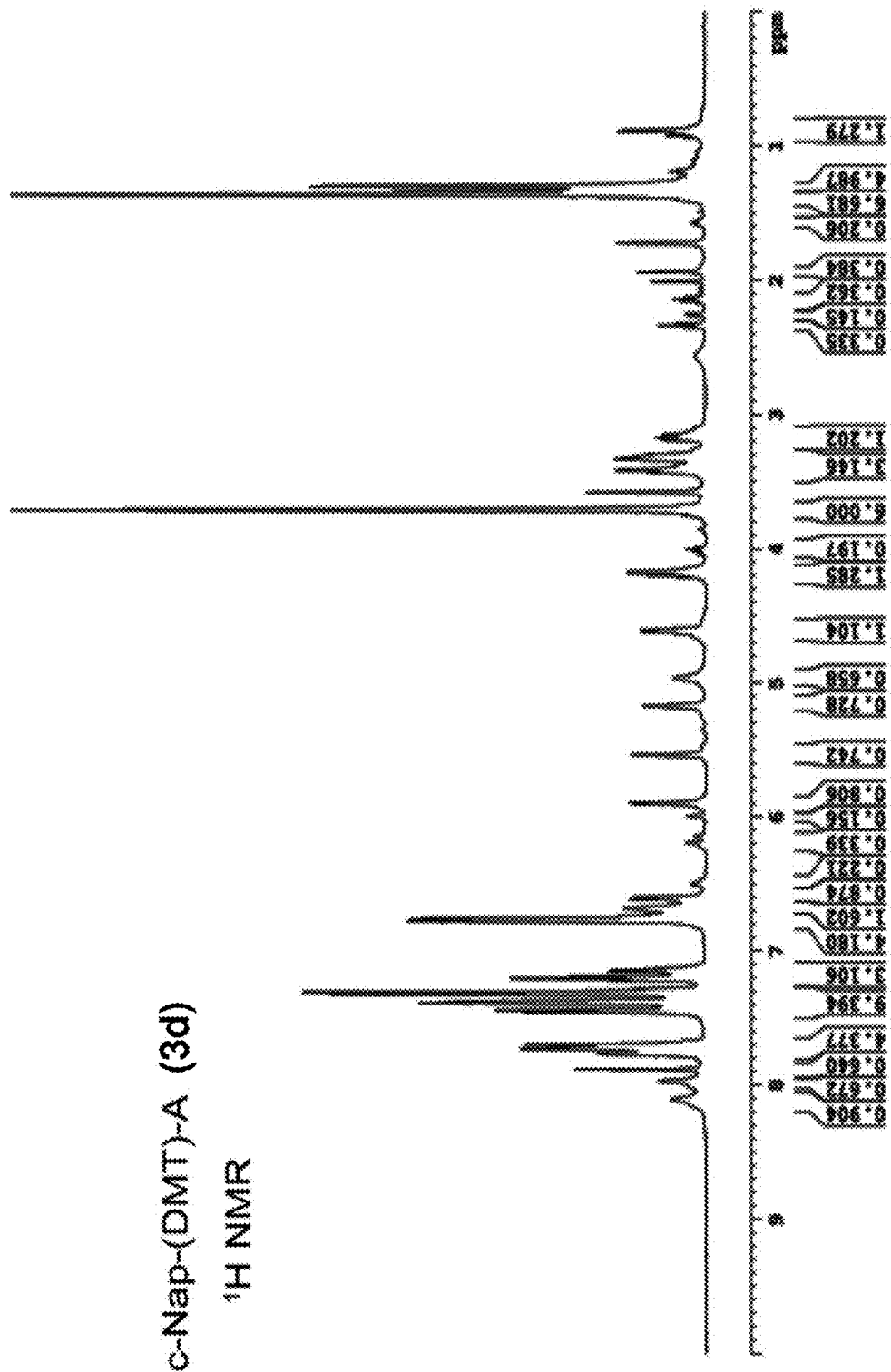
FIGS. 9A-9B are a set of images depicting $^1H$ and $^{13}C$ NMR characterization of Boc-Nap-(DMT)-A 3d.
Figure 9B:
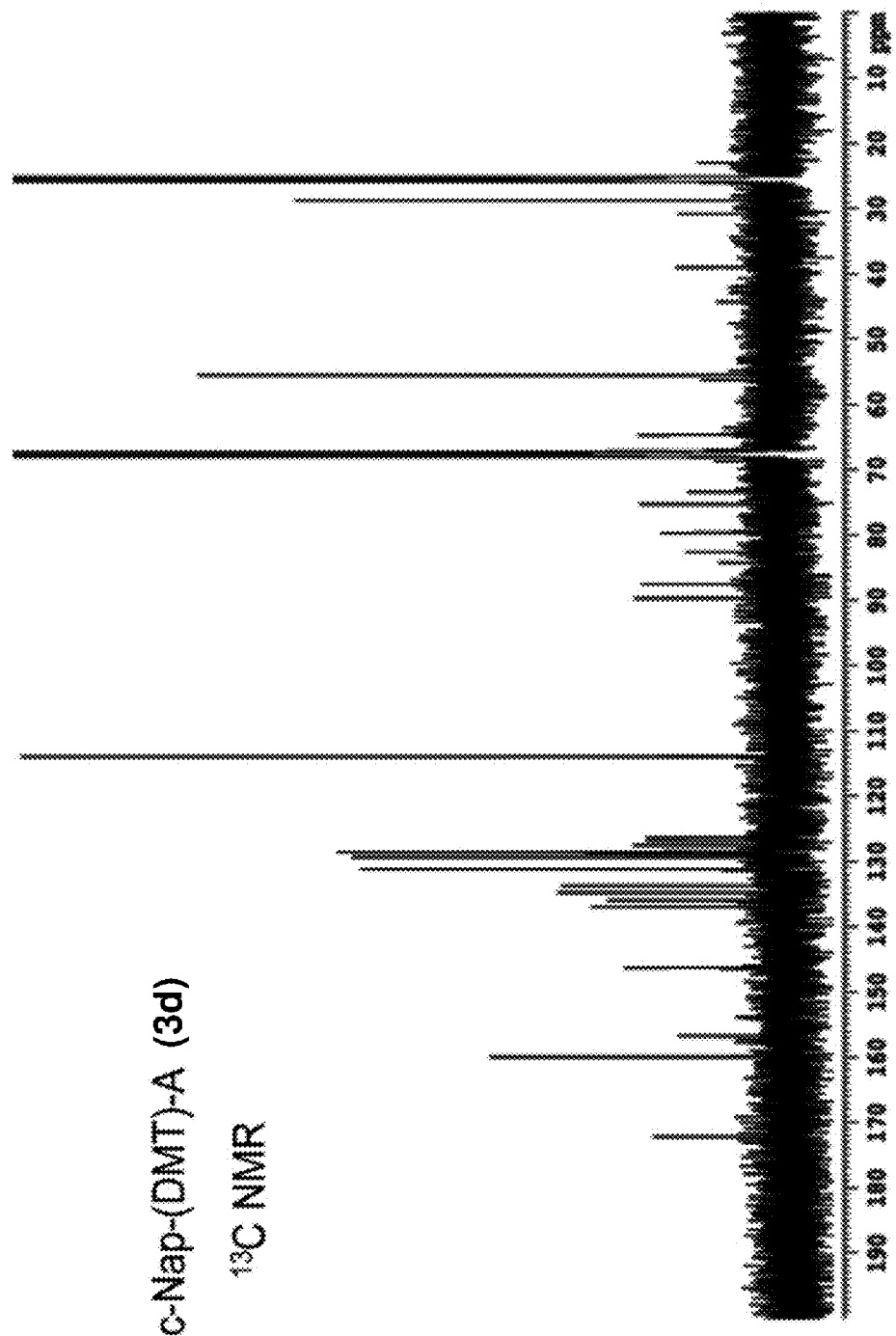

Tetrahydrofuran (5 mL) was added to Boc-Nap-OCH$_2$CN 1d (58 mg, 0.16 mmol), (DMT)-A (26 mg, 46 μmol), and TBAAc (6.4 mg, catalyst) and stirred for 24 h. The solvent was removed under reduced pressure and preparative TLC (5% methanol in ethyl acetate), afforded 36 mg of a white solid in 91% yield. $R_f$ 0.3-0.5 in 5% methanol in ethyl acetate; $^1$H and $^{13}$C NMR for 3d shown in FIGS. 9A-9B; LRMS (ESI) m/z calcd for $C_{49}H_{50}N_6O_9Na$ (M+Na)$^+$ 889.9. found 889.4.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)(methyl)amino)-3-phenylpropanoate (Boc-Mef-(DMT)-A, 3e)

Figure 10A:
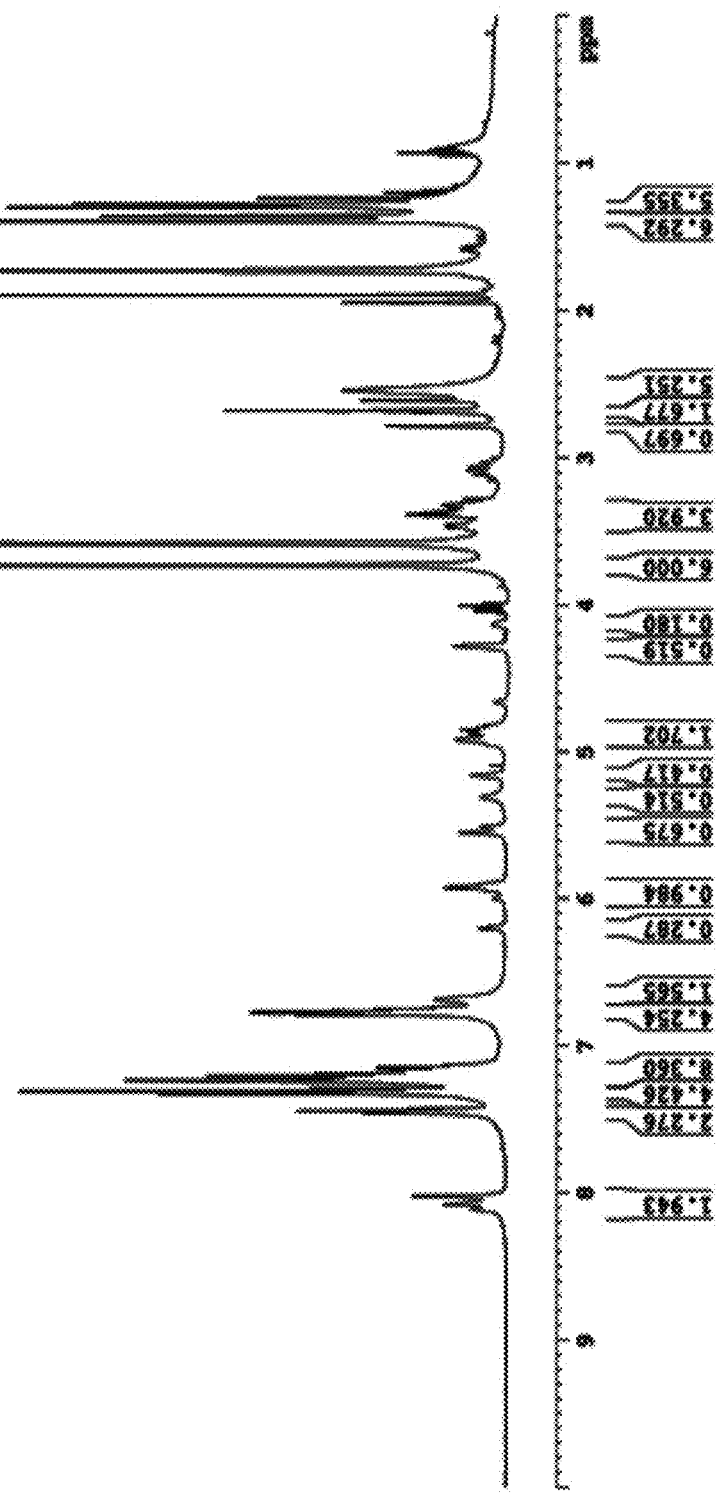
FIGS. 10A-10B are a set of images depicting $^1$H and $^{13}$C NMR characterization of Boc-Mef-(DMT)-A 3e.
Figure 10B:
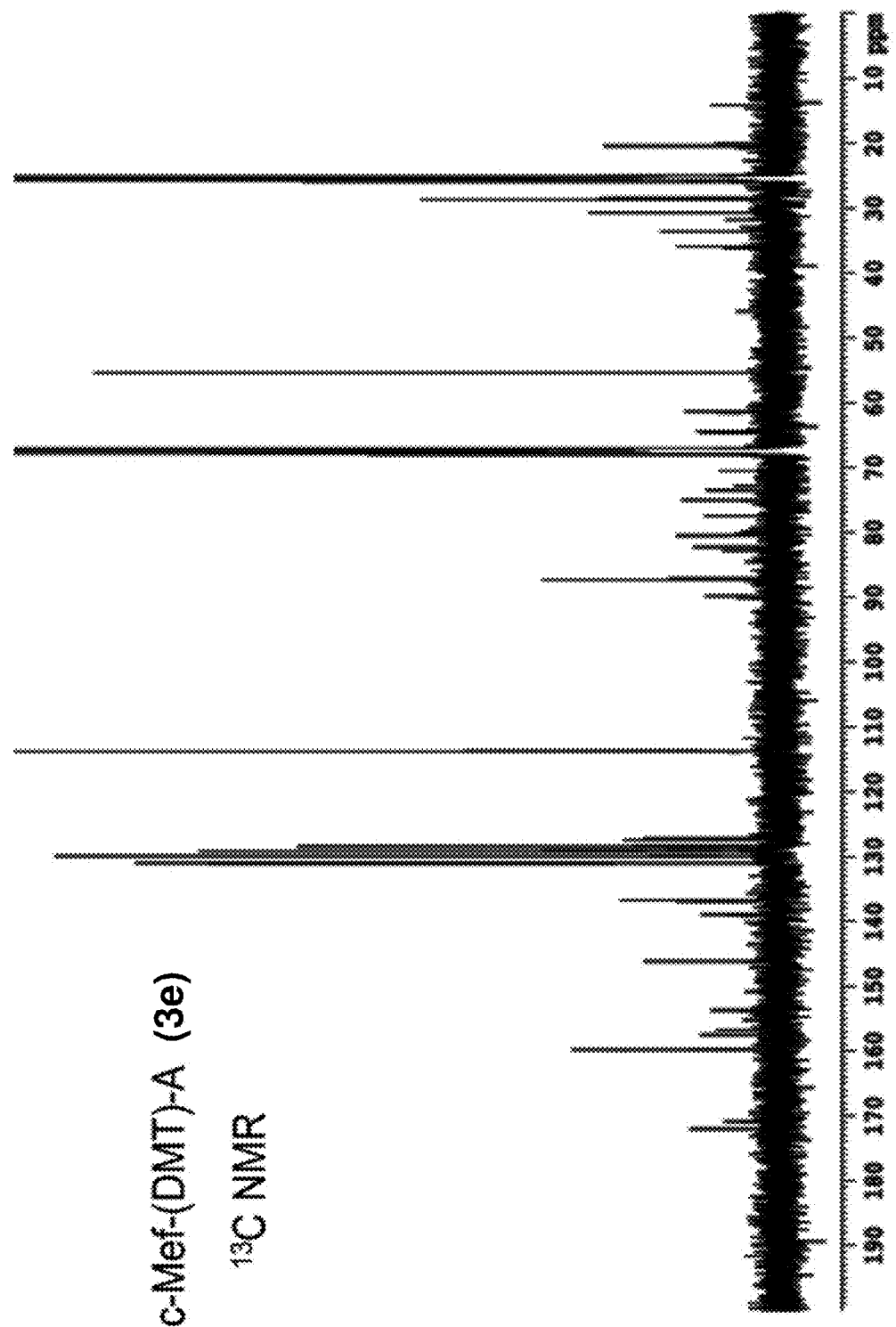

Tetrahydrofuran (3.5 mL) and DIPEA (44 mg, 60 μL, 0.35 mmol) were added to Boc-Mef-OCH$_2$CN 1e (110 mg, 0.347 mmol), (DMT)-A (50 mg, 89 μmol), and TBAAc (3 mg, catalyst) and stirred for 12 h. The solvent was removed under reduced pressure and SiO$_2$ flash chromatography (50-100% ethyl acetate in hexanes), afforded 10 mg of a white solid in 14% yield. $R_f$ 0.4-0.5 in ethyl acetate; $^1$H and $^{13}$C NMR for 3e shown in FIGS. 10A-10B; LRMS (ESI) m/z calcd for $C_{46}H_{50}N_6NaO_9$ (M+Na)$^+$ 853.4. found 853.5.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)acetamido)-3-phenylpropanoate (Boc-Acf-(DMT)-A, 3f)

Figure 11A:
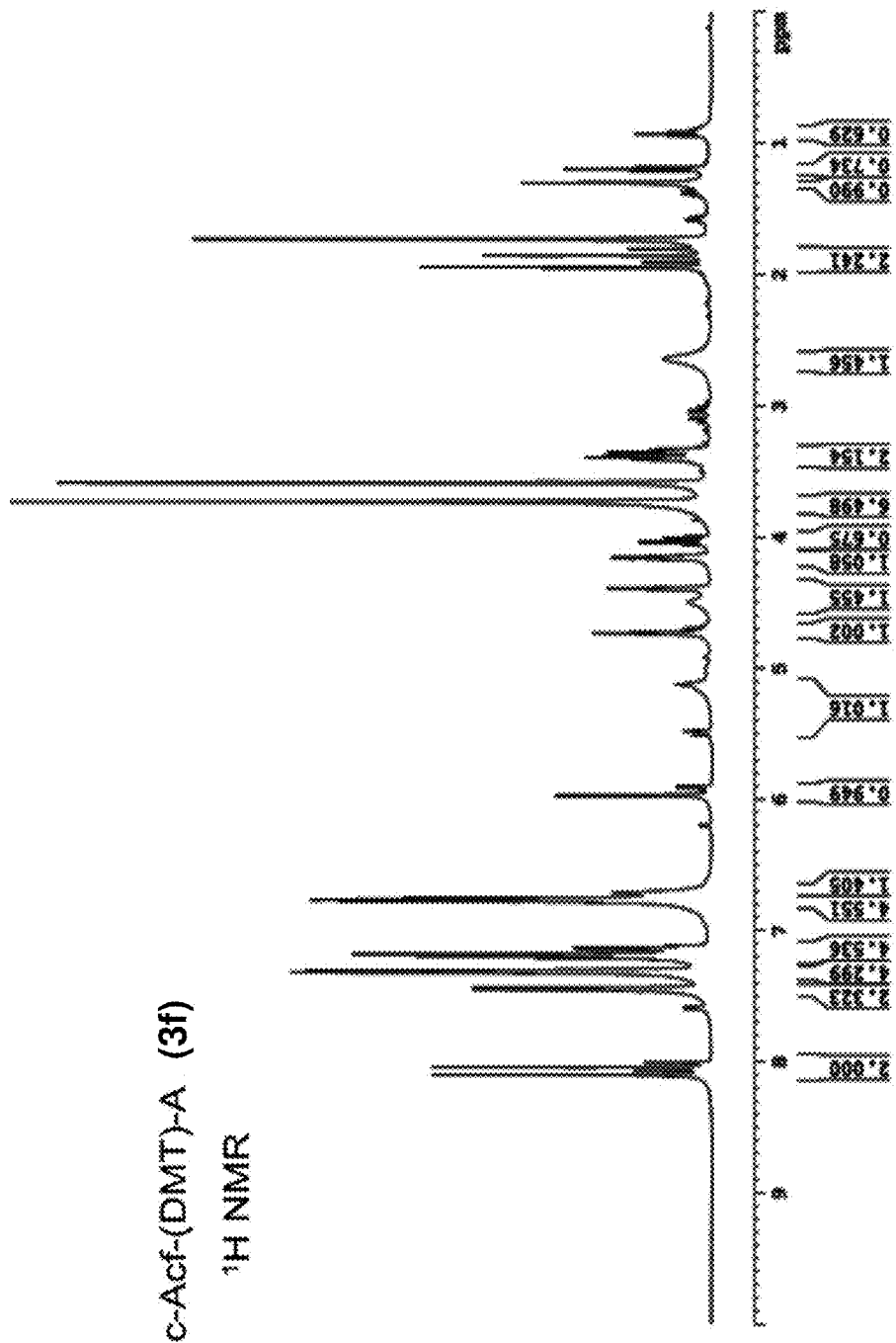
FIGS. 11A-11B are a set of images depicting $^1$H and $^{13}$C NMR characterization of Boc-Acf-(DMT)-A 3f.
Figure 11B:
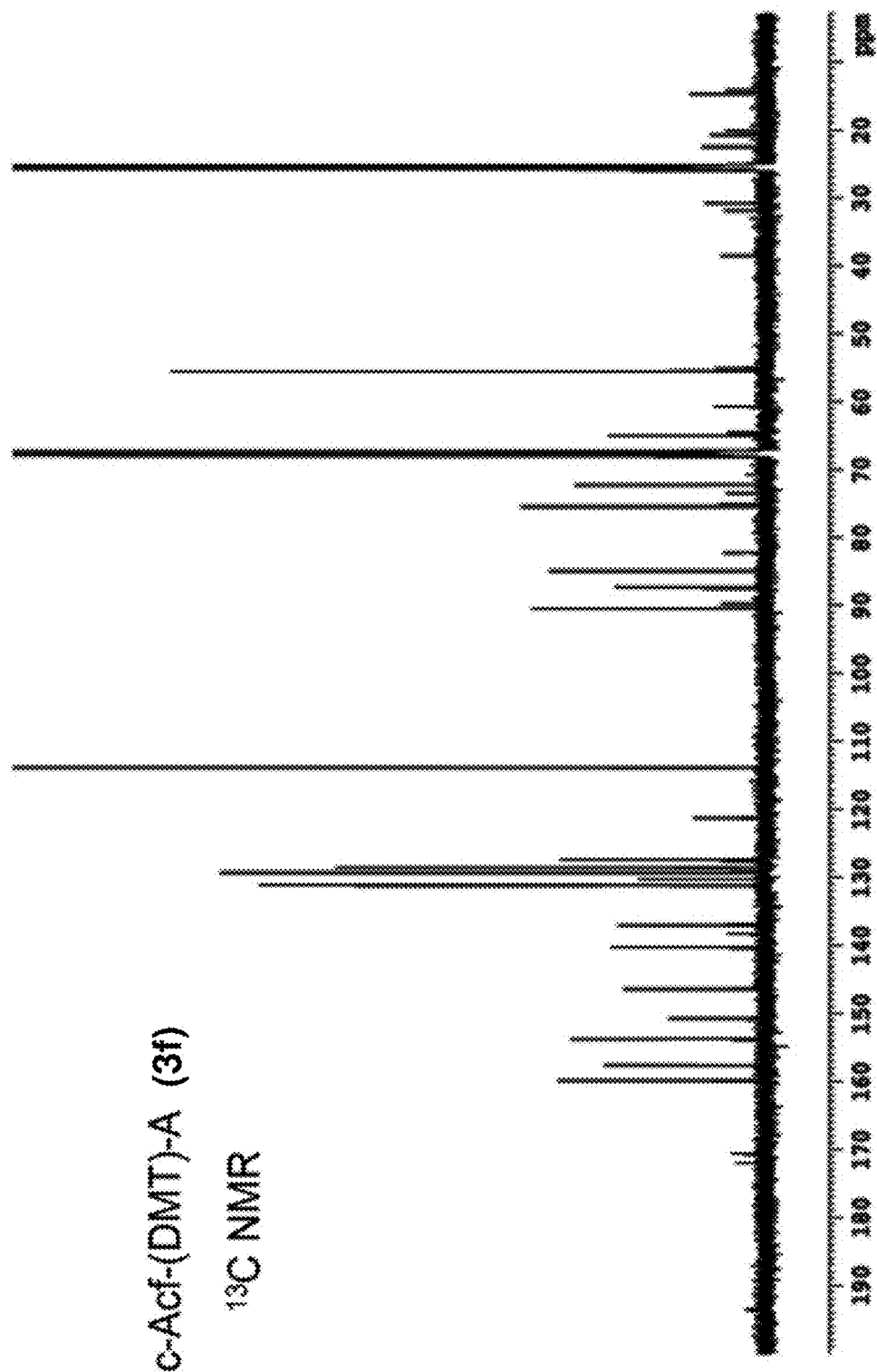

Tetrahydrofuran (5 mL) and DIPEA (250 mg, 0.30 mL, 1.9 mmol) were added to Boc-Acf-OCH$_2$CN 1f (400 mg, 1.93 mmol), (DMT)-A (73 mg, 0.13 mmol) and TBAAc (5 mg, catalyst) and stirred for 12 h. The solvent was removed under reduced pressure and SiO$_2$ flash chromatography (5% methanol in ethyl acetate), afforded 75 mg of a clear solid that was mix of DMTA and product. Subsequent HPLC analysis suggests approximately 38% of this mixture was product. $R_f$ 0.1-0.2 5% methanol in ethyl acetate; $^1$H and $^{13}$C NMR for 3f shown in FIGS. 11A-11B; LRMS (ESI) m/z calcd for $C_{42}H_{43}N_6O_8$ (M+H)$^+$ 759.3 $C_{42}H_{42}N_6NaO_8$ (M+Na)$^+$ 781.3. found 759.3, 781.4.

(S)-(2R,3R,4R,5R)-2-(6-amino-9H-purin-9-yl)-5-((bis(4-methoxyphenyl) (phenyl)methoxy)methyl)-4-hydroxytetrahydrofuran-3-yl 2-((tert-butoxycarbonyl)azido)-3-phenylpropanoate (Boc-N$_3$f-(DMT)-A, 3g)

Figure 12B:
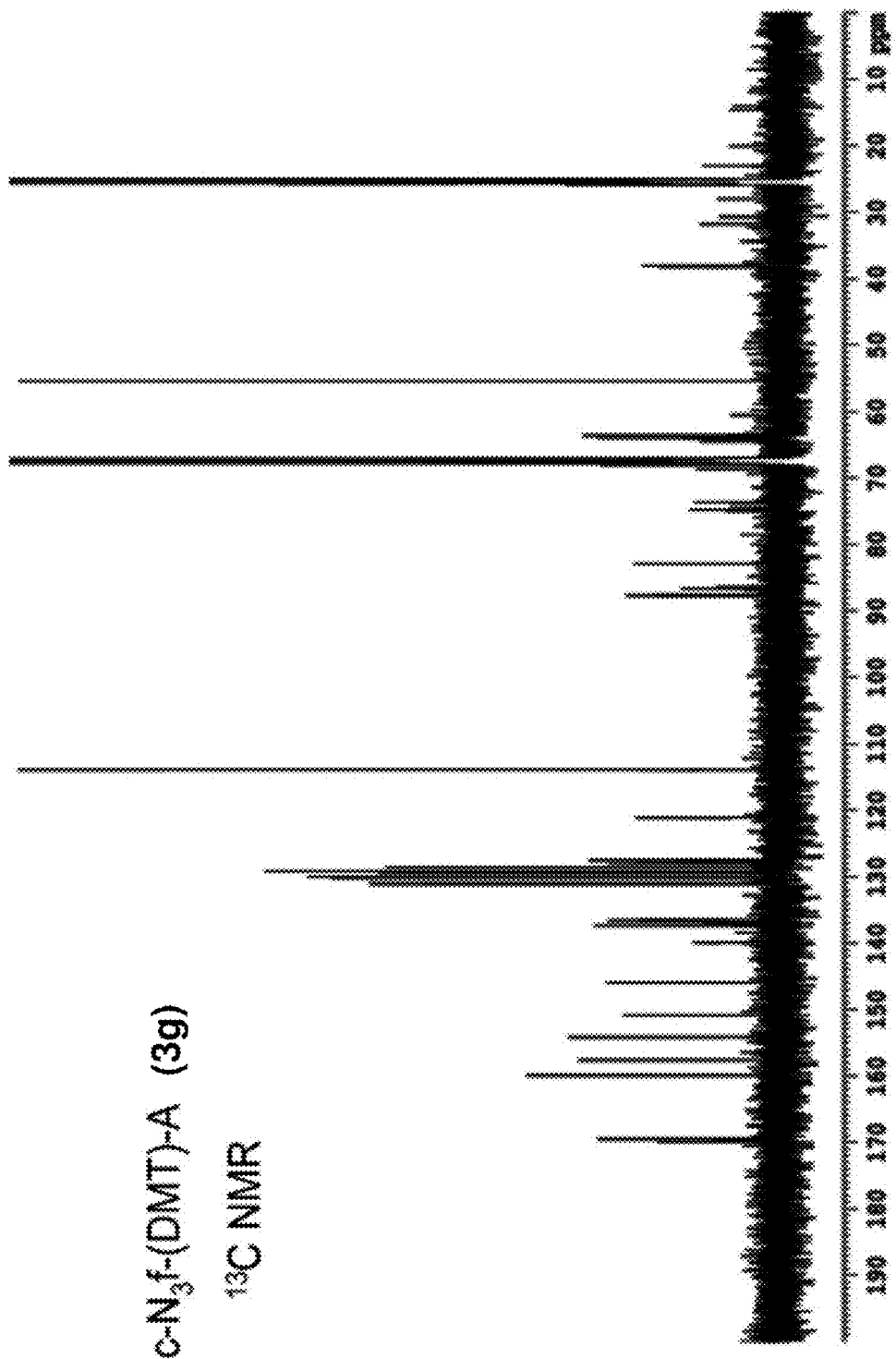

Tetrahydrofuran (3.5 mL) and DIPEA (44 mg, 60 μL, 0.35 mmol) were added to Boc-N$_3$f-OCH$_2$CN 1g (80 mg, 0.35 mmol), (DMT)-A (50 mg, 89 μmol), and TBAC (3 mg, catalyst) and stirred for 12 h. The solvent was removed under reduced pressure and purification by silica flash chromatography (75-100% ethyl acetate in hexanes), afforded 53 mg of a white solid in 80% yield. $R_f$ 0.3-0.5 in ethyl acetate; $^1$H and $^{13}$C NMR for 3g shown in FIG. 12; LRMS (ESI) m/z calcd for $C_{40}H_{39}N_8O_7$ (M+H)$^+$ 743.3, $C_{40}H_{39}N_8O_7Na$ (M+Na)$^+$ 765.3. found 743.4, 765.4; FTIR (Film) $\lambda_{max}$ 3334, 3179, 3063, 3032, 2953, 2934, 2837, 2112 (—N$_3$), 1757, 1644, 1606, 1508, 1252, 1177 cm$^{-1}$.

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-(7-methoxy-2-oxo-2H-chromen-4-yl) propanoate (Boc-Mcm-(DMT)-A, 3h)

Figure 13A:
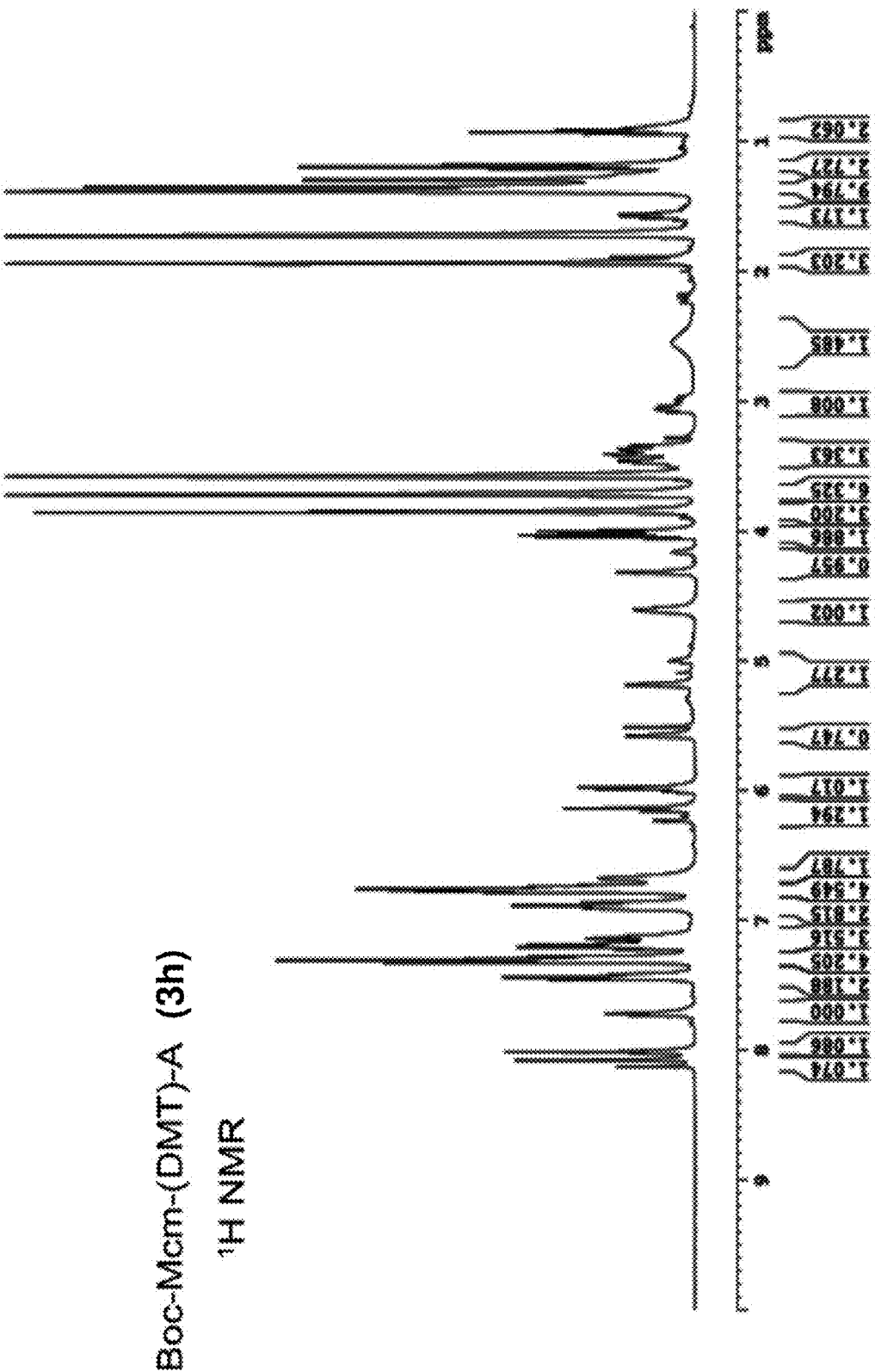

Tetrahydrofuran (3.5 ml) and DIPEA (44 mg, 60 μl, 0.35 mmol) were added to Boc-Mcm-OCH$_2$CN 1h (56 mg, 0.15 mmol), (DMT)-A (50 mg, 89 μmol), and TBAAc (3 mg, catalyst) and stirred for 12 h. The solvent was removed under reduced pressure and SiO$_2$ flash chromatography (50-100% ethyl acetate in hexanes), afforded 35 mg of a white solid in 43% yield. $R_f$ 0.3-0.4 in ethyl acetate; $^1$H and $^{13}$C NMR for 3h shown in FIG. 13; LRMS (ESI) m/z calcd for $C_{49}H_{50}N_6NaO_{12}$ (M+Na)$^+$ 937.3. found 937.4.

(S)-(2R,3R,4R,5R)-2-(6-amino-9H-purin-9-yl)-5-((bis(4-methoxyphenyl) (phenyl)methoxy)methyl)-4-hydroxytetrahydrofuran-3-yl 3-(4-benzoylphenyl)-2-((tert-butoxycarbonyl)amino)propanoate (Boc-Bzf-(DMT)-A, 3i)

THF (3.5 mL) and DIPEA (44 mg, 60 μL, 0.35 mmol) were added to Boc-Bzf-OCH$_2$CN (70 mg, 0.17 mmol), (DMT)-A (50 mg, 89 μmol) and TBAAc (5 mg, catalyst) and stirred for 16 h. The solvent was removed under reduced pressure and SiO$_2$ flash chromatography (75%-100% ethyl acetate in hexanes) afforded 66 mg of a white solid in 81% yield. Rf 0.3 in 100% ethyl acetate; $^1$H and $^{13}$C NMR for 3i shown in FIG. 14; LRMS (ESI) m/z calcd for $C_{52}H_{52}N_6NaO_{10}$ (M+Na)$^+$ 943.4. found 943.5.

The following Boc-, DMT-protected donor molecules were synthesized using a general procedure similar to that used to synthesize 3i:

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-4-(methylthio)butanoate (Boc-Met-(DMT)-A, 3j)

(R)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-(methyldisulfanyl)propanoate (Boc-Csm-(DMT)-A, 3k)

(R)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-3-(isopropyldisulfanyl)propanoate (Boc-Csp-(DMT)-A, 3l)

(S)-(2R,3R,4R,5R)-2-(6-amino-9H-purin-9-yl)-5-((bis(4-methoxyphenyl)(phenyl)methoxy)methyl)-4-hydroxytetrahydrofuran-3-yl 2-((tert-butoxycarbonyl)amino)-4-(methyldisulfanyl)butanoate (Boc-Hcm-(DMT)-A, 3n)

Mass Spectrometry Characterization Data

| Donor Molecule | LRMS (ESI) m/z calcd for $(M + H)^+$, found |
|---|---|
| Boc-Met-(DMT)-A, 3j | 801.3, 801.5 |
| Boc-Csm-(DMT)-A, 3k | 819.3, 819.4 |
| Boc-Csp-(DMT)-A, 3l | 847.3, 847.4 |
| Boc-Hcm-(DMT)-A, 3n | 833.3, 833.4 |

(S)-(2R,3R,4R,5R)-2-(6-Amino-9H-purin-9-yl)-4-hydroxy-5-(hydroxymethyl)tetrahydrofuran-3-2-amino-3-phenylpropanoate (Phe-A, 4a)

3a (50 mg) was dissolved in 1 mL of THF and 1 mL trifluoroacetic acid (TFA) and reacted overnight with four equivalents of TIPSH. Upon addition of TFA, the reaction turned a bright-orange color and at the completion of the reaction, the color had become a dark brown. The reaction mixture was reduced to dryness by rotary evaporation and extracted using 1 mL dichloromethane and 1 mL water twice with a 1 mL water final back-extraction against the dichloromethane layer. The water-soluble layer containing 4a was then HPLC-purified on a C18-prep column using an increasing acetonitrile gradient (Gradient 2: 1-100% acetonitrile with water and 0.1% TFA, 1% per min) to remove any protected material. Prep. HPLC purified to give 13.6 mg (53.5%) of a white solid after evaporation. MALDI MS ceded m/z for $C_{19}H_{22}N_6O_5H$ $(M+H)^+$ 415.4, $C_{19}H_{22}N_6O_5Na$ $(M+Na)^+$ 437.4. found 415.0, 437.0.

(S)-(2R,3R,4R,5R)-2-(6-amino-9H-purin-9-yl)-4-hydroxy-5-(hydroxymethyl)tetrahydrofuran-3-yl 2-amino-4-methylpentanoate (Leu-A, 4b)

Trifluoroacetic acid (1 mL), tetrahydrofuran (1 mL) and TIPSH (99 mg, 0.13 mL, 0.63 mmol) were added to 3b (123 mg, 0.157 mmol) following the general deprotection procedure. HPLC/MALDI analysis m/z calcd $C_{16}H_{25}N_6O_5$ $(M+H)^+$ 381.2; Gradient 2 as described elsewhere herein; retention time 14.9 min. found 381.1; retention time 16.6 min. found 381.1.

(S)-(2R,3R,4R,5R)-2-(6-amino-9H-purin-9-yl)-4-hydroxy-5-(hydroxymethyl)tetrahydrofuran-3-yl 2-amino-3-(4-azidophenyl)propanoate (Azf-A, 4c)

Trifluoroacetic acid (1 mL), tetrahydrofuran (1 mL) and TIPSH (33 mg, 42 µL, 0.21 mmol) were added to 3c (44 mg, 52 µmol) following the general deprotection procedure. HPLC/MALDI analysis m/z calcd $C_{19}H_{22}N_9O_5$ $(M+H)^+$ 456.2; Gradient 2 as described elsewhere herein; retention time 19.6 min. found 456.1; retention time 21.1 min. found 456.1.

(S)-(2R,3R,4R,5R)-2-(6-amino-9H-purin-9-yl)-4-hydroxy-5-(hydroxymethyl)tetrahydrofuran-3-yl 2-amino-3-(naphthalen-2-yl)propanoate (Nap-A, 4d)

Trifluoroacetic acid (1 mL), tetrahydrofuran (1 mL) and TIPSH (26 mg, 0.34 mL, 0.17 mmol) were added to 3d (36 mg, 41 µmol) following the general deprotection procedure. HPLC/MALDI analysis m/z calcd $C_{23}H_{25}N_6O_5$ $(M+H)^+$ 465.2, $C_{23}H_{24}N_6O_5Na$ $(M+Na)^+$ 487.2; Gradient 2 as described elsewhere herein; retention time 21.9 min. found 464.6, 486.6; retention time 23.4 min. found 464.6, 486.6.

(S)-(2R,3R,4R,5R)-2-(6-amino-9H-purin-9-yl)-4-hydroxy-5-(hydroxymethyl)tetrahydrofuran-3-yl 2-(methylamino)-3-phenylpropanoate (Mef-A, 4e)

Trifluoroacetic acid (1 mL), tetrahydrofuran (1 mL) and oxalic acid (2.9 mg) were added to 3e (31 mg, 37 µmol) following the general deprotection procedure. No TIPSH was used in this reaction. HPLC/MALDI analysis m/z calcd $C_{20}H_{25}N_6O_5$ $(M+H)^+$ 429.2, $C_{20}H_{24}N_6O_5Na$ $(M+Na)^+$ 451.2; Gradient 2 as described elsewhere herein; retention time 16.3 min. found 429.1; retention time 18.6 min. found 429.1, 451.1.

(S)-(2R,3R,4R,5R)-2-(6-amino-9H-purin-9-yl)-4-hydroxy-5-(hydroxymethyl)tetrahydrofuran-3-yl 2-acetamido-3-phenylpropanoate (Acf-A, 4f)

During HPLC analysis, 3f was directly deprotected to 4f by exposure to the 0.1% TFA in the HPLC solvent and confirmed via MALDI. HPLC/MALDI analysis m/z calcd $C_{21}H_{25}N_6O_6$ $(M+H)^+$ 457.2, $(M+Na)^+$ $C_{21}H_{24}N_6NaO_6$ 479.2; Gradient 2 as described above; retention time 18.2 min. found 457.3, 479.3; retention time 19.5 min. found 457.3, 479.3.

(S)-(2R,3R,4R,5R)-2-(6-amino-9H-purin-9-yl)-4-hydroxy-5-(hydroxymethyl)tetrahydrofuran-3-yl 2-azido-3-phenylpropanoate ($N_3$f-A, 4g)

Trifluoroacetic acid (1 mL) and TIPSH (21 mg, 30 µl, 0.13 mmol) were added to 3g (25 mg, 33 µmol) following the general deprotection procedure. HPLC/MALDI analysis m/z calcd $C_{19}H_{21}N_8O_5$ $(M+H)^+$ 441.2, $C_{19}H_{20}N_8NaO_8$ $(M+Na)^+$ 463.1; Gradient 2 as described elsewhere herein; retention time 24.5 min. found 440.9, 462.9; retention time 24.7 min. found 440.9, 462.9

(S)-(2R,3R,4R,5R)-2-(6-amino-9H-purin-9-yl)-4-hydroxy-5-(hydroxymethyl)tetrahydrofuran-3-yl 2-amino-3-(7-methoxy-2-oxo-2H-chromen-4-yl)propanoate (Mcm-A, 4h)

Trifluoroacetic acid (1 mL), tetrahydrofuran (1 mL) and oxalic acid (3.9 mg) were added to 3e (31 mg, 37 µmol) following the general deprotection procedure, except was worked up in water only and water-soluble portion was HPLC purified. No TIPSH was used in this reaction. HPLC/MALDI analysis m/z calcd $C_{23}H_{25}N_6O_8$ (M+H)$^+$ 513.2, $C_{23}H_{24}N_6O_8Na$ (M+Na)$^+$ 535.2; Gradient 2 as described elsewhere herein; retention time 19.9 min. found 513.1, 535.1; retention time 20.9 min. found 513.1, 535.1.

(S)-(2R,3R,4R,5R)-2-(6-amino-9H-purin-9-yl)-4-hydroxy-5-(hydroxymethyl)tetrahydrofuran-3-yl 2-amino-3-(4-benzoylphenyl)propanoate (Bzf-A, 4i)

TFA (1 mL) and TIPSH (40 mg, 50 µL, 0.26 mmol) were added to DMT-A benzoylphenylalanine (59 mg, 64 µmol) according the general deprotection procedure. HPLC/MALDI analysis m/z calcd $C_{26}H_{27}N_6O_6$ (M+H)$^+$ 419.2, $C_{26}H_{26}N_6NaO_6$ (M+Na)$^+$ 441.2; Gradient 2 as described elsewhere herein, retention time 19.7 min found 519.1, 541.1.

The following deprotected donor molecules were synthesized using a general procedure similar to that used to synthesize 4i:

(S)-(2R,3R,4R,5R)-2-(6-amino-9H-purin-9-yl)-4-hydroxy-5-(hydroxymethyl)tetrahydrofuran-3-yl 2-amino-4-(methylthio)butanoate (Met-A, 4j)

(R)-(2R,3R,4R,5R)-2-(6-amino-9H-purin-9-yl)-4-hydroxy-5-(hydroxymethyl)tetrahydrofuran-3-yl 2-amino-3-(methyldisulfanyl)propanoate (Csm-A, 4k)

(R)-(2R,3R,4R,5R)-2-(6-amino-9H-purin-9-yl)-4-hydroxy-5-(hydroxymethyl)tetrahydrofuran-3-yl 2-amino-3-(isopropyldisulfanyl)propanoate (Csp-A, 4l)

(S)-(2R,3R,4R,5R)-2-(6-amino-9H-purin-9-yl)-4-hydroxy-5-(hydroxymethyl)tetrahydrofuran-3-yl 2-amino-4-(methyldisulfanyl)butanoate (Hcm-A, 4n)

Mass Spectrometry Characterization Data

| Donor Molecule | LRMS (ESI) m/z calcd for (M + H)$^+$, found | HPLC Retention Time* for 2' and 3' isomers (min) |
| --- | --- | --- |
| Met-A, 4j | 399.1, 398.1 | 12.8, 13.8 |
| Csm-A, 4k | 417.1, 416.8 | 19.8, 21.9 |
| Csp-A, 4l | 445.1, 445.0 | 25.2, 28.5 |
| Hcm-A, 4n | 431.1, 430.5 | 23.0, 24.5 |

*Using Gradient 2

LysAlaAcm Ligation Assay

Each ligation reaction, 125 µL total volume, contained the following reagents: aminoacyl adenosine donor (1 mM), recombinant His10-tagged *E. coli* aminoacyl transferase (2.26 µM), and LysAlaAcm (100 µM) in the AaT Ligation Buffer (50 mM HEPES pH 8.0, 150 mm KCl, 10 mM $MgCl_2$). The reaction mixtures were incubated at 37° C. for four hours and quenched with 1% acetic acid. The proteins were extracted from the reactions via acetone precipitation. The reactions were precipitated using 4× reaction volume of acetone and cooled at −20° C. for 1 h. Next, the reactions were centrifuged at 13,200 rpm at 4° C. for 20 min to separate the reaction from precipitated protein. The supernatant was transferred to fresh 1.5 mL centrifuge tubes and allowed for acetone evaporation overnight at room temperature. After acetone evaporation, the supernatant was dried in a Speedvac (Savant, Thermo Scientific, Fisher Inc.) for 30 min to remove residual acetone. The resulting reaction volume was dissolved up to 1.2 mL using Milli-Q water and analyzed by HPLC (gradient below) to determine ligation yield by integration of separated peak intensities monitored at 325 nm. Collected HPLC fractions were characterized through MALDI MS analysis. Reactions were performed with 6 trials on at least two protein preparations for all successful reactions, 3 trials for failed reactions. Reactions using Phe-pd-CpA as donor were carried out in an identical fashion (Ellman, et al., 1991, Methods Enzymol. 202:301-336).

AspAlaAcm Ligation Assay

Ligation test reactions with *V. vulnificus* Bpt were conducted in a manner identical to the AaT LysAlaAcm ligation assay with the following exceptions, 2.26 µM BpT was used rather than 2.26 µM AaT, 100 µM AspAlaAcm was used rather than 100 µM LysAlaAcm, and BpT Ligation Buffer (50 mM HEPES, pH 8, 150 mM KO, 10 mM $MgCl_2$) was used rather than AaT Ligation Buffer.

A/AMP/ATP/pdCpA Inhibition Studies

Each ligation reaction was performed as described elsewhere herein. The addition of four types of adenosyl compounds (adenosine, AMP, ATP, or pdCpA) were monitored individually in ligation reactions with Phe donor 4a. Adenosyl compound concentrations tested were 1 mM, 2.5 mM, and 5 mM. HPLC analysis was used to determine inhibition of ligation by integration of HPLC reagent and product peaks. The LysAlaAcm ligation assay was used to analyze the kinetics of AaT with substrate 4a. The ligation assay was modified for ease of analysis as follows: The total reaction volume was scaled up to 590 µL and all reagents were maintained at the same concentrations as mentioned above, Five concentrations of 4a were monitored for a total reaction time of 30 min, with concentrations ranging from 0.05 to 1 mM.

Each 30 min kinetic experiment was done in triplicate with a total of fourteen 40 µL aliquots for all substrate concentrations. The synthesis of pdCpA was carried out essentially as previously described (Ellman, et al., 1991, Methods Enzymol. 202:301-336).

AaT Ligation Reaction Analysis by HPLC

All HPLC analyses of LysAlaAcm ligations were monitored on an Agilent HPLC using a Waters C18 column (Milford, Mass.). The solvents used for peptide purification were the following: 0.1% trifluoroacetic acid in water (Solvent A) and 0.1% trifluoroacetic acid in acetonitrile (Solvent B), The HPLC method had the following solvent gradient (Gradient 1): 0 min 1% B, 5 min 1% B, min 30% B, 15 min 40% B, 20 min 100% B, 25 min 100% B, 27 min B, 30 min 1% B. Peptides were monitored at two absorption wavelengths during HPLC analysis, 215 nm for peptide absorption, and 325 nm for ACM absorption. MALDI MS analyses confirmed identity of peptide, Xaa-A donor, and ligated products.

Fluorometric Analysis of Transferase Experiments

Real time fluorescent monitoring of Nap addition to LysAlaAcm was carried out using reaction solutions prepared on the 500 µL scale in stirred quartz cuvettes with 1.00 cm path lengths. Reagent concentrations were as described elsewhere herein, except that donor 4d was withheld until the cuvette was placed in the fluorometer and temperature equilibrated.

Reactions were then initiated by addition of 20 μL of 25 mM Nap-A (4d) stock or water (for negative controls). Fluorescence emission at 390 nm was monitored after excitation at 325 nm. Prior calibration had shown that NapLysAlaAcm (5d) concentrations could be estimated from fluorescence intensity readings ($F_{5d}$) using the equation $$[5d]=(1-(F_{5d}/F_{Control}))1.39[LysAlaAcm],$$

where $f_{Control}$ is the fluorescence reading of the reaction with water added instead of 4d. Calibration details are given in Supporting Information. Measurements were taken on the Cary Eclipse fluorometer in the "Kinetics" mode at 37° C., acquiring data every 1.5 s. The excitation and emission slit widths were 5 nm and the averaging time was 1 s.

α-Casein N-Terminal Modification

α-Casein (4.8 mg) was modified with Azf-A (4c) in a reaction volume of 1 mL in modified AaT buffer (50 mM. HEPES pH 8.0, 1.50 mM KO, 10 mM $MgCl_2$) and AaT (0.05 mg). The reaction mixture was incubated at 37° C. for 12 h, AaT was removed using $Ni^{2+}$ resin (Ni-NTA Superflow, Qiagen), and then buffer exchanged four times into phosphate buffered saline (PBS, 12 mM $NaH_2PO_4$, 50 mM NaCl, 4.7 mM KCl, pH 8.0) by Spectra/Por 1 dialysis tubing (Spectrum Laboratories; Rancho Dominguez, Calif.). Azf-modified α-casein was used directly after buffer exchange into PBS. Aliquots (1 nmol) of α-casein were diluted into PBS (22 μL) containing either fluorescein-alkyne (FlAlk, 91 μM) or propargylamine (Alk, 227 μM) for copper-catalyzed azide-alkyne cycloaddition (CuAAC). The CuAAC reaction was initiated by addition of $CuSO_4$ (100 μM), tris-(3-hydroxypropyltriazolylmethyl)amine (THPTA, 500 μM), and sodium ascorbate (5 mM). For control reactions, equivalent volumes were replaced with either PBS or water. The reaction mixtures were incubated at 4° C. for 2 h. Reactions were boiled with gel loading dye LDS (Pierce; Rockford, Ill.) for 10 min at 95° C. and analyzed by SDS-PAGE. Fluorescence images were obtained with a Geldoc (BioRAD; Hercules, Calif.) using an excitation wavelength of 302 nm for detection of fluorescein. α-Casein was also directly visualized by Coomassie Brilliant Blue staining.

Tryptic Digest Analysis of α-Casein Modification

α-Casein-Azf (33 or α-casein (33 μg) was digested with sequencing grade modified Trypsin (0.6 μg) in 27 μL of 25 mM ammonium bicarbonate pH 7.5 (freshly prepared). Digestions were carried out at 37° C. for 14 h. Trypsin digest aliquots (1 μL) were combined with α-cyano-4-hydroxycinnamic acid (1 μL of a saturated solution in 1:1 $H_2O/CH_3CN$ with 1% TFA) and analyzed by MALDI MS.

α-Casein Labeling in Cleared Cell Lysate.

AaT was expressed in E. coli BL21-Gold (DE3) cells as previously described. A cleared cell lysate was obtained by centrifugation following cell lysis using sonication. Protein were modified in a final reaction volume of 110 μL with Azf-A (4c, 3 mM) using AaT (25 from cleared lysate in AaT buffer (50 mM HEPES pH 8.0, 150 mM KCl, 10 mM $MgCl_2$). α-Casein (0.012 mg or 0.12 mg) was added to the reaction and incubated at 37° C. for 2 h, after 1 h an additional 0.3 μmole of 4c was added. For control reactions, equivalent volumes were replaced with water. Excess 4c was removed by buffer exchange four times against phosphate buffered saline (PBS, 12 mM $NaH_2PO_4$, 50 mM NaCl, 4.7 mM. KCl, pH 8.0) by Spectra/Por 1 dialysis tubing. Aliquots (18 μL) of 4c modified lysates were diluted to a final volume of 22 μL using PBS containing FlAlk (182 μM) for copper-catalyzed "click" reactions. The "click" reaction was initiated by addition of $CuSO_4$ (100 μM), THPTA (500 μM), and sodium ascorbate (5 mM). The reaction mixtures were analyzed by PAGE gel using Coomassie staining and fluorescence as above.

HPLC Analysis of Donor Deprotection.

Figure 15:
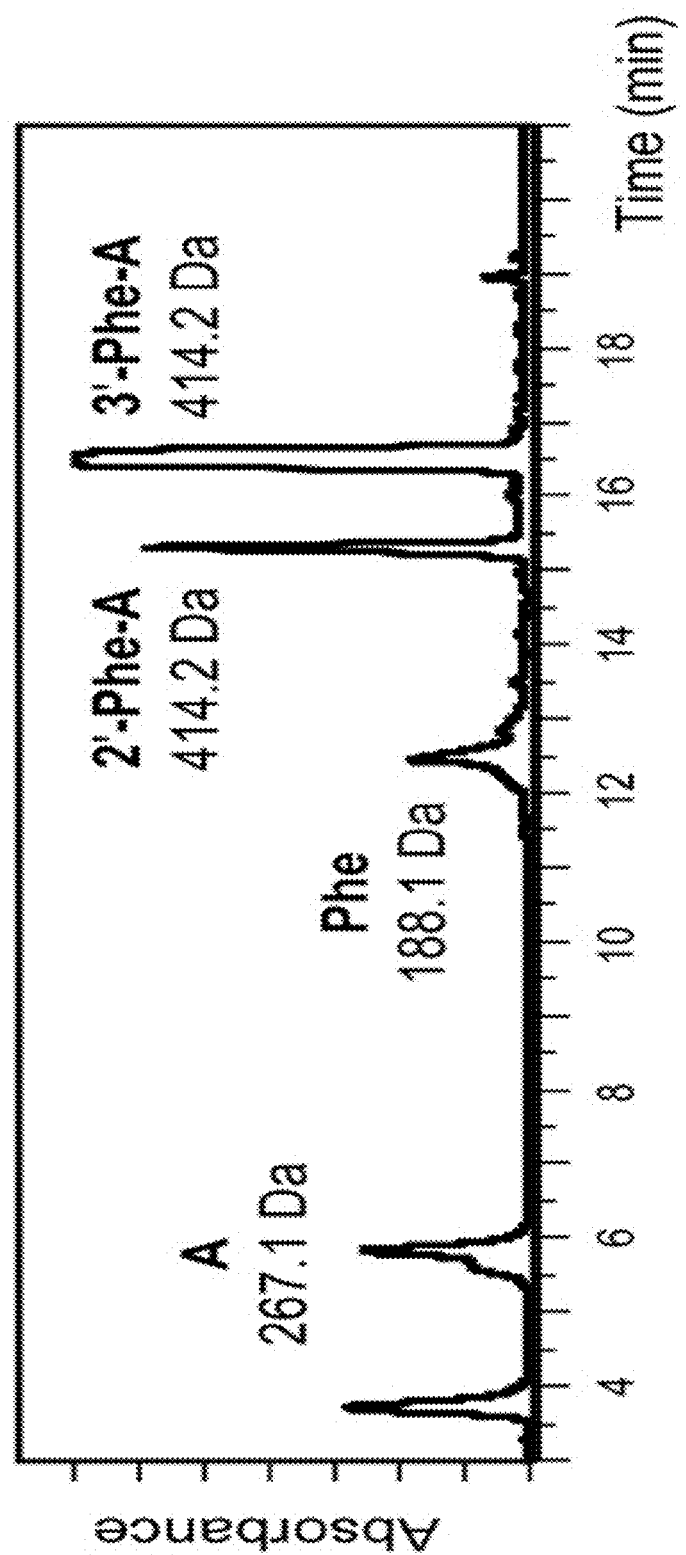
FIG. 15 is an image depicting the results of HPLC analysis of donor 4a purity after TFA deprotection.

Trifluoroacetic acid (1 ml) and TIPSH (10 mg, 13 μl, 65 μmol) were added to 3a (10 mg, 13 μmol) and stirred for 12 h. Solvent was removed under reduced pressure followed by precipitation with diethyl ether. HPLC analysis of the deprotection reaction is shown in FIG. 15. The assignment of the 2' and 3' acetylated forms of Phe-A was based on the known thermodynamic preference for 3' acylation of adenosine (Taiji, et al., 1983, Biochemistry 22:3220-3225). The HPLC method (Solvents A and B defined elsewhere herein) had the following solvent gradient (Gradient 3): 0 min 2% B, 60 min 100% B, 65 min 1% B. Monitored at 215 nm and 260 nm.

HPLC Analysis of Donor Hydrolysis.

Figure 16:
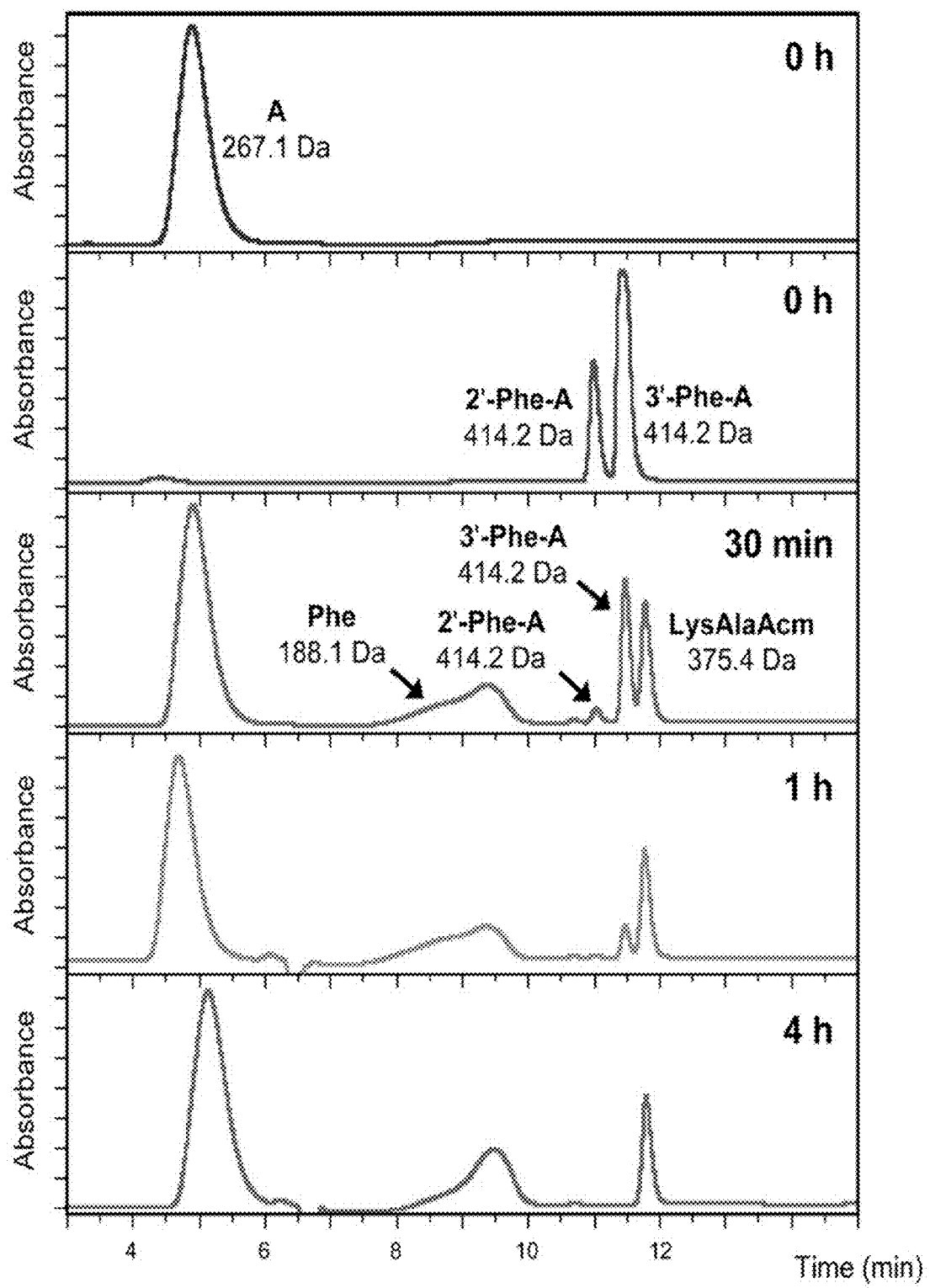
FIG. 16 is an image depicting the results of HPLC analysis of donor 4a hydrolysis in mock transferase reactions. Slight differences in retention time were observed, and compound identities were confirmed by MALDI MS.
Figure 17:
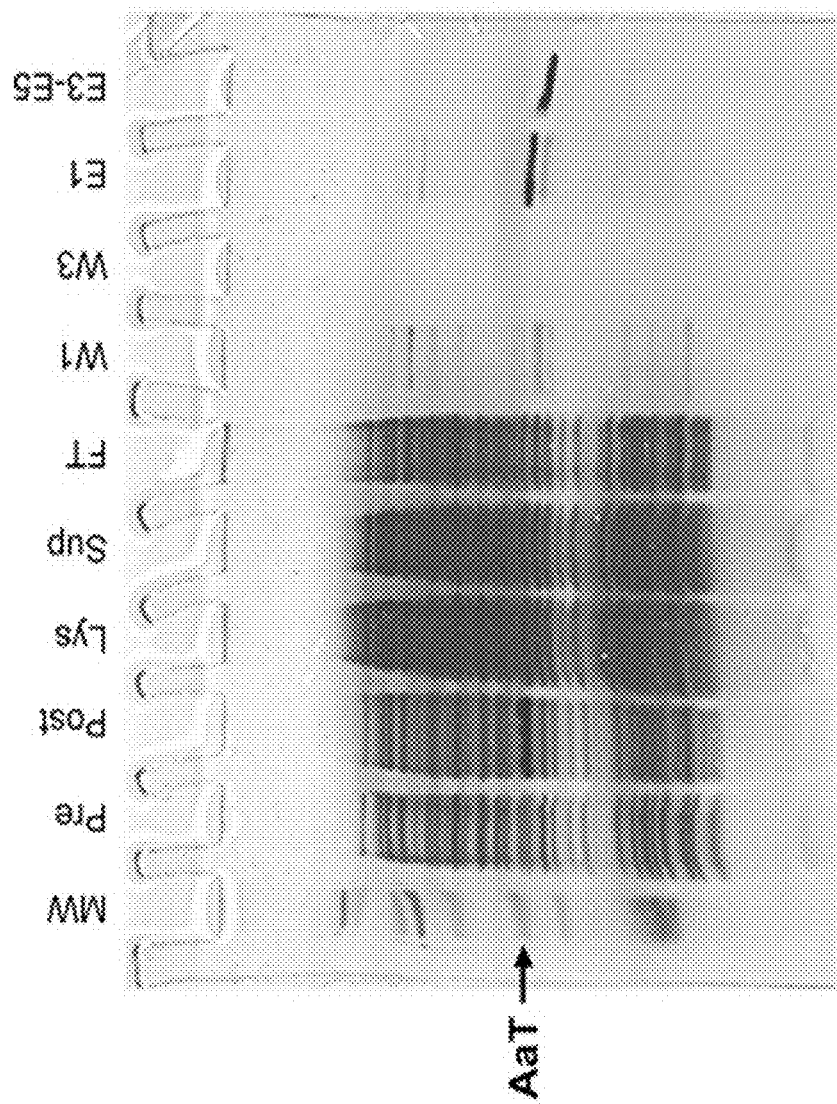
FIG. 17 is an image depicting PAGE gel analysis of AaT expression and purification. Lanes (left to right): 1) Molecular weight markers (Masses in kDa: 16, 25, 32, 47, 80, 100, 210); 2) Pre-induction; 3) Post-induction; 4) Crude cell lysate; 5) Supernatant after centrifugation; 6) Ni-NTA column flow-through; 7) Column wash 1; 8) Column wash 3; 9) Elution fraction 1; 10) Combined elution fractions 3-5 after overnight dialysis.

The amino acid analog donor (4a-4z) was suspected to be hydrolytically unstable and was tested in mock LysAlaAcm reactions without enzyme present and then analyzed by HPLC. The mock LysAlaAcm reactions were performed as described in the LysAlaAcm Ligation Assay section; however, the AaT solution was replaced with water. Phe-A solutions were analyzed at 30 min, 1 h, and 4 h. Immediately following the reaction, the sample was diluted to 1,200 μL and injected onto the C18 HPLC column using Gradient 1. As set forth in FIG. 16, Phe-A was completely hydrolyzed after 4 h. Additionally, 1 mM A and 1 mM Phe were injected on the HPLC to serve as standards to verify retention times. Note that the relative concentrations of 2' and 3' Phe-A would be different in an actual reaction where the 3' Phe-A is preferentially consumed by AaT in the transfer reaction (Watanabe et al., 2007, Nature 449:867-871). The change in 2':3' ratio between 0 h and 30 min probably reflected the higher pH of the 30 min data (Taiji et al., 1983, Biochemistry 22:3220-3225).

AaT Expression and Purification.

E. coli AaT was expressed from the pEG6 plasmid in E. coli BL21-Gold (DE3) cells using a procedure adapted from Graciet et al (Graciet, et al., 2006, Proc Natl Acad Sci USA 103:3078-3083). E. coli were grown in a primary culture of 5 mL LB at 37° C. to $OD_{600}$ of 0.5 and then were rediluted into a secondary culture of 500 mL LB and grown to $OD_{600}$ of 0.6. AaT expression was induced using 0.1 mM isopropyl β-D-thiogalactoside and cells were grown at 25° C. for ~16 h. Cells were pelleted at 6,000 RPM using a GS3 rotor and Sorvall RC-5 centrifuge. Cell pellets were resuspended in the Ni-NTA binding buffer (50 mM Tris, 10 mM imidazole, 300 mM KCl, and 5 mM β-mercaptoethanol, pH 8.0) and included protease inhibitor cocktail, 1 mM PMSF, and 10 units/mL DNAse1-Grade II. Following resuspension, the cells were lysed using sonication. Soluble proteins were collected via centrifugation at 13, 200 RPM for 15 min. Collected soluble protein was gently shaken for 1 h at ambient temperature with Ni-NTA resin. The resin was prepared by rinsing with Ni-NTA binding buffer and then washed with four volumes of Ni-NTA wash buffer (50 mM Tris, 50 mM imidazole, 300 mM KCl, and 5 mM β-mercaptoethanol, pH 8.0). The proteins were eluted with elution buffer (50 mM Tris, 250 mM imidazole, 300 mM KCl, and 5 mM β-mercaptoethanol, pH 8.0). Pure elution fractions of E. coli AaT were dialyzed overnight in AaT buffer (50 mM Tris, 30% glycerol, 120 mM $(NH_4)_2SO_4$, 5 mM β-mercaptoethanol pH 8.0). The dialyzed enzymes were stored at −80° C. Protein concentrations were determined using the Bradford assay and a bovine serum albumin standard curve according to the manufacturer's instructions (Bradford, 1976, Anal Biochem 72:248-254).

BpT Expression and Purification.

*V. vulnificus* BpT was expressed from the pEG145 plasmid in *E. coli* BL21-Gold (DE3) cells using a procedure adapted from Graciet et al., 2006, Proc. Natl. Acad. Sci. USA 103: 3078-3083). *E. coli* were grown at 37° C. to $OD_{600}$ of 0.5-0.6, followed by incubation at 42° C. for 1 h and at 0° C. for 30 min. Expression was induced with 0.25 mM isopropyl β-D-thiogalactoside, and was carried out at 25° C. for 5 h. Cells were resuspended in the Ni-NTA binding buffer (0.3 M KCl/10 mM imidazole/5 mM β-mercaptoethanol/50 mM Tris, pH 8.0) containing protease inhibitors and disrupted by sonication. Soluble proteins were collected via centrifugation at 13,200 RPM for 15 min, and incubated for 1 h at 4° C. with Ni-NTA resin preequilibrated in the Ni-NTA binding buffer. The resin was washed with Ni-NTA binding buffer, followed by a second wash with the binding buffer plus 50 mM imidazole. The proteins were eluted with the Ni-NTA binding buffer plus 0.25 M imidazole. Purified BpT was dialyzed against BpT buffer (10% glycerol/0.3 M KCl/15 mM β-mercaptoethanol/50 mM Tris, pH 8.0), and stored at −80° C. Protein concentrations were determined by using the Bradford assay.

AaT Ligation Reaction Analysis by HPLC.

All HPLC analyses of LysAlaAcm ligations were monitored as described elsewhere herein (Gradient 1). Peptide retention time monitored at 325 nm (Acm absorption) and MALDI MS analyses, confirming peptide identity are in Table 1.

TABLE 1

HPLC Analysis of LysAlaAcm Transfer Reactions.

| Peptide | Retention Time (min) | $(M + H)^+$ Mass Calcd, Found (m/z) |
|---|---|---|
| LysAlaAcm | 11.8 | 375.2, 374.9 |
| PheLysAlaAcm | 13.0 | 522.3, 522.1 |
| LeuLysAlaAcm | 12.7 | 488.3, 487.3 |
| AzfLysAlaAcm | 13.6 | 563.3, 563.3 |
|  |  | (—$N_2$ 537.3, 537.3) |
| NapLysAlaAcm | 14.1 | 572.3, 572.1 |
| MefLysAlaAcm | 13.1 | 536.3, 536.3 |
| AcfLysAlaAcm | NA | NA |
| $N_3$fLysAlaAcm | NA | NA |
| McmLysAlaAcm | NA | NA |
| BzfLysAlaAcm | 14.6 | 626.3, 626.1 |
| MetLysAlaAcm | 12.1 | 506.2, 506.1 |
| CsmLysAlaAcm | 12.2 | 524.2, 542.3 |
| CspLysAlaAcm | 13.1 | 552.2, 552.4 |
| HcmLysAlaAcm | 12.7 | 538.2, 538.1 |
| AspAlaAcm | 13.1 | 362.1, 362.1 |
| LeuAspAlaAcm | 13.9 | 475.2, 475.3 |
| CspAspAlaAcm | 14.1 | 539.2, 539.1 |
| AcMetAspValPheHcsLysAlaAcm | 17.9 | 1026.4, 1026.5 |

Calibration of NapLysAlaAcm Fluorometric Transfer Analysis.

In order to monitor conversion of LysAlaAcm to NapLysAlaAcm (5d) in real time, a fluorometric assay was designed based on intramolecular quenching of aminocoumarin fluorescence by the naphthyl ring. Equimolar solutions of LysAlaAcm and NapLysAlaAcm, as well as mixtures of the two solutions, were prepared and their fluorescence was compared as depicted in FIG. 18A. The fluorescence emission of NapLysAlaAcm at 390 nm ($\lambda_{ex}$=325 nm) was 72% lower than LysAlaAcm, and no non-linear effects were exhibited in the mixtures as depicted in FIG. 18B. Therefore, the mole fraction of NapLysAlaAcm could be linearly related to the measured fluorescence of a reaction solution ($F_{5d}$), and the concentration of 5d determined as $$(1-(F_{5d}/F_{Control}))\cdot 1.39 \cdot [LysAlaAcm],$$

where $F_{Control}$ is the fluorescence reading of the reaction with water added instead of donor 4d. This calibration was used to determine the time-dependent concentration of the NapLysAlaAcm product as described elsewhere herein.

Michaelis-Menten Kinetic Analysis of Phe Transfer.

The reaction scheme for the catalysis of N-terminal aminoacylation by AaT is shown in Equation 1. Previously, it has been shown that the sequential bisubstrate AaT reaction can be treated as pseudo-first order when carried out with saturating concentrations of one substrate (acceptor peptide) (Abramochkin et al., 1996, J. Biol. Chem. 271:22901-22907). Therefore, the reaction was characterized in terms of the Michaelis-Menten kinetic scheme in Equation 2.

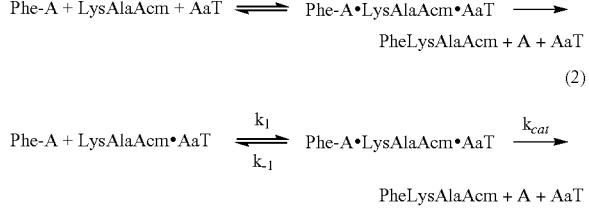

Figure 19:
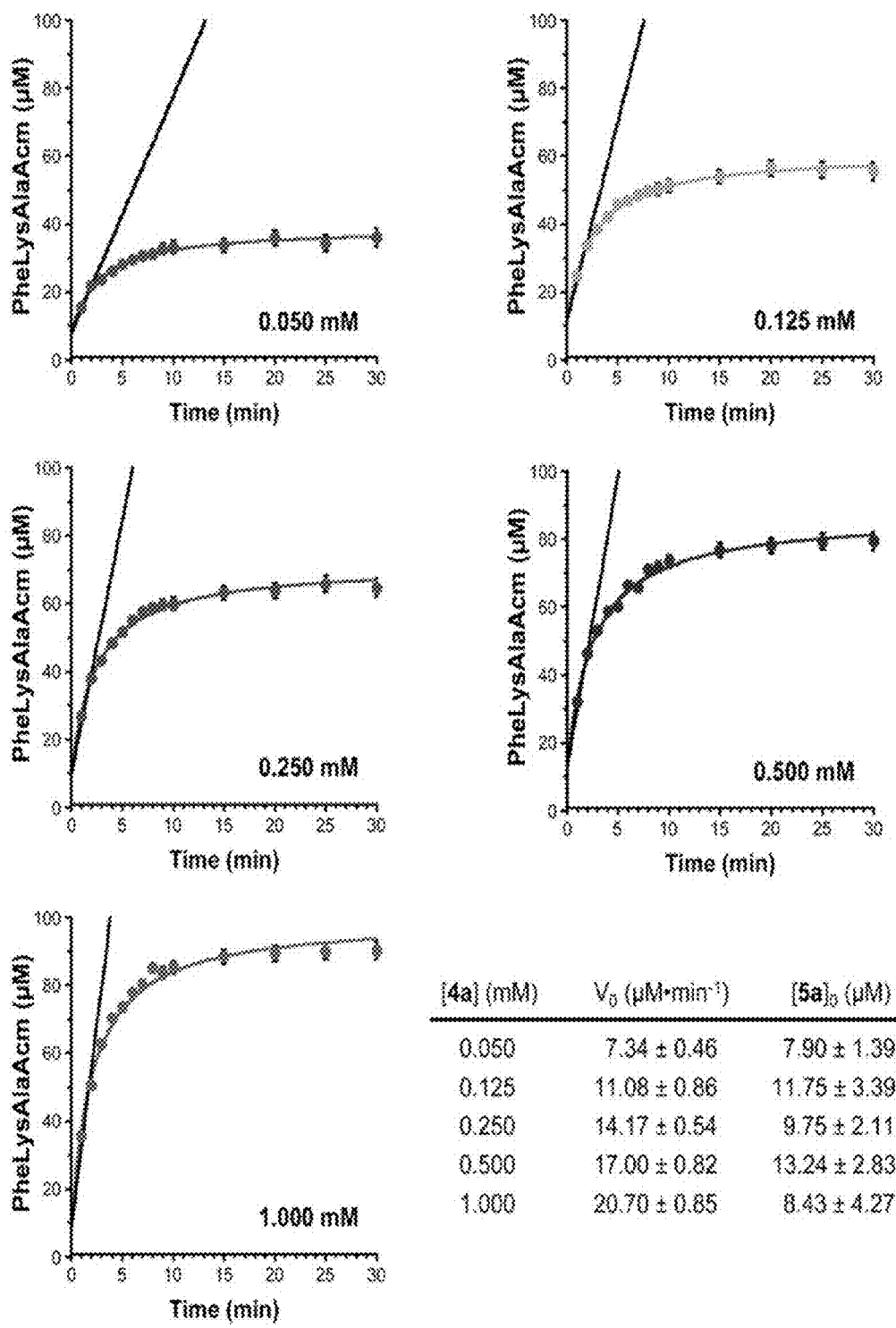
FIG. 19 is a series of images illustrating Phe transfer reaction kinetics. Product concentration as a function of time was determined by integrating HPLC traces. Data were an average of 3 trials. Bars indicated standard error. Black lines indicated best fit to early time points using Equation 4. Bottom Right: Fits to kinetic data according to Equation 4.

To determine initial velocities, the primary kinetic data is fit to the hyperbolic Equation 3, which, though phenomenological, produces a high quality fit (R>0.99 for all 5 data sets). Data from the first two minutes were fit to a linear expression (Equation 4). A non-zero intercept is employed for improved quality of fit; this can be justified in terms of a rapid burst phase not captured in the 1 min resolution of this assay. Note that this burst phase seems to be extremely rapid, even the 15 s intervals of the present direct fluorometric assay are not sufficient to capture this phase as depicted in FIG. 3A. The results of these linear fits are shown in FIG. 19.

$$[PheLysAlaAcm]=c_1 t/(c_2+t) \text{ or } [5a]=c_1 t/(c_2+t) \quad (3)$$

$$[PheLysAlaAcm]=[PheLysAlaAcm]_0+V_0 t \text{ or } [5a]= [5a]_0+V_0 t \quad (4)$$

The initial velocities were then plotted as a function of Phe-A donor concentration and fit to Equation 5 to obtain $k_{cat}$ and $K_M$ values, where $K_M=(k_{-1}+k_{cat})/k_1$ as depicted in FIG. 3B.

$$V_0=k_{cat}[AaT][Phe-A]/(K_M+[Phe-A]) \text{ or } V_0=k_{cat}[AaT][4a]/(K_M+[4a]) \quad (5)$$

Edman Degradation Analysis of α-Casein Modification

Phe was ligated to α-casein using 4a as described elsewhere herein with the following modifications. The substrate (1 mM) was 10 times more concentrated, and the total volume was 4 times greater. This reaction was run overnight; at the 4 h timepoint, an additional 50 μL dose of 25 mM 4a donor was added to the reaction. The $His_{10}$-tagged AaT was separated from the reaction via nickel bead purification: 100 μL Ni-NTA resin was added at a ratio of 25 jut per 12.5 μM AaT, the beads were shaken with the reaction for 2 hours, then separated via centrifugation at 13,200 RPM for 2 min. The supernatant was removed, diluted to 1 mL with Milli-Q water, and dialyzed against 1×PBS (Hyclone, Fisher) overnight at 4° C.

to remove any residual 4a. The protein was electroblotted onto PVDF membrane and Edman Degradation analysis was conducted.

"Click" Reagent Synthesis

Fluorescein 5- and 6-propargylamide (Fluorescein-alkyne, FlAlk) was synthesized as previously described (Wang et al., 2003, J. Am. Chem. Soc. 125:3192-3193). Briefly, propargylamine (8.7 µL, 136 µmol) was added to a solution of 5- and 6-Carboxyfluorescein N-hydroxysuccinimide ester (32 mg, 68 µmol) in tetrahydrofuran (5 mL). The reaction was stirred continuously and monitored by TLC. Solvent was removed by under reduced pressure. Purification by silica chromatography ($R_f$=0.3, 20% MeOH in $CH_2Cl_2$) afforded fluorescein-alkyne as a red-orange solid.

Tris-(3-hydroxypropyltriazolylmethyl)amine (THPTA) was also synthesized as previously described (Hong et al., 2009, Angew. Chem. Int. Ed. 48:9879-9883). Briefly, a solution of 3-bromo-propanol (2 g, 14.4 mmol) in dichloromethane (10 mL) was added to $Ac_2O$ (2.94 g, 28.8 mmol) and $NEt_3$ (2.91 g, 28.8 mmol). The reaction was stirred continuously and monitored by TLC. An aqueous solution of $NaHCO_3$ was added and the phases were separated. The organic layer was washed once more with $NaHCO_3$ and twice with brine. Solvent was removed under reduced pressure and 3-bromopropyl acetate was afforded as a colorless oil.

A solution of 3-bromopropyl acetate (1.0 g, 6.0 mmol) in water (10 mL) was added to sodium azide (780 mg, 12.1 mmol). The solution was stirred at 90° C. overnight. The solution was extracted three times with 15 mL $CH_2Cl_2$ and dried with $MgSO_4$. Solvent was removed under reduced pressure to afford 3-azidopropyl acetate as a pale yellow oil. A solution of tripropargylamine (12.3 mg, 0.941 mmol) in tetrahydrofuran (6.5 mL) was added to 3-azidopropyl acetate (0.672 g, 4.71 mmol) and Cu(I) acetate (5.8 mg, 5 mol %). The solution was refluxed overnight under inert atmosphere. Solvent was removed under reduced pressure. Silica chromatography purification ($R_f$=0.5, 5-10% MeOH in $CH_2Cl_2$) afforded acetyl-protected THPTA as a yellow oil.

A solution of acetyl-protected THPTA (397 mg, 0.711 mmol) in 2.0 M ammonia in MeOH (10 mL) was continuously stirred overnight at 40° C. Solvent was removed under reduced pressure. The solid was washed and filtered four times with acetonitrile and dried under reduced pressure to afford THPTA as a white solid.

For both FlAlk (25% overall yield) and THPTA (98% overall yield), intermediate and product identities were confirmed by comparison of 1H NMR and LRMS (ESI) MS data to previous reports (Wang, et al., 2003, J Am Chem Soc 125:3192-3193; Hong, et al., 2009, Angew Chem, Int Ed 48:9879-9883).

Peptide Synthesis and Thioester Formation

The AcMetAspValPhe peptide was synthesized using a manual, Fmoc-based solid-phase procedure on 2-chlorotrityl chloride resin (100-200 mesh; 0.6 mmol substitution/g). For each coupling, 5 equiv of amino acid, 5 equiv of HBTU, and 10 equiv of DIPEA in dimethylformamide (DMF) were stirred for 30 min at room temperature. After rinsing the resin three times with DMF, 20% piperidine in DMF was used to deprotect the Fmoc-group from the coupled amino acid. The deprotection solution was collected for UV analysis to quantify the coupling efficiency.

The N-terminus of the peptide was acetylated by two successive 10 min incubations with a capping solution of acetic anhydride, N-methylmorpholine, and DMF (5:3:42 v/v). In order to cleave the peptides from the resin while retaining the sidechain protecting groups, the capped N-terminal peptides were incubated for 1 h with acetic acid (AcOH), trifluoroethanol (TFE), and $CH_2Cl_2$ (1:1:8 v/v). The cleaved peptide solution was dried by rotary evaporation and rinsed with $CH_3CN$ three times to remove AcOH.

The crude peptide (1 equiv, 2 mM) was dissolved in tetrahydrofuran (THF), and thiophenol (3 equiv, 6 mM) was added to the solution. After stirring for 5 min, PyBOP (3 equiv, 6 mM) and DIPEA (3 equiv, 6 mM) were added to the reaction mixture. The solution was allowed to stir for 1 h at room temperature, at which point the solvent was removed by rotary evaporation. Sidechain protecting groups were removed by incubating the peptide for 1 h with a fresh cleavage cocktail of TFA, water, and TIPS with a composition of 16:3:1 (v/v) for thioamide-containing peptides and 38:1:1 (v/v) for all others. The cleavage solution was removed from the peptide by rotary evaporation, and the residue was rinsed with $CH_3CN$ twice and dried. The peptide thioester was purified by reverse-phase HPLC using a binary system of aqueous (Buffer A: water+0.1% TFA) and organic (Buffer B: $CH_3CN$+0.1% TFA) phases. After drying on a lyophilizer or in a vacuum centrifuge, the purified peptide thioester was analyzed by MALDI MS to confirm their identity; LRMS (ESI) m/z calcd for thiophenyl ester $C_{11}H_{19}N_2O_4S_2$ $(M+H)^+$ 645.2. found 645.2).

Peptide Ligation

The Ac-MetAspValPhe thioester (1 equiv, 0.5 µmol) and HcmLysAlaAcm (1 equiv, 0.5 µmol) were dissolved in a freshly made, argon-sparged ligation buffer (100 mM $Na_2HPO_4$, 20 mM DTT or TCEP, pH 7.0-7.2). A typical ligation began with the combination of the two peptide fragments in a 5 mL, septum-capped, and argon-purged round-bottom flask. The final volume of the reaction was 500 µL, giving a 1 mM final concentration of each peptide. The reaction mixture was sparged with argon for 15 mM and stirred under an argon atmosphere at room temperature. To monitor the ligation progress, aliquots (50 µL) were taken periodically at regular intervals and diluted to 800 µL with 0.1% TFA in water. Each sample was analyzed by analytical HPLC.

Synthesis of Synthetic Nucleoside Donors

The synthesis of adenosyl donor compounds, shown in Scheme 1, can be carried out on any amino acid with appropriate acid-labile protecting groups (e.g., N-Boc). This synthesis is not limited to α-amino acids, and the present donor synthesis has also enabled to test the transfer of analogs such as α-azidophenylalanine ($N_3$f, 4g). Conversion to the cyanomethyl ester (1a-z) is typically high-yielding, although yields for the subsequent acylation of 5'-O-dimethoxytrityl-adenosine ((DMT)-A) varied between 60 and 90%. Acylation yields generally decreased with side chain bulk; derivatives such as N-1,8-naphthyldiaminopropionic acid coupled poorly. Uncatalyzed reactions took 1-5 days, but in all cases, addition of tetrabutylammonium acetate increased reaction rates.

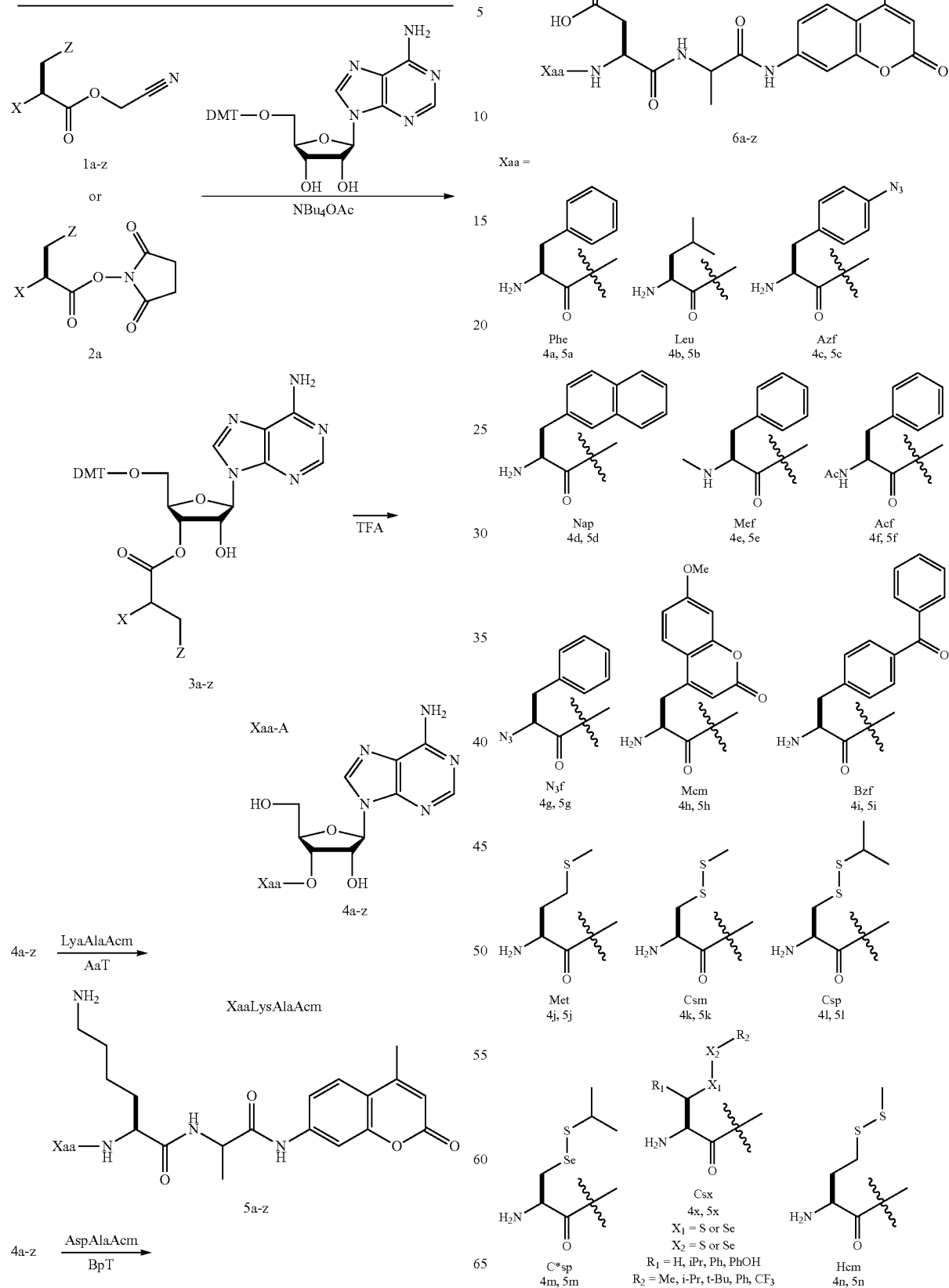

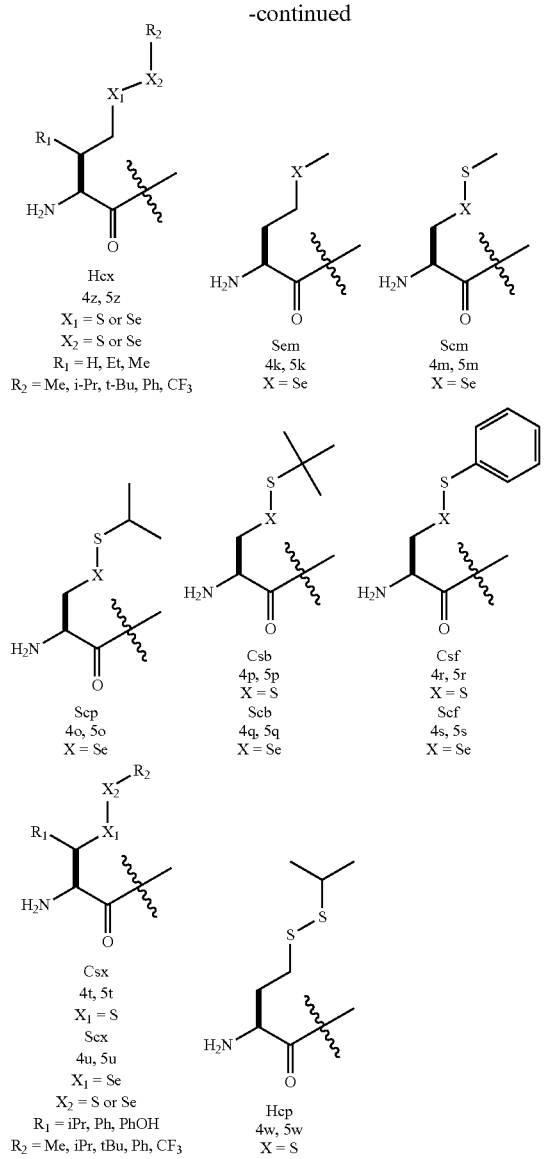

Scheme 1 Legend-Donor synthetic intermediates:
1a, 2a, 3a X = NHBoc, Z = Ph; 1b, 3b X = NHBoc, Z = i-Pr; 1c, 3c X = NHBoc, Z = p-Azidophenyl; 1d, 3d X = NHBoc, Z = 2-naphthyl; 1e, 3e X = NHMeBoc, Z = Ph; 1f, 3f X = NHAc, Z = Ph; 1g, 3g X = N$_3$, Z = Ph; 1h, 3h X = NHBoc, Z = 7-Methoxycoumarinyl; 1i, 3i X = NMeBoc, Z = p-Benzoylphenyl; 1j, 3j X = NHBoc, Z = CH$_2$SCH$_3$; 1k, 3k X = NHBoc, Z = SSCH$_3$; 1l, 3l X = NHBoc, Z = SSCH(CH$_3$)$_2$; 1m, 3m X = NHBoc, Z = SeSCH(CH$_3$)$_2$; 1x, 3x X = NHBoc, Z = variable; 1n, 3n X = NHBoc, Z = CH$_2$SSCH$_3$; 1z, 3z X = NHBoc, Z = variable.

(?) indicates text missing or illegible when filed

The Phe donor 4a was synthesized from both the cyanomethyl ester (1a) and N-hydroxysuccinimidyl (OSLO ester (2a). All other adenosyl donors were synthesized from the cyanomethyl ester (1b-z). After trifluoroacetic acid (TFA) deprotection and CH$_2$Cl$_2$ washing (or Et$_2$O precipitation) to remove DMT byproducts, the compounds were taken on directly to AaT enzymatic reactions (contaminants were limited to incompletely deprotected compounds which are not transferred by AaT). However, in most cases the deprotected adenosyl donor was purified by HPLC, and higher transfer yields were generally observed with these purified donors.

Transferase Reactions

The extent of transfer was evaluated by HPLC analysis of reactions with adenosyl donor, AaT or BpT, and an aminocoumarin-labeled reporter peptide (for AaT, LysAlaAcm was used as previously described by Tirrell and co-workers; for BpT, AspAlaAcm was used in an analogous fashion) (Connor et al., 2008, ChemBioChem 9:366-369). Monitoring LysAlaAcm or AspAlaAcm acylation in crude reaction mixtures using absorbance at 325 nm conveniently eliminates background due to other proteins and nucleic acids, although some non-natural amino acids such as naphthylalanine (Nap) and methoxycoumarinylalanine (Mcm) also absorb in this range. Example HPLC chromatograms from Phe ligations are shown in FIG. 2. LysAlaAcm starting material eluted at 11.8 min as depicted in FIG. 2A; hydrophobic products eluted at 12 to 15 min (PheLysAlaAcm 5a elutes at 13.0 min in FIG. 2B, NapLysAlaAcm 5d elutes at 14.1 min in FIG. 2D).

To evaluate substrate scope, reactions were analyzed after 4 h, when transfer should be complete for the fully enzymatic reaction with Phe tRNA synthetase (Connor et al., 2008, ChemBioChem 9:366-369). Phe (4a) and Leu (4b) were transferred efficiently as shown in Table 2. The present PheLysAlaAcm yields from donor 4a were comparable to yields from Phe-pdCpA, the dinucleotide used by Sisido. Transfer yields for other substrates varied with side chain size, where Mcm (4h) is too large and benzoylphenylalanine (Bzf, 4i) is a poor substrate as shown in Table 2. Sisido has shown that AaT mutants can use substrates with larger side chains; some of these mutations are currently explored (Taki et al., 2008, ChemBioChem 9:719-722). While transfer yields after 4 h varied, most reactions could be driven to completion by a bolus of donor molecule as depicted in FIG. 2C.

One of the advantages of adenosyl donors over in situ tRNA aminoacylation with a tRNA synthetase is that it is not limited by the substrate specificity of the synthetase. In particular, non-amino acid substrates can be attached to adenosyl donors to assess their transferability by AaT. N-Methyl phenylalanine (Mef, 4e) was transferred, albeit with low yield. N-acetyl phenylalanine (Acf, 4f) and α-azidophenylalanine (4g) have also been tested and found to be poor substrates. In some experiments, substantial conversion of LysAlaAcm was found when incubated with 4g, but MALDI MS analysis has shown the product to be 5a, presumably obtained by transfer of Phe after prior reduction (i.e., Phe donor 4a was formed from 4g under the reaction conditions). Steps taken to alter the concentration of β-mercaptoethanol reductant did not improve the yield of 5g. It is believed that disproportionation of the azide was incomplete, but that AaT was selective for the α-amine substrate (Phe-A, 4a), so far more 5a than 5g was formed. Without wishing to be bound by any particular theory, it is believed that this may be due to an important interaction of the α-amine with Q1.88, which also acts as a catalytic base to deprotonate the peptide substrate for amide bond formation. The Q188/α-amine interaction was defined by the structural and enzymological work of Watanabe and co-workers (Watanabe et al., 2007, Nature 449:867-871). It is noted that the preference of AaT for unmodified N-termini was previously documented with full-length tRNA by Soffer and Leibowitz, (Leibowitz, et al., 1971, J. Biol. Chem. 246: 5207-5212).

TABLE 2

N-Terminal Modification of LysAlaAcm Reporter Peptide by AaT after Single Addition of Adenosyl Donor[a]

| Donor | Additives | Ligated Product Yield (%)[b] |
|---|---|---|
| 4a (Phe) | | 92.7 ± 5.2 |
| 4a (Phe) | 1 mM pdCpA | 90.4 ± 0.9 |
| 4b (Leu) | | 80.4 ± 0.9 |
| 4c (Azf) | | 78.5 ± 5.2 |
| 4d (Nap) | | 95.4 ± 0.4 |
| 4d (Nap) | 100 µM PheLysAlaAcm | 93.8 ± 0.3 |
| 4e (Mef) | | 0.6 ± 0.1 |
| 4f (Acf) | | 5f not observed |
| 4g (N₃f) | | 5g not observed[c] |
| 4h (Mcm) | | 5h not observed |
| 4i (Bzf) | | 9.2 ± 0.3 |
| 4j (Met) | | 21.9 |
| 4k (Csm) | | 20.1 |
| 4l (Csp) | | 42.3 |
| 4n (Hsm) | | 27.8 |

[a]Standard AaT-catalyzed transfer conditions with or without potential inhibitor added. See description under Experimental Procedures.
[b]Yield determined by integration of HPLC chromatogram peak areas at 325 nm, described in Experimental Procedures. Standard deviations are reported for an average of at least 6 experiments with at least 2 different AaT preparations.
[c]HPLC and MALDI MS analysis indicate that the observed product is 5a not 5g.

TABLE 3

N-Terminal Modification of AspAlaAcm Reporter Peptide by AaT after Single Addition of Adenosyl Donor[a]

| Donor | Additives | Ligated Product Yield (%)[b] |
|---|---|---|
| 4b (Leu) | | 5 |
| 4l (Csp) | | 20 |

[a]Standard BpT-catalyzed transfer conditions with or without potential inhibitor added. See description under Experimental Procedures. All other analogs yielded no substantial transferred product.
[b]Yield determined by integration of HPLC chromatogram peak areas at 325 nm, described in Experimental Procedures.

Evaluation of AaT Reactions

To better understand limitations on the yield from AaT reactions, the possibilities of inhibition by hydrolyzed substrate or aminoacylated product were assessed. Since the acyl adenosine donor substrate is not regenerated during the reaction (unlike the aaRS/tRNA/AaT reaction), it was hypothesized that the adenosine byproduct might inhibit further acylation by binding to AaT. To investigate this possibility, adenosine was added to the reaction at varying concentrations and monitored the reaction timecourse by fluorescence spectroscopy and by HPLC. Addition from the Phe donor 4a was not inhibited by the addition of 5 mM concentrations of adenosine as shown in Table 2. A comparison of adenosine compounds, including pdCpA, the dinucleotide donor used by Sisido, showed that only adenosine triphosphate (ATP) inhibited the reaction.

The present experiment was also achieved to monitor product formation in real time based on partial quenching of coumarin fluorescence upon addition of Nap to the LysAlaAcm peptide to form 5d. The fluorescence intensity at 390 nm of NapLysAlaAcm is 28% of the fluorescence of LysAlaAcm, and the overall fluorescence of mixtures of the two peptides can be used to determine the proportions of each peptide if the total concentration is known. Thus, the change in fluorescence intensity was used to monitor NapLysAlaAcm formation in real time, and HPLC injection of the reaction end points were used to confirm the final product distribution. It was found that exogenous adenosine did not significantly inhibit the reaction, even at concentrations up to 1 mM as shown in FIG. 3A.

The possibility of product inhibition by the aminoacylated LysAlaAcm product was also been assessed. In the present standard 4 h transfer assay, addition of 100 µM (1 equiv) PheLysAlaAcm did not significantly inhibit production of NapLysAlaAcm (5d) when Nap-A (4d) was used as a donor. Results from MALDI MS analysis and differences in HPLC retention time (Table 1) allowed for the ability to distinguish LysAlaAcm and PheLysAlaAcm from NapLysAlaAcm as depicted in FIG. 2 and Table 1.

The next experiments were designed to assess whether donor hydrolysis slowed reaction rates after 30-60 min. Analysis of mock reactions lacking transferase or LysAlaAcm indicates that donor hydrolysis may contribute significantly to slowing reactions, which is why a donor bolus can be used to drive the reaction to completion.

To characterize the enzymatic activity of AaT toward the present acyl adenosyl substrates, an HPLC assay was used to determine initial reaction rates to be fit to a standard Michaelis-Menten kinetic model. Equations describing this kinetic analysis are included elsewhere herein. Since adenosine does not inhibit the enzyme, by keeping LysAlaAcm concentrations high (100 µM), the rate of transfer was measured as a function of the concentration of Phe donor 4a and fits to a single-substrate kinetic model to be determined as a $k_{cat}$ of $1.68 \pm 0.09 \times 10^{-1}$ s$^{-1}$ and a $K_M$ of $1.24 \pm 0.23 \times 10^{-4}$M. The enzyme efficiency ($k_{cat}/K_M=1.35 \times 10^3$M$^{-1}$s$^{-1}$) was relatively low (Fersht, 1998, Structure and Mechanism in Protein Science: A Guide to Enzyme Catalysis and Protein Folding, 3rd ed.). While $K_M$ was higher for Phe-A than what Shrader reported for aminoacyl tRNA$^{Leu-4}$ (0.3 µM, the $k_{cat}$ was comparable ($0.13 \times 10^{-1}$ s$^{-1}$) (Abramochkin et al., 1996, J. Biol. Chem. 271:22901-22907). Since it is trivial to run the present reactions at donor concentrations well above $K_M$, the lower apparent affinity for the present substrates should not affect the utility of the reaction. The binding affinity, which gave a $K_M$ of 124 µM for 4a, arises primarily from Phe binding interactions since the $K_I$ for adenosine inhibition was greater than 5 mM.

Modification of α-Casein

It is possible that larger protein substrates are modified with different efficiencies than peptide substrates (Leibowitz et al., 1971, J. Biol. Chem. 246:5207-5212; Taki et al., 2008, ChemBioChem 9:719-722; Abramochkin et al., 1996, J. Biol. Chem. 271:22901-22907). To address this question and to demonstrate the utility of the present method in tagging full-sized proteins with useful fluorophores or affinity purification tags, the milk protein α-casein (bearing a native N-terminal Arg after proteolysis of a leader sequence) was modified (Mercier et al., 1971, Eur. J, Biochem. 23:41-51). First, modification using Phe donor 4a was assessed by Edman degradation, where successful, quantitative addition of Phe was observed.

In a more complex set of experiments, α-casein was first modified with Azf using donor 4c and then a Cu-catalyzed Huisgen cycloaddition ("click" reaction) was used to append a fluorescein label as depicted in FIG. 4A (Kolb et al., 2001, Angew. Chem. Intl Ed. 40:2004-2021; Wang et al., 2003, J. Am. Chem. Soc. 125:3192-3193; Huisgen, 1989, Pure App. Chem. 61:613-628; Meldal, 2008, Chem. Rev. 108:2952-301.5). Prior to fluorescent-labeling, the initial transfer of Azf was analyzed by trypsin digest and MALDI MS of α-casein (FIG. 4C). The N-terminal peptide ArgProLys disappeared from the mass spectrum following modification and a peptide corresponding to AzfArgProLys was observed (also a mass corresponding to AzfArgProLys after loss of $N_2$ during ionization; $N_2$ loss was also observed for AzfLysAlaAcm). Complete conversion of α-casein was observed in MALDI MS due to double addition of 4c to drive the reaction.

After AaT-catalyzed modification of α-casein with Azf, residual 4c was removed by dialysis. AaT (His$_{10}$-tagged) was removed by treatment with Ni beads, and the azide-bearing protein was reacted with fluorescein alkyne (FlAlk) in the presence of Cu(I). The results of this labeling experiment, as well as appropriate control reactions, are shown in FIG. 4B. Fluorescent α-casein was only observed under the proper conditions (Lane 8), where both the chemoenzymatic labeling by AaT with 4c and the subsequent click reactions were successful. Finally, a similar labeling experiment in crude E. coli lysate with unpurified AaT was carried out. Azf transfer was successful, as shown by the observation of fluorescence after labeling with FlAlk. Control reactions showed no observable labeling of any protein, implying that endogenous levels of proteins terminating in Arg or Lys were too low to be observed.

The results presented herein demonstrate that E. coli aminoacyl tRNA transferase (AaT) modifies the N-terminus of a protein under conditions that maintain folding and activity of the protein. Thus, the results demonstrate that aminoacyl tRNA transferase is useful for conjugation to a protein. Enzymological analysis demonstrated that AaT can use the Xaa-A substrates with turnover numbers comparable to full-length aminoacyl tRNAs. Furthermore, neither the adenosine reaction byproduct nor aminoacylated protein product (at least in the case of the present reporter peptide) appreciably inhibited the reaction. In fact, the major obstacle to efficient transfer is donor hydrolysis, but this can be overcome by a second addition of donor molecule since the $K_I$ for inhibition by adenosine is greater than 5 mM.

The present AaT-only reaction sequence allows exploring the compatibility of Phe analogs lacking a primary α-amine with transfer by AaT. The wild type transferase seems to have a strong preference for the α-amine, as only N-methyl-phenylalanine was transferred. In contrast, the side chain pocket is quite permissive: transfer of bicyclic amino acid side chains was observed and Sisido has reported mutants capable of transferring tricyclic amino acids (Taki et al., 2008, ChemBioChem 9:719-722). Without wishing to be bound by any particular theory, it is believed that the present invention can transfer larger side chains including but not limited to benzophenone, biotin, and fluorescein derivatives.

The present reaction conditions and yields compare favorably to two well-established methods in the field. Subtiligase (reverse proteolysis) reactions can be carried out in a few hours, but rarely go to completion (Braisted et al., 1997, Solid-Phase Peptide Synthesis 289:298-313; Atwell et al., 1999, Proc. Natl. Acad. Sci. USA 96:9497-9502; Yoshihara et al., 2008, Bioorg. Med. Chem. Lett. 18:6000-6003). The pyridoxyl-5-phosphate (PUP) transamination reactions of Francis and co-workers can require elevated temperatures to achieve high yields and are subject to a number of side reactions (Scheck et al., 2008, J. Am. Chem. Soc., 130:11762-11770; Witus et al., 2010, J. Am. Chem. Soc. 132:16812-16817). AaT transfer reactions are highly specific (Lys side chain modifications were not observed in the present work) and can be driven to completion by subsequent repeated additions of donor. The present discovery of efficient transfer from simple adenosyl donors removes the limitations imposed by the selectivity of synthetases on the range of molecules that can be AaT substrates without restricting reaction scale by necessitating the synthesis of oligonucleotide donors. The present yields are comparable to those obtained with pdCpA donors, but pdCpA synthesis requires 6 steps, and overall yields are typically 25%. The present methods are distinct from the fully enzymatic synthetase-based methods (FIG. 1A), The present methods can be easily scaled up to modify larger quantities of protein since they do not require the use of purified tRNA.

It has been shown that the present method can be used to transfer reactive handles to the N-terminus under "protein friendly" (pH~7, high salt, 37° C.) conditions and that the labeled protein product can be easily purified afterward. Without wishing to be bound by any particular theory, it is believed that further mutation of AaT allows for the transfer of larger side chains that can permit direct transfer of fluorescent probes or affinity tags. Without wishing to be bound by any particular theory, it is believed that crystal structures can be used to redesign AaT to act on other N-terminal sequences through a combination of rational design and selection.

In view of the fact that the results presented herein demonstrate that AaT can modify α-casein in crude lysates coupled with the cell-permeability of the present moderately polar donors, AaT can be used as part of an in vivo labeling strategy.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of derivatizing the N-terminus of a protein or peptide with an amino acid, the method comprising contacting in a solution the protein or peptide with an aminoacyl tRNA transferase (AaT), or a mutant thereof, and an adenosine ester of the amino acid, whereby the N-terminus of the protein or peptide is derivatized with the amino acid.

2. The method of claim 1, wherein the method is carried out under conditions that do not significantly denature the protein or peptide.

3. The method of claim 1, wherein the solution is substantially free of a synthetase.

4. The method of claim 3, wherein the synthetase comprises aminoacyl tRNA synthetase.

5. The method of claim 1, wherein the amino acid comprises a compound of Formula

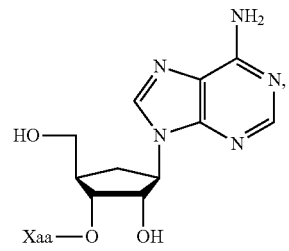

wherein Xaa is selected from the group consisting of:

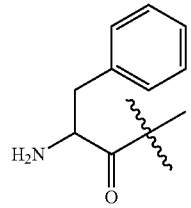
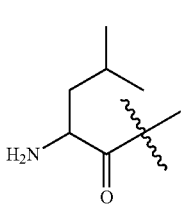
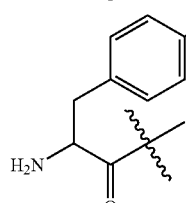
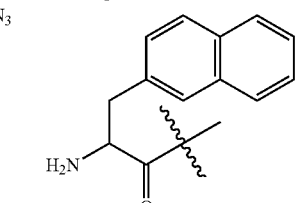
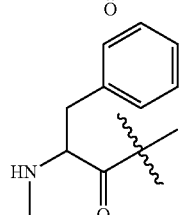
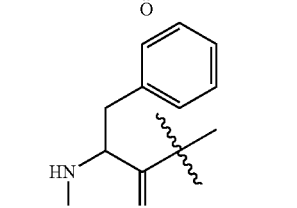
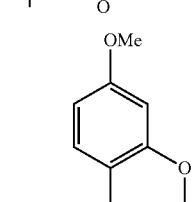
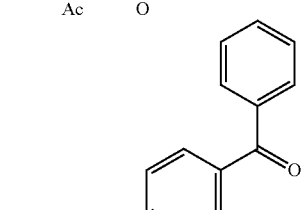
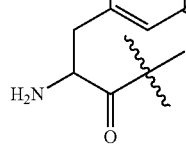
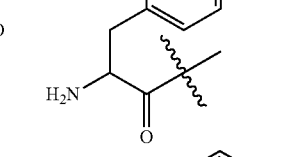
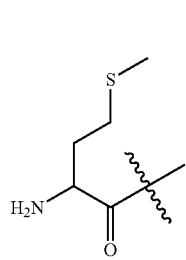
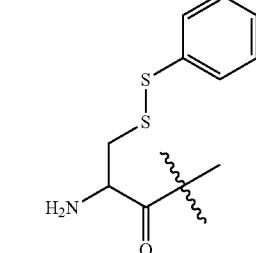

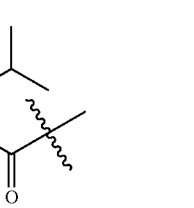

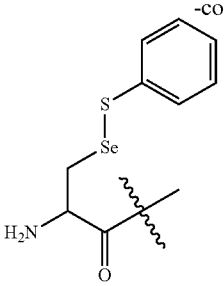

$X_1$ = S or Se
$X_2$ = S or Se
$R_1$ = H, i-Pr, Ph, PhOH
$R_2$ = Me, i-Pr, t-Bu, Ph, $CF_3$

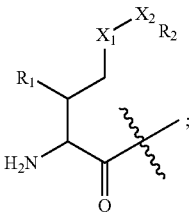

$X_1$ = S or Se
$X_2$ = S or Se
$R_1$ = H, i-Pr, Ph, PhOH
$R_2$ = Me, i-Pr, t-Bu, Ph, $CF_3$ a salt thereof and any combinations thereof.

6. The method of claim 1, wherein the amino acid is selected from the group consisting of cysteine, homocysteine, selenocysteine, selenohomocysteine, a derivative thereof and any combinations thereof.

7. The method of claim 1, wherein the transferase comprises *E. coli* AaT, *V. vulnificus* BpT, a mutant thereof and any combinations thereof.

8. The method of claim 1, wherein the amino acid comprises a detectable label.

9. The method of claim 8, wherein the detectable label is selected from the group consisting of a radioisotope, stable isotope, fluorophore, electron dense metals, biotin, DNA, RNA, antibody epitope, and any combinations thereof.

* * * * *

UNITED STATES PATENT AND TRADEMARK OFFICE
CERTIFICATE OF CORRECTION

PATENT NO. : 9,376,700 B2
APPLICATION NO. : 14/406864
DATED : June 28, 2016
INVENTOR(S) : E. James Petersson It is certified that error appears in the above-identified patent and that said Letters Patent is hereby corrected as shown below:

On the title page, item 73 Assignee: "Philadelphia, OR" should be changed to --Philadelphia, PA--

Signed and Sealed this
Twenty-third Day of August, 2016

Michelle K. Lee
*Director of the United States Patent and Trademark Office*